United States Patent
Saito et al.

(10) Patent No.: US 10,128,449 B2
(45) Date of Patent: Nov. 13, 2018

(54) METAL COMPLEX AND LIGHT EMITTING DEVICE USING THE SAME

(71) Applicant: Sumitomo Chemical Company, Limited, Tokyo (JP)

(72) Inventors: Takakazu Saito, Tsukuba (JP); Yusuke Ishii, Tsukuba (JP); Kazuei Ohuchi, Tsukuba (JP); Kohei Asada, Tsukuba (JP); Nobuhiko Akino, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 195 days.

(21) Appl. No.: 15/109,959

(22) PCT Filed: Dec. 18, 2014

(86) PCT No.: PCT/JP2014/084446
§ 371 (c)(1),
(2) Date: Jul. 6, 2016

(87) PCT Pub. No.: WO2015/105014
PCT Pub. Date: Jul. 16, 2015

(65) Prior Publication Data
US 2016/0329508 A1    Nov. 10, 2016

(30) Foreign Application Priority Data

Jan. 8, 2014    (JP) .................................. 2014-001404

(51) Int. Cl.
*H01L 51/00* (2006.01)
*C09K 11/06* (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
None
See application file for complete search history.

(56) References Cited

U.S. PATENT DOCUMENTS

| 2003/0068535 A1 | 4/2003 | Takiguchi et al. |
| 2007/0128466 A1 | 6/2007 | Nomura et al. |

(Continued)

FOREIGN PATENT DOCUMENTS

| CN | 1374315 A | 10/2002 |
| CN | 101611045 A | 12/2009 |

(Continued)

OTHER PUBLICATIONS

Extended European Search Report dated Aug. 11, 2017 in EP Application No. 14877977.0.
(Continued)

*Primary Examiner* — Jay Yang
(74) *Attorney, Agent, or Firm* — Panitch Schwarze Belisario & Nadel LLP

(57) ABSTRACT

A metal complex represented by the following formula (1) is provided.

(Continued)

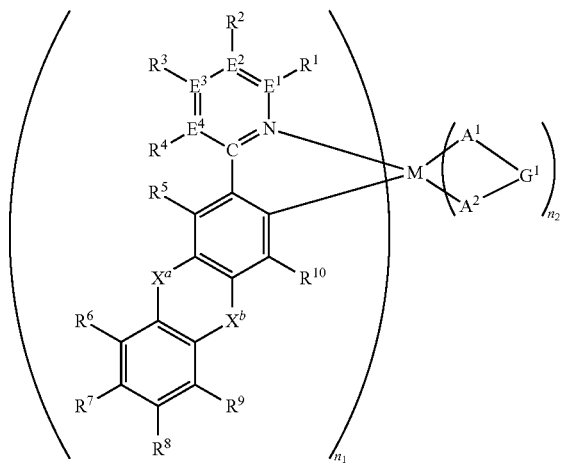

In formula (1), M represents an iridium atom or a platinum atom; $n_1$ represents 1, 2 or 3. $n_2$ represents 0, 1 or 2; $E^1$ to $E^4$ represent a nitrogen atom or a carbon atom; $R^1$ to $R^{10}$ represent a hydrogen atom, an alkyl group, a cycloalkyl group, an alkoxy group, a cycloalkoxy group, an aryl group, an aryloxy group, a monovalent heterocyclic group or a halogen atom; $X^a$ and $X^b$ represent a direct bond, an oxygen atom, a sulfur atom, —C(=O)—, —CR$^{Xa}_2$— or —NR$^{Xa}$—; $A^1$-$G^1$-$A^2$ represents an anionic bidentate ligand; and $G^1$ represents an atomic group constituting a bidentate ligand together with $A^1$ and $A^2$.

15 Claims, 2 Drawing Sheets

(51) Int. Cl.
*C07F 15/00* (2006.01)
*H01L 51/50* (2006.01)

(52) U.S. Cl.
CPC .. *H01L 51/5016* (2013.01); *C09K 2211/1007* (2013.01); *C09K 2211/1011* (2013.01); *C09K 2211/1029* (2013.01); *C09K 2211/1059* (2013.01); *C09K 2211/185* (2013.01)

(56) References Cited

U.S. PATENT DOCUMENTS

| | | |
|---|---|---|
| 2008/0210930 A1 | 9/2008 | Kamatani et al. |
| 2008/0299414 A1 | 12/2008 | Watanabe et al. |
| 2009/0123720 A1 | 5/2009 | Chen et al. |
| 2010/0019669 A1 | 1/2010 | Akino et al. |
| 2011/0114890 A1 | 5/2011 | Asada et al. |
| 2012/0205585 A1 | 8/2012 | Okamura et al. |

FOREIGN PATENT DOCUMENTS

| | | |
|---|---|---|
| CN | 102066524 A | 5/2011 |
| CN | 102596978 A | 7/2012 |
| EP | 1238981 A2 | 9/2002 |
| EP | 2305772 A1 | 4/2011 |
| JP | 2002332291 A | 11/2002 |
| JP | 2005023071 A | 1/2005 |
| JP | 2005023072 A | 1/2005 |
| JP | 2008179617 A | 8/2008 |
| JP | 2008531684 A | 8/2008 |
| JP | 2008297382 A | 12/2008 |
| JP | 2011105701 A | 6/2011 |
| WO | 2006/059758 A1 | 6/2006 |
| WO | 2013027633 A1 | 2/2013 |

OTHER PUBLICATIONS

Office Action dated Dec. 4, 2017 in CN Application No. 201480072204.4.
Int'l Search Report dated Mar. 31, 2015 in Int'l Application No. PCT/JP2014/084446 (English translation).
Int'l Preliminary Report on Patentability dated Jul. 12, 2016 in Int'l Application No. PCT/JP2014/084446 (English translation).
Office Action dated May 23, 2018 in CN Application No. 201480072204.4.

METAL COMPLEX AND LIGHT EMITTING DEVICE USING THE SAME

CROSS-REFERENCE TO RELATED APPLICATION

This application is a Section 371 of International Application No. PCT/JP2014/084446, filed Dec. 18, 2014, which was published in the Japanese language on Jul. 16, 2015, under International Publication No. WO 2015/105014 A1, and the disclosure of which is incorporated herein by reference.

TECHNICAL FIELD

The present invention relates to a metal complex, a composition containing the metal complex and a light emitting device containing the metal complex.

BACKGROUND ART various phosphorescent compounds showing light emission from the triplet excited state are investigated as a light emitting material used in a light emitting layer of a light emitting device. As this phosphorescent compound, a lot of metal complexes in which the central metal is a transition metal belonging to the group 5 or 6 of the periodic table are investigated. For example, Patent document 1 suggests a metal complex having as a ligand a phenylpyridine structure having a dendron (for example, a metal complex represented by the following formula).

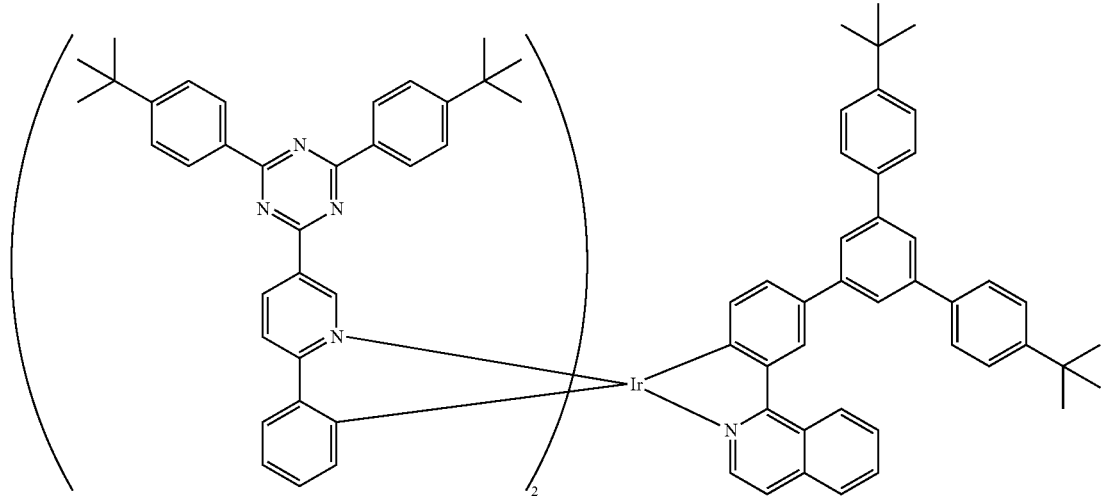

PRIOR ART DOCUMENT

Patent Document

Patent document 1: JP-A No. 2011-105701

SUMMARY OF THE INVENTION

Problem to be Solved by the Invention

However, the quantum yield of the metal complex described in the above-described Patent document 1 (hereinafter, also referred to as "PLQY") was not sufficient. Further, the full width at half maximum of a light emission spectrum of the metal complex described in the above-described Patent document 1 was not fully narrow.

Then, the present invention has an object of providing a metal complex excellent in quantum yield and showing excellent full width at half maximum of a light emission spectrum. Further, the present invention has an object of providing a composition containing the metal complex and a light emitting device produced using the metal complex.

Means for Solving the Problem

In a first aspect, the present invention provides a metal complex represented by the following formula (1):

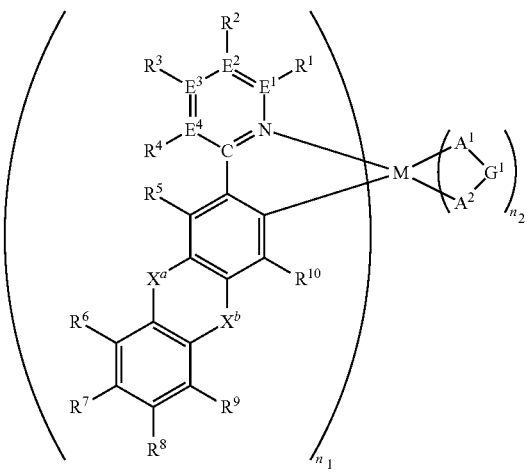

(1)

[wherein,

M represents an iridium atom or a platinum atom.

$n_1$ represents 1, 2 or 3. $n_2$ represents 0, 1 or 2. $n_1+n_2$ is 3 when M is an iridium atom and $n_1+n_2$ is 2 when M is a platinum atom.

$E^1$, $E^2$, $E^3$ and $E^4$ each independently represent a nitrogen atom or a carbon atom. When a plurality of $E^1$, $E^2$, $E^3$ and $E^4$ are present, they may be the same or different at each occurrence. $R^1$ is not present when $E^1$ is a nitrogen atom, $R^2$ is not present when $E^2$ is a nitrogen atom, $R^3$ is not present when $E^3$ is a nitrogen atom, and $R^4$ is not present when $E^4$ is a nitrogen atom.

$R^1$, $R^2$, $R^3$, $R^4$, $R^5$, $R^6$, $R^7$, $R^8$, $R^9$ and $R^{10}$ each independently represent a hydrogen atom, an alkyl group, a cycloalkyl group, an alkoxy group, a cycloalkoxy group, an aryl group, an aryloxy group, a monovalent heterocyclic group or a halogen atom, and these groups optionally have a substituent. When a plurality of $R^1$, $R^2$, $R^3$, $R^4$, $R^5$, $R^6$, $R^7$, $R^8$, $R^9$ and $R^{10}$ are present, they may be the same or different at each occurrence. $R^1$ and $R^2$, $R^2$ and $R^3$, $R^3$ and $R^4$, $R^4$ and $R^5$, $R^6$ and $R^7$, $R^7$ and $R^8$, and $R^8$ and $R^9$ each may be combined together to form a ring together with the atoms to which they are attached. At least one selected from the group consisting of $R^1$, $R^2$, $R^3$ and $R^4$ is a group represented by the following formula (D-A) or (D-B).

$X^a$ and $X^b$ each independently represent a direct bond, an oxygen atom, a sulfur atom, —C(=O)—, —CR$^{Xa}_2$— or —NR$^{Xa}$—. R$^{Xa}$ represents a hydrogen atom, an alkyl group, a cycloalkyl group, an aryl group or a monovalent heterocyclic group, and these groups optionally have a substituent. When a plurality of R$^{Xa}$ are present, they may be the same or different and may be combined together to form a ring together with the carbon atoms to which they are attached. When a plurality of $X^a$ and $X^b$ are present, they may be the same or different at each occurrence. At least one of $X^a$ and $X^b$ is an oxygen atom, a sulfur atom, —C(=O)—, —CR$^{Xa}_2$— or —NR$^{Xa}$—.

$A^1$-$G^1$-$A^2$ represents an anionic bidentate ligand, and $G^1$ represents an atomic group constituting a bidentate ligand together with $A^1$ and $A^2$. $A^1$ and $A^2$ each independently represent a carbon atom, an oxygen atom or a nitrogen atom, and these atoms each may be an atom constituting a ring. When a plurality of $A^1$-$G^1$-$A^2$ are present, they may be the same or different.]

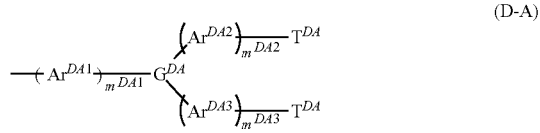

(D-A)

[wherein,
$m^{DA1}$, $m^{DA2}$ and $m^{DA3}$ each independently represent an integer of 0 or more.

$G^{DA}$ represents an aromatic hydrocarbon group or a heterocyclic group, and these groups optionally have a substituent.

$Ar^{DA1}$, $Ar^{DA2}$ and $Ar^{DA3}$ each independently represent an arylene group or a divalent heterocyclic group, and these groups optionally have a substituent. When a plurality of $Ar^{DA1}$, $Ar^{DA2}$ and $Ar^{DA3}$ are present, they may be the same or different at each occurrence.

$T^{DA}$ represents an aryl group or a monovalent heterocyclic group, and these groups optionally have a substituent. The plurality of $T^{DA}$ may be the same or different.]

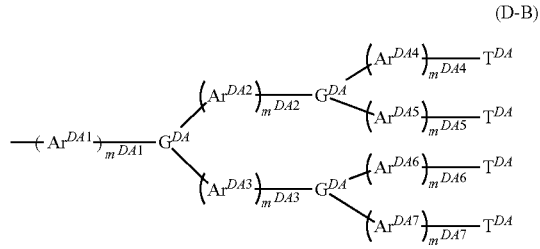

(D-B)

[wherein,
$m^{DA1}$, $m^{DA2}$, $m^{DA3}$, $m^{DA4}$, $m^{DA5}$, $m^{DA6}$ and $m^{DA7}$ each independently represent an integer of 0 or more.

$G^{DA}$ represents an aromatic hydrocarbon group or a heterocyclic group, and these groups optionally have a substituent. The plurality of $G^{DA}$ may be the same or different.

$Ar^{DA1}$, $Ar^{DA2}$, $Ar^{DA3}$, $Ar^{DA4}$, $Ar^{DA5}$, $Ar^{DA6}$ and $Ar^{DA7}$ each independently represent an arylene group or a divalent heterocyclic group, and these groups optionally have a substituent. When a plurality of $Ar^{DA1}$, $Ar^{DA2}$, $Ar^{DA3}$, $Ar^{DA4}$, $Ar^{DA5}$, $Ar^{DA6}$ and $Ar^{DA7}$ are present, they may be the same or different at each occurrence.

$T^{DA}$ represents an aryl group or a monovalent heterocyclic group, and these groups optionally have a substituent. The plurality of $T^{DA}$ may be the same or different.]

In a second aspect, the present invention provides a metal complex represented by the following formula (2):

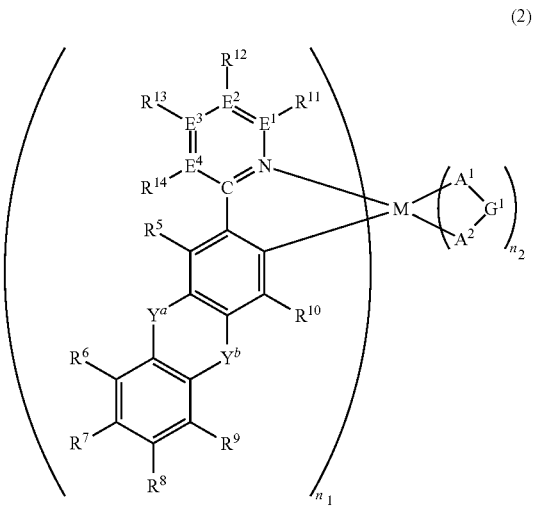

(2)

[wherein,
M represents an iridium atom or a platinum atom.

$n_1$ represents 1, 2 or 3. $n_2$ represents 0, 1 or 2. $n_1+n_2$ is 3 when M is an iridium atom, and $n_1+n_2$ is 2 when M is a platinum atom.

$E^1$, $E^2$, $E^3$ and $E^4$ each independently represent a nitrogen atom or a carbon atom. When a plurality of $E^1$, $E^2$, $E^3$ and $E^4$ are present, they may be the same or different at each occurrence. $R^{11}$ is not present when $E^1$ is a nitrogen atom, $R^{12}$ is not present when $E^2$ is a nitrogen atom, $R^{13}$ is not present when $E^3$ is a nitrogen atom, and $R^{14}$ is not present when $E^4$ is a nitrogen atom.

$R^{11}$, $R^{12}$, $R^{13}$, $R^{14}$, $R^5$, $R^6$, $R^7$, $R^8$, $R^9$ and $R^{10}$ each independently represent a hydrogen atom, an alkyl group, a cycloalkyl group, an alkoxy group, a cycloalkoxy group, an aryl group, an aryloxy group, a monovalent heterocyclic group or a halogen atom, and these groups optionally have a substituent. When a plurality of $R^{11}$, $R^{12}$, $R^{13}$, $R^{14}$, $R^5$, $R^6$, $R^7$, $R^8$, $R^9$ and $R^{10}$ are present, they may be the same or different at each occurrence. $R^{11}$ and $R^{12}$, $R^{12}$ and $R^{13}$, $R^{13}$ and $R^{14}$, $R^{14}$ and $R^5$, $R^6$ and $R^7$, $R^7$ and $R^8$, and $R^8$ and $R^9$ each may be combined together to form a ring together with the atoms to which they are attached.

$Y^a$ and $Y^b$ each independently represent a direct bond, an oxygen atom, a sulfur atom, —C(=O)—, —CR$^{Ya}$R$^{Yb}$— or —NR$^{Yc}$—. R$^{Ya}$ represents an alkyl group or a cycloalkyl group, and these groups optionally have an aryl group or a monovalent heterocyclic group as a substituent. R$^{Yb}$ represents an aryl group or a monovalent heterocyclic group, and these groups optionally have a substituent. R$^{Yc}$ represents a hydrogen atom, an alkyl group, a cycloalkyl group, an aryl group or a monovalent heterocyclic group, and these groups optionally have a substituent. At least one of $Y^a$ and $Y^b$ is —$CR^{Ya}R^{Yb}$—.

$A^1$-$G^1$-$A^2$ represents an anionic bidentate ligand, and $G^1$ represents an atomic group constituting a bidentate ligand together with $A^1$ and $A^2$. $A^1$ and $A^2$ each independently represent a carbon atom, an oxygen atom or a nitrogen atom, and these atoms each may be an atom constituting a ring. When a plurality of $A^1$-$G^1$-$A^2$ are present, they may be the same or different.].

In a third aspect, the present invention provides a composition comprising the above-described metal complex.

In a fourth aspect, the present invention provides a light emitting device produced using the above-described metal complex.

Effect of the Invention

The present invention can provide a metal complex showing excellent quantum yield and excellent in the full width at half maximum of an emission spectrum. Further, the present invention can provide a composition containing the metal complex and a light emitting device produced using the metal complex. Since the metal complex of the present invention is excellent in quantum yield, a light emitting device produced using the metal complex shall be excellent in external quantum efficiency. Additionally, since the metal complex of the present invention is excellent in the full width at half maximum of an emission spectrum, when a light emitting device produced using the metal complex is used together with a color filter and when the microcavity of a light emitting device produced using the metal complex is controlled, its external quantum efficiency shall be further excellent.

MODES FOR CARRYING OUT THE INVENTION

Figure 1:
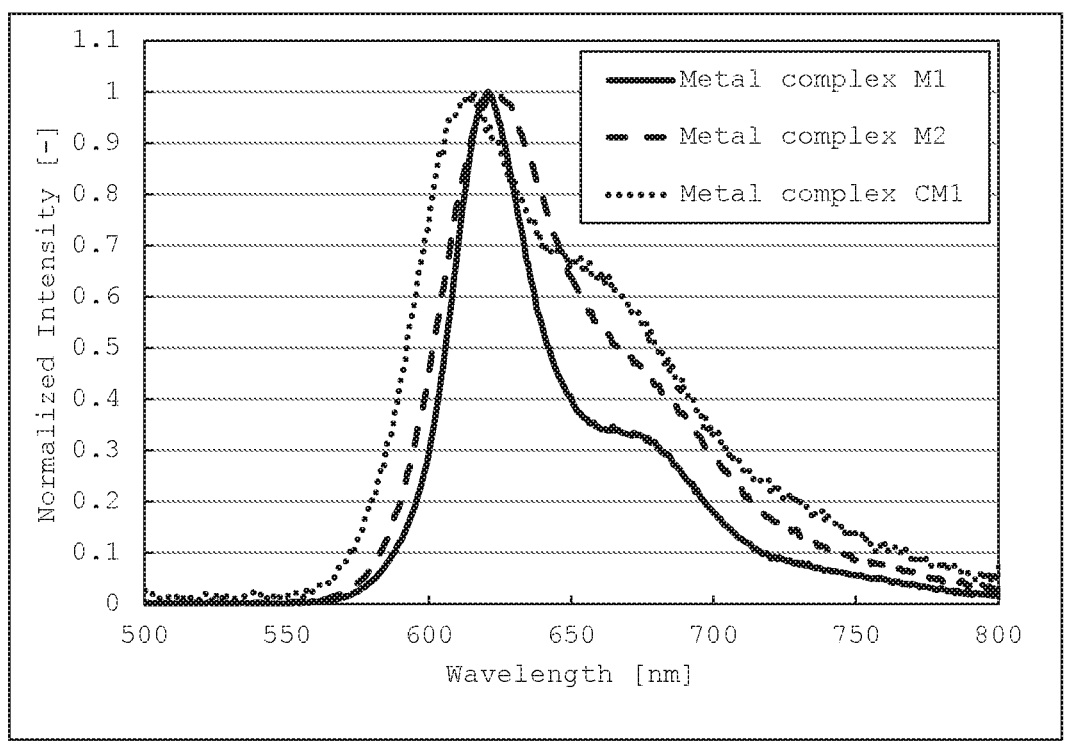
FIG. 1 shows the emission spectra of a metal complex M1, a metal complex M2 and a metal complex CM1.

Suitable embodiments of the present invention will be illustrated in detail below.
<Explanation of Common Term>
Terms commonly used in the present specification described below have the following meanings unless otherwise stated.

Me represents a methyl group, Et represents an ethyl group, Bu represents a butyl group, i-Pr represents an isopropyl group, and t-Bu represents a tert-butyl group.

In the present specification, the hydrogen atom may be a light hydrogen atom or a heavy hydrogen atom.

In the present specification, a solid line representing a bond to a central metal in a structural formula representing a metal complex denotes a coordinate bond or a covalent bond.

"Polymer compound" denotes a polymer having molecular weight distribution and having a polystyrene-equivalent number average molecular weight of $1 \times 10^3$ to $1 \times 10^8$. The total amount of constitutional units contained in the polymer compound is 100 mol %.

A polymer compound may be any of a block copolymer, a random copolymer, an alternating copolymer and a graft copolymer, and may also be another embodiment.

An end group of a polymer compound is preferably a stable group because if a polymerization active group remains intact at the end, when the polymer compound is used for fabrication of a light emitting device, the light emitting property or luminance life possibly becomes lower. This end group is preferably a group having a conjugated bond to the main chain, and includes groups bonding to an aryl group or a monovalent heterocyclic group via a carbon-carbon bond.

"Low molecular weight compound" denotes a compound having no molecular weight distribution and having a molecular weight of $1 \times 10^4$ or less.

"Constitutional unit" denotes a unit structure found once or more in a polymer compound.

"Alkyl group" may be any of linear or branched. The number of carbon atoms of the linear alkyl group is, not including the number of carbon atoms of a substituent, usually 1 to 50, preferably 3 to 30, more preferably 4 to 20. The number of carbon atoms of the branched alkyl groups is, not including the number of carbon atoms of a substituent, usually 3 to 50, preferably 3 to 30, more preferably 4 to 20.

The number of carbon atoms of a cycloalkyl group is, not including the number of carbon atoms of a substituent, usually 3 to 50, preferably 3 to 30, more preferably 4 to 20.

The alkyl group and cycloalkyl group optionally have a substituent, and examples thereof include a methyl group, an ethyl group, a propyl group, an isopropyl group, a butyl group, an isobutyl group, a tert-buty group, a pentyl group, an isoamyl group, 2-ethylbutyl group, a hexyl group, a heptyl group, a octyl group, a 2-ethylhexyl group, a 3-propylheptyl group, a decyl group, a 3,7-dimethyloctyl group, a 2-ethyloctyl group, a 2-hexyldecyl group, a dodecyl group and a cyclohexyl group, and groups obtained by substituting a hydrogen atom in these groups with an alkyl group, a cycloalkyl group, an alkoxy group, a cycloalkoxy group, an aryl group, a fluorine atom or the like, and the alkyl group and cycloalkyl group having a substituent include a trifluoromethyl group, a pentafluoroethyl group, a perfluorobutyl group, a perfluorohexyl group, a perfluorooctyl group, a 3-phenylpropyl group, a 3-(4-methylphenyl)propyl group, a 3-(3,5-di-n-hexyl-phenyl)propyl group, a 6-ethyloxyhexyl group, a cyclohexylmethyl group and a cyclohexylethyl group.

"Aryl group" denotes an atomic group remaining after removing from an aromatic hydrocarbon one hydrogen atom linked directly to a carbon atom constituting the ring. The number of carbon atoms of the aryl group is, not including the number of carbon atoms of a substituent, usually 6 to 60, preferably 6 to 20, more preferably 6 to 10.

The aryl group optionally has a substituent, and examples thereof include a phenyl group, a 1-naphthyl group, a 2-naphthyl group, a i-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 2-phenylphenyl group, a 3-phenylphenyl group, a 4-phenylphenyl group, and groups obtained by substituting a hydrogen atom in these groups with an alkyl group, a cycloalkyl group, an alkoxy group, a cycloalkoxy group, an aryl group, a fluorine atom or the like.

"Alkoxy group" may be any of linear or branched. The number of carbon atoms of the linear alkoxy group is, not including the number of carbon atoms of a substituent, usually 1 to 40, preferably 4 to 10. The number of carbon atoms of the branched alkoxy group is, not including the number of carbon atoms of a substituent, usually 3 to 40, preferably 4 to 10.

The number of carbon atoms of a cycloalkoxy group is, not including the number of carbon atoms of a substituent, usually 0.3 to 40, preferably 4 to 10.

The alkoxy group and cycloalkoxy group optionally have a substituent, and examples thereof include a methoxy group, an ethoxy group, a propyloxy group, an isopropyloxy group, a butyloxy group, an isobutyloxy group, a tert-butyloxy group, a pentyloxy group, a hexyloxy group, a cyclohexyloxy group, a heptyloxy group, a octyloxy group, a 2-ethylhexyloxy group, a nonyloxy group, a decyloxy group, a 3, 7-dimethyloctyloxy group and a lauryloxy group.

The number of carbon atoms of "Aryloxy group" is, not including the number of carbon atoms of a substituent, usually 6 to 60, preferably 7 to 48.

The aryloxy group optionally has a substituent, and examples thereof include a phenoxy group, a 1-naphthyloxy group, a 2-naphthyloxy group, a 1-anthracenyloxy group, a 9-anthracenyloxy group, a 1-pyrenyloxy group, and groups obtained by substituting a hydrogen atom in these groups with an alkyl group, a cycloalkyl group, an alkoxy group, a cycloalkoxy group, a fluorine atom or the like.

"p-Valent heterocyclic group" (p represents an integer of 1 or more) denotes an atomic group remaining after removing from a heterocyclic compound p hydrogen atoms among hydrogen atoms directly linked to a carbon atom or a hetero atom constituting the ring. Of p-valent heterocyclic groups, "p-valent aromatic heterocyclic groups" as an atomic group remaining after removing from an aromatic heterocyclic compound p hydrogen atoms among hydrogen atoms directly linked to a carbon atom or a hetero atom constituting the ring are preferable.

"Aromatic heterocyclic compound" denotes a compound in which the heterocyclic ring itself shows aromaticity such as oxadiazole, thiadiazole, thiazole, oxazole, thiophene, pyrrole, phosphole, furan, pyridine, pyrazine, pyrimidine, triazine, pyridazine, quinoline, isoquinoline, carbazole and dibenzophosphole, and a compound in which an aromatic ring is condensed to the heterocyclic ring even if the heterocyclic ring itself shows no aromaticity such as phenoxazine, phenothiazine, dibenzoborole, dibenzosilole and benzopyran.

The number of carbon atoms of the monovalent heterocyclic group is, not including the number of carbon atoms of a substituent, usually 2 to 60, preferably 4 to 20.

The monovalent heterocyclic group optionally has a substituent, and examples thereof include a thienyl group, a pyrrolyl group, a furyl group, a pyridyl group, a piperidyl group, a quinolyl group, an isoquinolyl group, a pyrimidinyl group, a triazinyl group, and groups obtained by substituting a hydrogen atom in these groups with an alkyl group, a cycloalkyl group, an alkoxy group, a cycloalkoxy group or the like.

"Halogen atom" denotes a fluorine atom, a chlorine atom, a bromine atom or an iodine atom.

"Amino group" optionally has a substituent, and a substituted amino group is preferable. The substituent which an amino group has is preferably an alkyl group, a cycloalkyl group, an aryl group or a monovalent heterocyclic group.

The substituted amino group includes, for example, a dialkylamino group, a dicycloalkylamino group and a diarylamino group.

The amino group includes, for example, a dimethylamino group, a diethylamino group, a diphenylamino group, a bis(4-methylphenyl)amino group, a bis(4-tert-butylphenyl) amino group and a bis(3,5-di-tert-butylphenyl)amino group.

"Alkenyl group" may be any of linear or branched. The number of carbon atoms of the linear alkenyl group, not including the number of carbon atoms of the substituent, is usually 2 to 30, preferably 3 to 20. The number of carbon atoms of the branched alkenyl group, not including the number of carbon atoms of the substituent, is usually 3 to 30, preferably 4 to 20.

The number of carbon atoms of a cycloalkenyl group, not including the number of carbon atoms of the substituent, is usually 0.3 to 30, preferably 4 to 20.

The alkenyl group and cycloalkenyl group optionally have a substituent, and examples thereof include a vinyl group, a 1-propenyl group, a 2-propenyl group, a 2-butenyl group, a 3-butenyl group, a 3-pentenyl group, a 4-pentenyl group, a 1-hexenyl group, a 5-hexenyl group, a 7-octenyl group, and these groups having a substituent.

"Alkynyl group" may be any of linear or branched. The number of carbon atoms of the alkynyl group, not including the number of carbon atoms of the substituent, is usually 2 to 20, preferably 3 to 20. The number of carbon atoms of the branched alkynyl group, not including the number of carbon atoms of the substituent, is usually 4 to 30, preferably 4 to 20.

The number of carbon atoms of a cycloalkynyl group, not including the number of carbon atoms of the substituent, is usually 4 to 30, preferably 4 to 20.

The alkynyl group and cycloalkynyl group optionally have a substituent, and examples thereof include an ethynyl group, a 1-propynyl group, a 2-propynyl group, a 2-butynyl group, a 3-butynyl group, a 3-pentynyl group, a 4-pentynyl group, a 1-hexenyl group, a 5-hexenyl group, and these groups having a substituent.

"Arylene group" denotes an atomic group remaining after removing from an aromatic hydrocarbon two hydrogen atoms linked directly to carbon atoms constituting the ring. The number of carbon atoms of the arylene group is, not including the number of carbon atoms of a substituent, usually 6 to 60, preferably 6 to 30, more preferably 6 to 18.

The arylene group optionally has a substituent, and examples thereof include a phenylene group, a naphthalenediyl group, an anthracenediyl group, a phenanthrenediyl group, a dihydrophenanthrenediyl group, a naphthacenediyl group, a fluorenediyl group, a pyrenediyl group, a perylenediyl group, a chrysenediyl group, and these groups having a substituent, preferably, groups represented by the formulae (A-1) to (A-20). The arylene group includes groups obtained by linking a plurality of these groups.

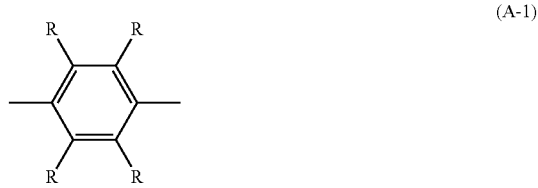

(A-1)

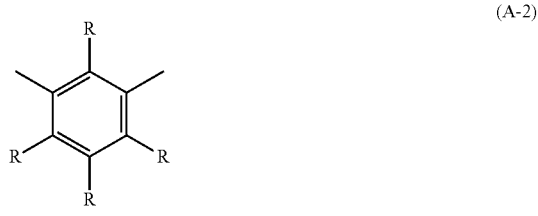

(A-2)

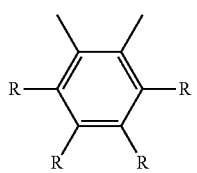 (A-3)
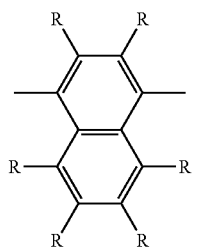 (A-4)
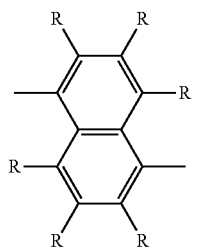 (A-5)
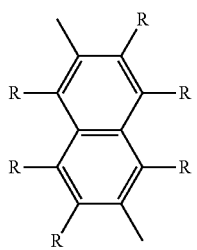 (A-6)
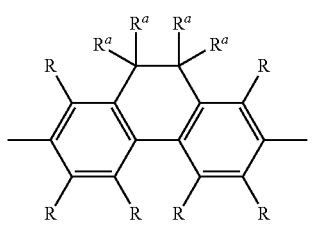 (A-7)
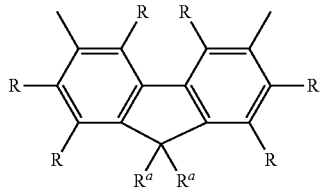 (A-8)
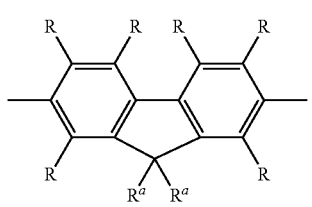 (A-9)
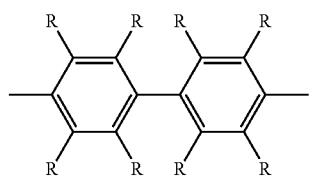 (A-10)
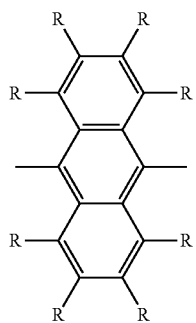 (A-11)
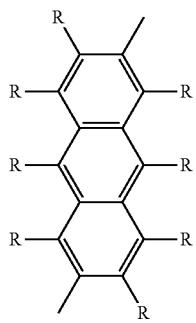 (A-12)
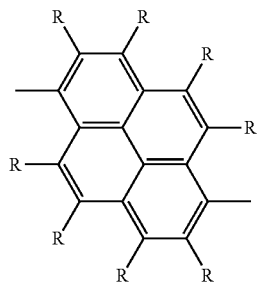 (A-13)
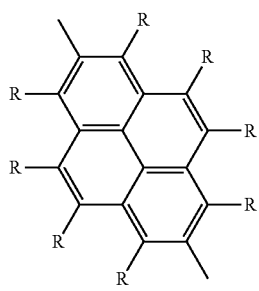 (A-14)

(A-15)
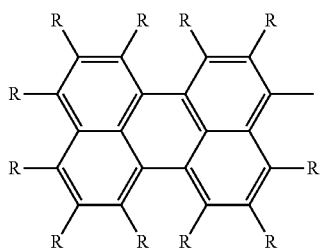

(A-16)
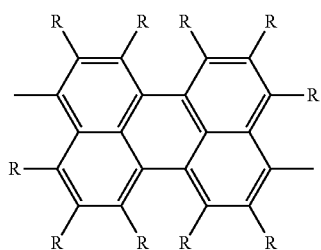

(A-17)
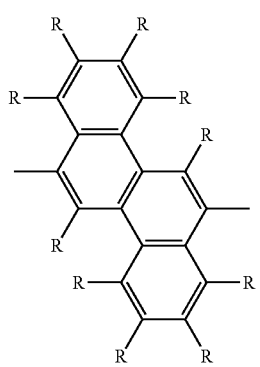

(A-18)
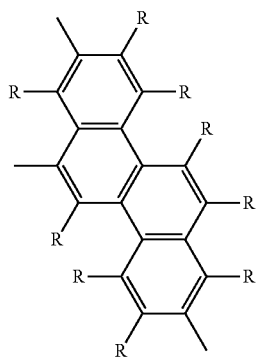

(A-19)
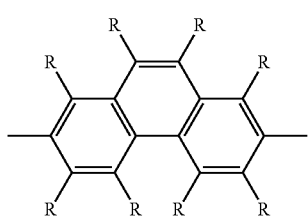

(A-20)
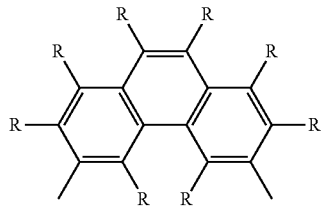

[wherein, R and $R^a$ each independently represent a hydrogen atom, an alkyl group, a cycloalkyl group, an aryl group or a monovalent heterocyclic group. The plurality of R and $R^a$ each may be the same or different, and adjacent $R^a$s may be combined together to form a ring together with the atoms to which they are attached.]

The number of carbon atoms of the divalent heterocyclic group is, not including the number of carbon atoms of a substituent, usually 2 to 60, preferably 3 to 30, more preferably 4 to 15.

The divalent heterocyclic group optionally has a substituent, and examples thereof include divalent groups obtained by removing from pyridine, diazabenzene, triazine, azanaphthalene, diazanaphthalene, carbazole, dibenzofuran, dibenzothiophene, dibenzosilole, phenoxazine, phenothiazine, acridine, dihydroacridine, furan, thiophene, azole, diazole and triazole two hydrogen atoms among hydrogen atoms linking directly to a carbon atom or a hetero atom constituting the ring, preferably groups represented by the formulae (AA-1) to (AA-34). The divalent heterocyclic group includes groups obtained by linking a plurality of these groups.

(AA-1)
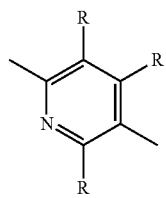

(AA-2)
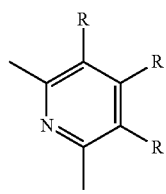

(AA-3)
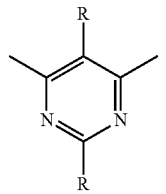

(AA-4)
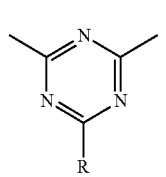

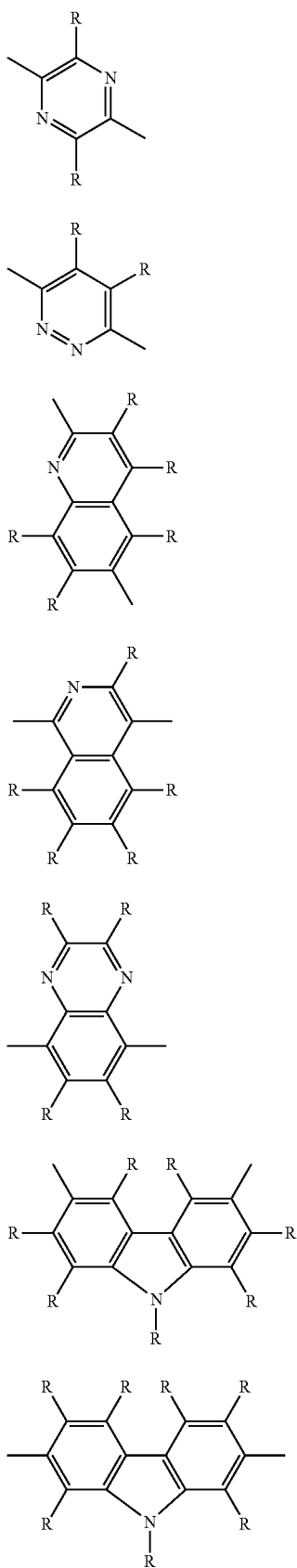
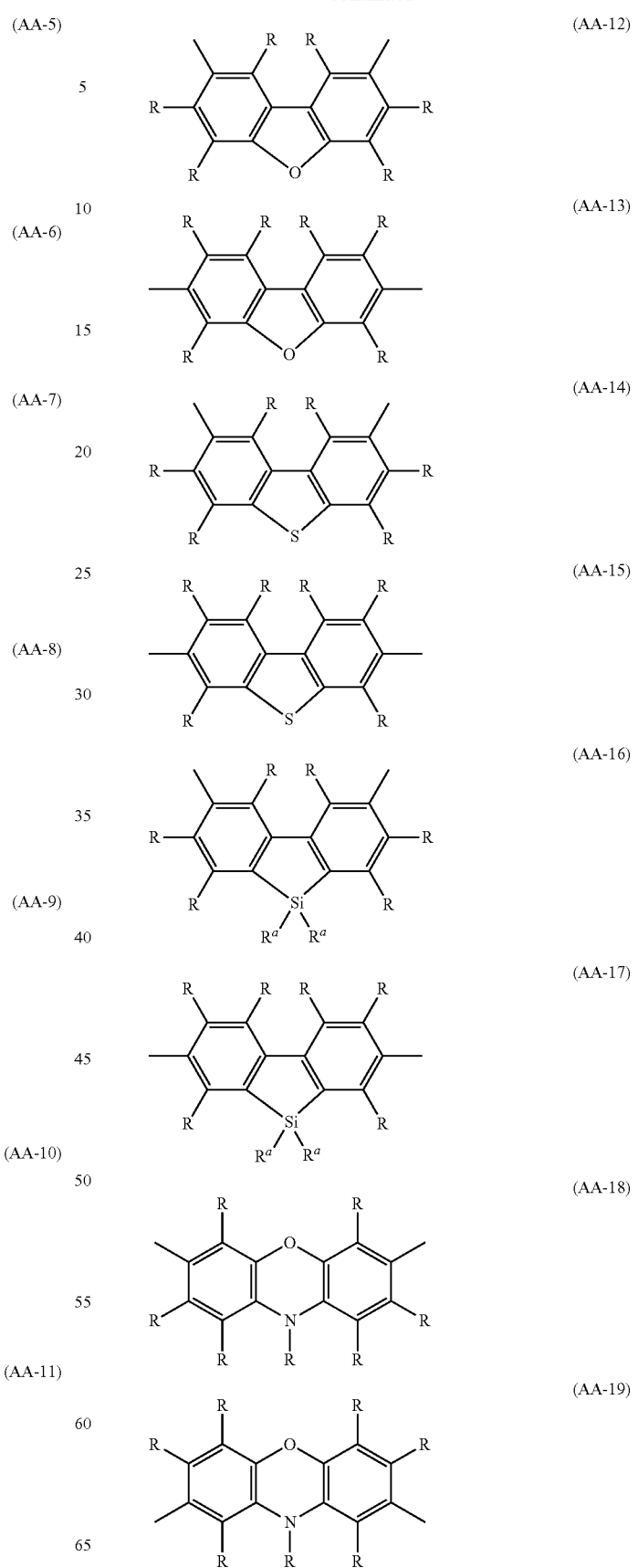

[wherein, R and R$^a$ represent the same meaning as described above.]

"Cross-linkable group" is a group capable of forming a new bond by being subjected to a heating treatment, an ultraviolet irradiation treatment, a radical reaction and the like, and is preferably a group represented by the formula (B-1), (B-2), (B-3), (B-4), (B-5), (B-6), (B-7), (B-8), (B-9), (B-10), (B-11), (B-12), (B-13), (B-14), (B-15), (B-16) or (B-17).

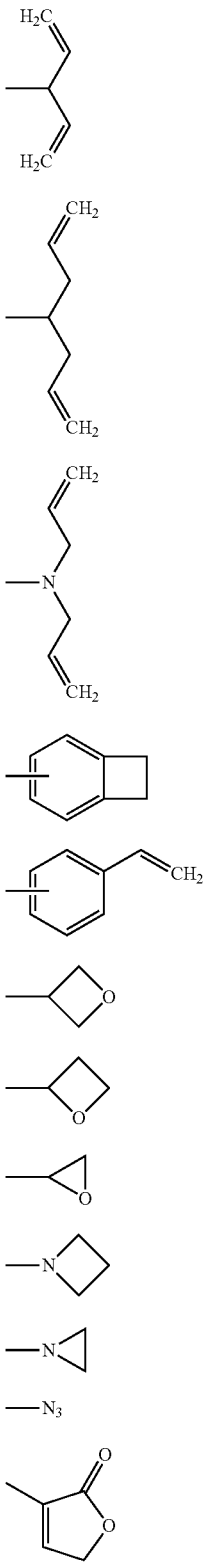

[wherein, these groups each optionally have a substituent.]

"Substituent" represents a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group or a cycloalkynyl group. The substituent may be a crosslinkable group.

"Dendron" is a group having a regular dendritic branched structure having a branching point at an atom or ring (a dendrimer structure). A compound having a dendron as a partial structure (called a dendrimer in some cases) includes, for example, structures described in literatures such as WO 02/067343, JP-A No. 2003-231692, WO 2003/079736, WO 2006/097717 and the like.

The groups represented by the formulae (D-A) and (D-B) are also a dendron.

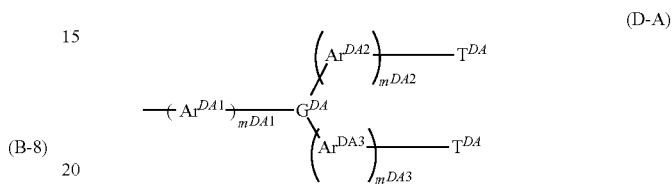

(D-A)

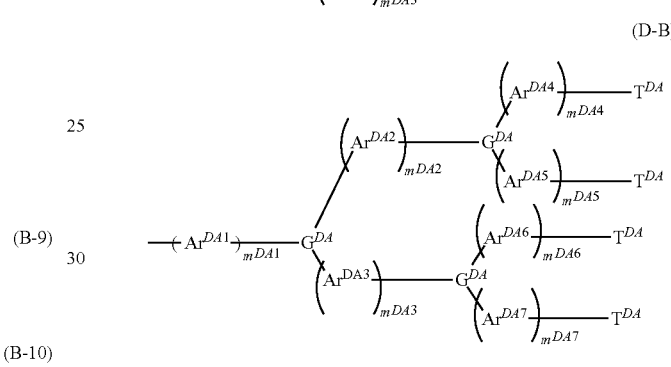

(D-B)

$m^{DA1}$, $m^{DA2}$, $m^{DA3}$, $m^{DA4}$, $m^{DA5}$, $m^{DA6}$ and $m^{DA7}$ are usually an integer of 10 or less, preferably an integer of 5 or less, more preferably 0 or 1, further preferably 0. It is preferable that $m^{DA1}$, $m^{DA2}$, $m^{DA3}$, $m^{DA4}$, $m^{DA5}$, $m^{DA6}$ and $m^{DA7}$ are the same integer.

$G^{DA}$ is preferably a group represented by the formulae (GDA-11) to (GDA-15), and these groups optionally have a substituent.

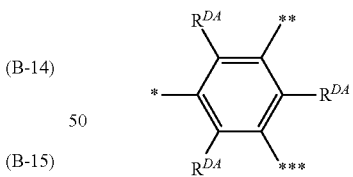

(GDA-11)

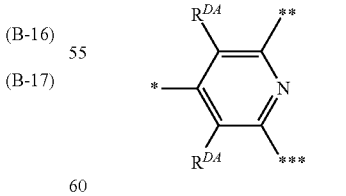

(GDA-12)

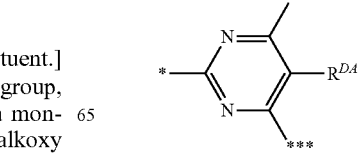

(GDA-13)

-continued (GDA-14)

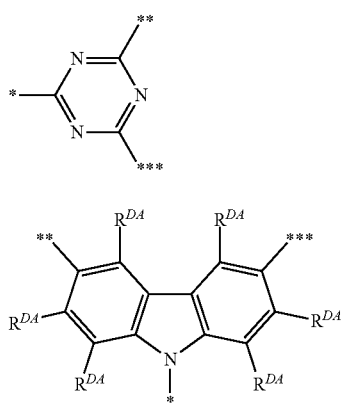

(GDA-15)

[wherein,

* represents a linkage to $Ar^{DA1}$ in the formula (D-A), $Ar^{DA1}$ in the formula (D-B), $Ar^{DA2}$ in the formula (D-B) or $Ar^{DA3}$ in the formula (D-B).

** represents a linkage to $Ar^{DA2}$ in the formula (D-A), $Ar^{DA2}$ in the formula (D-B), $Ar^{DA4}$ in the formula (D-B) or $Ar^{DA6}$ in the formula (D-B).

*** represents a linkage to $Ar^{DA3}$ in the formula (D-A), $Ar^{DA3}$ in the formula (D-B), $Ar^{DA5}$ in the formula (D-B) or $Ar^{DA7}$ in the formula (D-B).

$R^{DA}$ represents a hydrogen atom, an alkyl group, a cycloalkyl group, an alkoxy group, a cycloalkoxy group, an aryl group or a monovalent heterocyclic group, and these groups optionally have a substituent. When a plurality of $R^{DA}$ are present, they may be the same or different.]

$R^{DA}$ is preferably a hydrogen atom, an alkyl group, a cycloalkyl group, an alkoxy group or a cycloalkoxy group, more preferably a hydrogen atom, an alkyl group or cycloalkyl group, and these groups optionally have a substituent.

It is preferable that $Ar^{DA1}$, $A^{DA2}$, $Ar^{DA3}$, $Ar^{DA4}$, $Ar^{DA5}$, $Ar^{DA6}$ and $Ar^{DA7}$ are groups represented by the formulae (ArDA-1) to (ArDA-3).

(ArDA-1)

(ArDA-2)

-continued (ArDA-3)

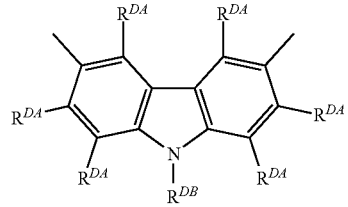

[wherein, $R^{DA}$ represents the same meaning as described above.

$R^{DB}$ represents a hydrogen atom, an alkyl group, a cycloalkyl group, an aryl group or a monovalent heterocyclic group, and these groups optionally have a substituent. When a plurality of $R^{DB}$ are present, they may be the same or different.]

$R^{DB}$ is preferably an alkyl group, a cycloalkyl group, an aryl group or a monovalent heterocyclic group, more preferably an aryl group or a monovalent heterocyclic group, further preferably an aryl group.

$T^{DA}$ is preferably groups represented by the formulae (TDA-1) to (TDA-3).

(TDA-1)

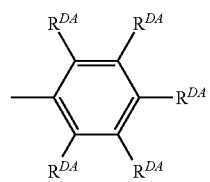

(TDA-2)

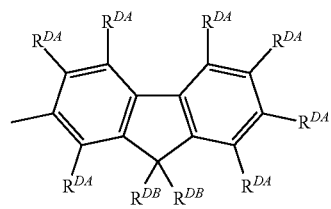

(TDA-3)

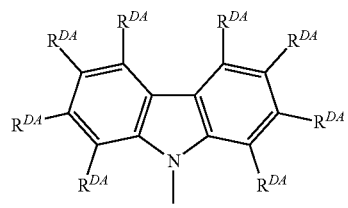

[wherein, $R^{DA}$ and $R^{DB}$ represent the same meaning described above.]

The group represented by the formula (D-A) is preferably a group represented by the formulae (D-A1) to (D-A3).

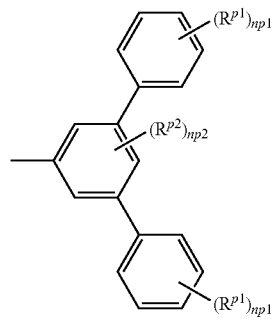
(D-A1)

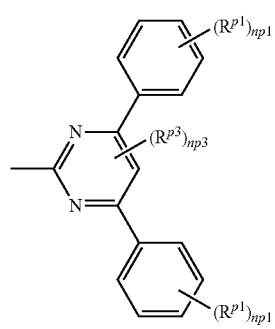
(D-A2)

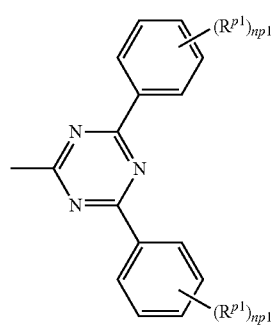
(D-A3)

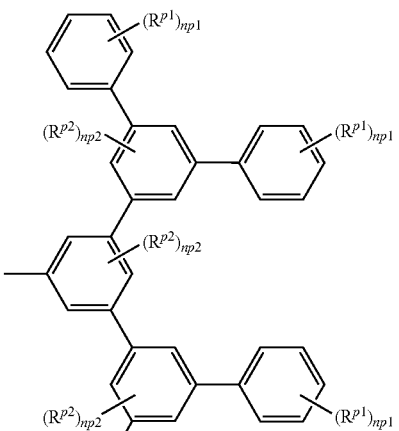
(D-B1)

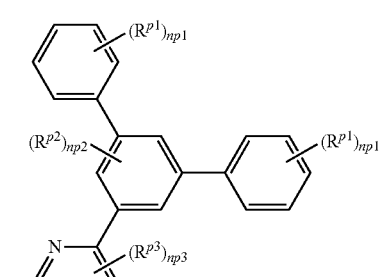
(D-B2)

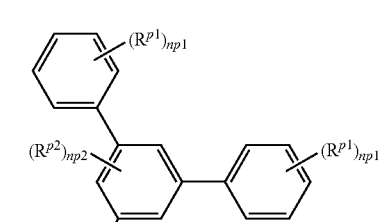
(D-B3)

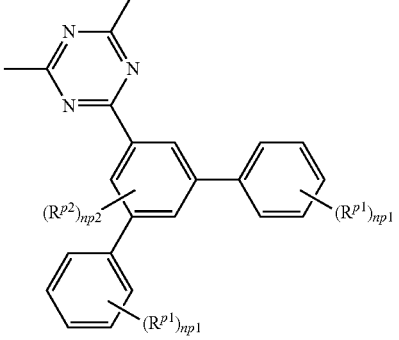

[wherein, $R^{p1}$, $R^{p2}$ and $R^{p3}$ each independently represent an alkyl group, a cycloalkyl group, an alkoxy group, a cycloalkoxy group or a halogen atom. When a plurality of $R^{P1}$ and $R^{p2}$ are present, they may be the same or different at each occurrence.

np1 represents an integer of 0 to 5, np2 represents an integer of 0 to 3, and np3 represents 0 or 1. The plurality of np1 may be the same or different.]

The group represented by the formula (D-B) is preferably a group represented by the formulae (D-B1) to (D-B3).

[wherein, $R^{p1}$, $R^{p2}$ and $R^{p3}$ each independently represent an alkyl group, a cycloalkyl group, an alkoxy group, a cycloalkoxy group or a halogen atom. When a plurality of $R^{p1}$ and $R^{p2}$ are present, they may be the same or different at each occurrence.

np1 represents an integer of 0 to 5, np2 represents an integer of 0 to 3, and np3 represents 0 or 1. When a plurality of np1 and np2 are present, they may be the same or different at each occurrence.]

np1 is preferably 0 or 1, more preferably 1. np2 is preferably 0 or 1, more preferably 0. np3 is preferably 0.

$R^{p1}$, $R^{p2}$ and $R^{p3}$ are preferable an alkyl group or a cycloalkyl group.

<Metal Complex>

Next, the metal complex of the present invention will be illustrated. The metal complex of the present invention is represented by the formula (1) or the formula (2).

The metal complex represented by the formula (1) has a group represented by the formula (D-A) or (D-B).

In the formula (1), at least one selected from the group consisting of $R^1$, $R^2$, $R^3$ and $R^4$ is a group represented by the formula (D-A) or (D-B), and when a plurality of $R^1$, $R^2$, $R^3$ and $R^4$ are present, at least one of them may be a group represented by the formula (D-A) or (D-B), and it is preferable that all of the plurality of $R^1$, all of the plurality of $R^2$, all of the plurality of $R^3$ or all of the plurality of $R^4$ are a group represented by the formula (D-A) or (D-B).

In the formula (1), at least one selected from the group consisting of $R^1$, $R^2$, $R^3$ and $R^4$ is preferably a group represented by the formula (D-A), more preferably a group represented by the formula (D-A1), (D-A2) or (D-A3) further preferably a group represented by the formula (D-A3), since the quantum yield of the metal complex of the present invention is more excellent.

In the formula (1), $R^2$ is preferably a group represented by the formula (D-A) or (D-B), more preferably a group represented by the formula (D-A), further preferably a group represented by the formula (D-A1), (D-A2) or (D-A3), particularly preferably a group represented by the formula (D-A3), since the quantum yield of the metal complex of the present invention is more excellent.

In the formula (1), when $R^1$, $R^2$, $R^3$ and $R^4$ are a group other than the group represented by the formula (D-A) or (D-B), $R^1$, $R^2$, $R^3$ and $R^4$ are preferably a hydrogen atom, an alkyl group, a cycloalkyl group, an aryl group, a monovalent heterocyclic group or a halogen atom, more preferably a hydrogen atom, an alkyl group, a cycloalkyl group or an aryl group, further preferably a hydrogen atom, since synthesis of the metal complex of the present invention is easy.

In the formula (1), $X^a$ is preferably a direct bond, an oxygen atom, a sulfur atom, —$CR^{Xa}_2$— or —$NR^{Xa}$—, more preferably a direct bond or —$CR^{Xa}_2$—, further preferably —$CR^{Xa}_2$—.

In the formula (1), $X^b$ is preferably a direct bond, an oxygen atom, a sulfur atom, —$CR^{Xa}_2$— or —$NR^{Xa}$—, more preferably a direct bond or —$CR^{Xa}_2$—, further preferably a direct bond.

At least one of $X^a$ and $X^b$ is an oxygen atom, a sulfur atom, —C(=O)—, —$CR^{Xa}_2$ or —$NR^{Xa}$—.

In the formula (1), the combination of $X^a$ and $X^b$ is preferably a combination in which $X^a$ is —$CR^{Xa}_2$— and $X^b$ is a direct bond, a combination in which $X^a$ is —$CR^{Xa}_2$— and $X^b$ is —$NR^{Xa}$—, a combination in which $X^a$ is an oxygen atom and $X^b$ is a direct bond, a combination in which $X^a$ is an oxygen atom and $X^b$ is —$NR^{Xa}$—, a combination in which $X^a$ is a sulfur atom and $X^b$ is a direct bond, a combination in which $X^a$ is —C(=O)— and $X^b$ is a direct bond, a combination in which $X^a$ is —$NR^{Xa}$— and $X^b$ is a direct bond, a combination in which $X^a$ is a direct bond and $X^b$ is —$CR^{Xa}_2$— or a combination in which $X^a$ is a direct bond and $X^b$ is a sulfur atom, more preferably a combination in which $X^a$ is —$CR^{Xa}_2$— and $X^b$ is a direct bond or a combination in which $X^a$ is a direct bond and $X^b$ is —$CR^{Xa}_2$—, further preferably a combination in which $X^a$ is —$CR^{Xa}_2$— and $X^b$ is a direct bond, particularly preferably a combination in which $X^a$ is —$CR^{Xb}R^{Xc}$— ($R^{Xb}$ represents an alkyl group or a cycloalkyl group, and these groups optionally have an aryl group or a monovalent heterocyclic group as a substituent. $R^{Xc}$ represents an aryl group or a monovalent heterocyclic group, and these groups optionally have a substituent.) and $X^b$ is a direct bond, since the metal complex of the present invention shows more excellent quantum yield.

In the formula (1), $R^{Xa}$ is preferably an alkyl group, a cycloalkyl group, an aryl group or a monovalent heterocyclic group, more preferably an alkyl group or an aryl group, since a light emitting device using the metal complex of the present invention shows excellent luminance life.

In the formula (1), $R^{Xb}$ is preferably an alkyl group, since a light emitting device using the metal complex of the present invention shows excellent luminance life.

In the formula (1), $R^{Xc}$ is preferably an aryl group, more preferably a phenyl group, since a light emitting device using the metal complex of the present invention shows excellent luminance life.

In the metal complex represented by the formula (2), at least one of $Y^a$ and $Y^b$ is —$CR^{Ya}R^{Yb}$—.

In the formula (2), when a plurality of $Y^a$ and $Y^b$ are present, at least one of them may be —$CR^{Ya}R^{Yb}$—, and it is preferable that all of the plurality of $Y^a$ or all of the plurality of $Y^b$ are —$CR^{Ya}R^{Yb}$—.

In the formula (2), $Y^a$ is preferably a direct bond, an oxygen atom, a sulfur atom, —$CR^{Ya}R^{Yb}$— or —$NR^{Yc}$—, more preferably a direct bond or —$CR^{Ya}R^{Yb}$—, further preferably —$CR^{Ya}R^{Yb}$—.

In the formula (2), $Y^b$ is preferably a direct bond, an oxygen atom, a sulfur atom, —$CR^{Ya}R^{Yb}$— or —$NR^{Yc}$—, more preferably a direct bond or —$CR^{Ya}R^{Yb}$—, further preferably a direct bond.

At least one of $Y^a$ and $Y^b$ is —$CR^{Ya}R^{Yb}$—.

In the formula (2), the combination of $Y^a$ and $Y^b$ is preferably a combination in which $Y^a$ is —$CR^{Ya}R^{Yb}$— and $Y^b$ is a direct bond, a combination in which $Y^a$ is —$CR^{Ya}R^{Yb}$— and $Y^b$ is —$NR^{Yc}$—, a combination in which $Y^a$ is —$CR^{Ya}R^{Yb}$— and $Y^b$ is an oxygen atom, a combination in which $Y^a$ is —$CR^{Ya}R^{Yb}$— and $Y^b$ is a sulfur atom, a combination in which $Y^a$ is a direct bond and $Y^b$ is —$CR^{Ya}R^{Yb}$—, a combination in which $Y^a$ is —$NR^{Yc}$— and $Y^b$ is —$CR^{Ya}R^{Yb}$—, a combination in which $Y^a$ is an oxygen atom and $Y^b$ is —$CR^{Ya}R^{Yb}$— or a combination in which $Y^a$ is a sulfur atom and $Y^b$ is —$CR^{Ya}R^{Yb}$—, more preferably a combination in which $Y^a$ is —$CR^{Ya}R^{Yb}$— and $Y^b$ is a direct bond or a combination in which $Y^a$ is a direct bond and $Y^b$ is —$CR^{Ya}R^{Yb}$—, further preferably a combination in which $Y^a$ is —$CR^{Ya}R^{Yb}$— and $Y^b$ is a direct bond, since the metal complex of the present invention shows more excellent quantum yield.

In the formula (2), $R^{Ya}$ is preferably an alkyl group optionally having a substituent, since a light emitting device using the metal complex of the present invention shows excellent luminance life.

In the formula (2), $R^{Yb}$ is preferably an aryl group optionally having a substituent, more preferably a phenyl group optionally having a substituent, since a light emitting device using the metal complex of the present invention shows excellent luminance life.

In the formula (2), at least one selected from the group consisting of $R^{11}$, $R^{12}$, $R^{13}$ and $R^{14}$ is preferably a group represented by the formula (D-A) or (D-B), since the metal complex of the present invention shows more excellent quantum yield.

When a plurality of $R^{11}$, $R^{12}$, $R^{13}$ and $R^{14}$ are present, it is preferable that all of the plurality of $R^{11}$, all of the plurality of $R^{12}$, all of the plurality of $R^{13}$ or all of the plurality of $R^{14}$ are a group represented by the formula (D-A) or (D-B).

In the formula (2), at least one selected from the group consisting of $R^{11}$, $R^{12}$, $R^{13}$ and $R^{14}$ is preferably a group represented by the formula (D-A), more preferably a group represented by the formula (D-A1), (D-A2) or (D-A3), further preferably a group represented by the formula (D-A3), since the metal complex of the present invention shows more excellent quantum yield.

In the formula (2), $R^{12}$ is preferably a group represented by the formula (D-A) or (D-B), more preferably a group represented by the formula (D-A), further preferably a group represented by the formula (D-A1), (D-A2) or (D-A3), particularly preferably a group represented by the formula (D-A3), since the metal complex of the present invention shows more excellent quantum yield.

In the formula (2), when $R^{11}$, $R^{12}$, $R^{13}$ and $R^{14}$ are a group other than the group represented by the formula (D-A) or (D-B), $R^{11}$, $R^{12}$, $R^{13}$ and $R^{14}$ are preferably a hydrogen atom, an alkyl group, a cycloalkyl group, an aryl group, a monovalent heterocyclic group or a halogen atom, more preferably a hydrogen atom, an alkyl group, a cycloalkyl group or an aryl group, further preferably a hydrogen atom, since synthesis of the metal complex of the present invention is easy.

In the formula (1) and the formula (2), M is preferably an iridium atom, since a light emitting device using the metal complex of the present invention shows excellent luminance life.

In the formula (1) and the formula (2), $n_2$ is preferably 0, since a light emitting device using the metal complex of the present invention shows excellent luminance life.

In the formula (1) and the formula (2), $E^1$, $E^2$, $E^3$ and $E^4$ are preferably a carbon atom, since synthesis of the metal complex of the present invention is easy.

In the formula (1) and the formula (2), $R^5$, $R^6$, $R^9$ and $R^{10}$ are preferably a hydrogen atom, an alkyl group, a cycloalkyl group, an aryl group, a monovalent heterocyclic group or a halogen atom, more preferably a hydrogen atom, an alkyl group, a cycloalkyl group or an aryl group, further preferably a hydrogen atom, since synthesis of the metal complex of the present invention is easy.

In the formula (1) and the formula (2), $R^7$ and $R^8$ are preferably a hydrogen atom, an alkyl group, a cycloalkyl group, an aryl group, a monovalent heterocyclic group or a halogen atom, more preferably a hydrogen atom, an alkyl group, a cycloakyl group or an aryl group, further preferably a hydrogen atom, an alkyl group or a cycloalkyl group, since the solubility of the metal complex of the present invention in a solvent and the film formability thereof are excellent.

In the formulae (1) and (2), the anionic bidentate ligand represented by $A^1$-$G^1$-$A^2$ includes, for example, ligands represented by the following formulae.

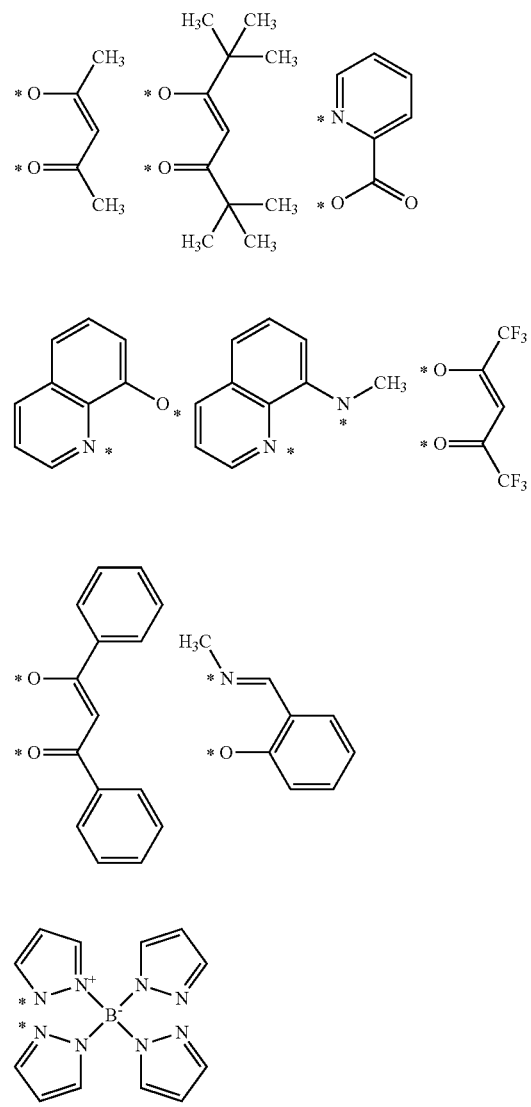

[wherein, * represents a position linking to an iridium atom or a platinum atom.]

In the formulae (1) and (2), the anionic bidentate ligand represented by $A^1$-$G^1$-$A^2$ may be ligands represented by the following formulae. The anionic bidentate ligand represented by $A^1$-$G^1$-$A^2$ is different from the ligand of which number is defined by the subscript $n^1$.

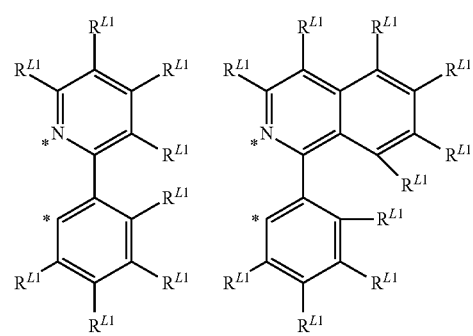

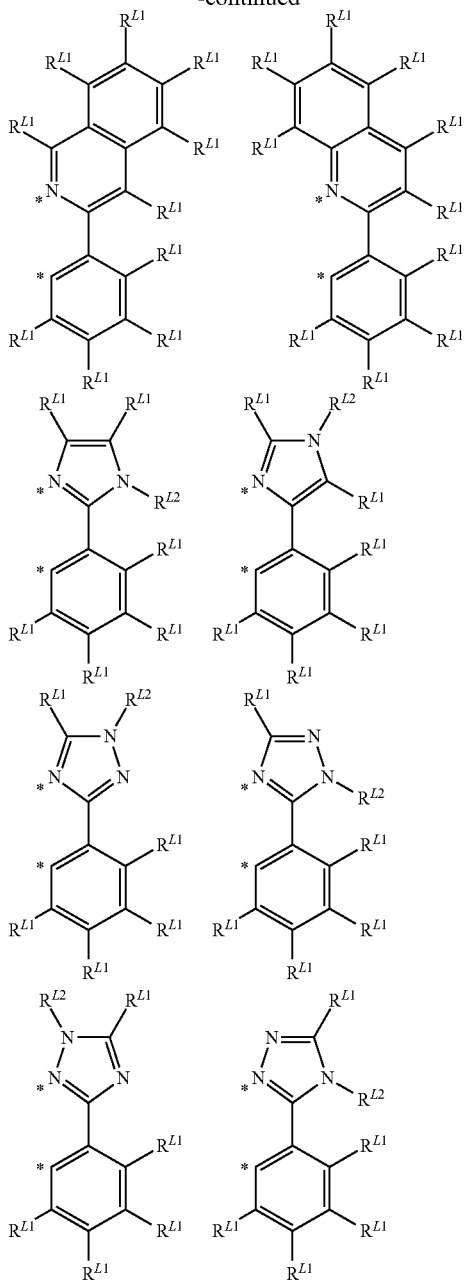

[wherein,
* represents a position linking to an iridium atom or a platinum atom.

$R^{L1}$ represents a hydrogen atom, an alkyl group, a cycloalkyl group, an aryl group, a monovalent heterocyclic group or a halogen atom, and these groups optionally have a substituent. The plurality of $R^{L1}$ may be the same or different.

$R^{L2}$ represents an alkyl group, a cycloalkyl group, an aryl group, a monovalent heterocyclic group or a halogen atom, and these groups optionally have a substituent.]

The metal complex represented by the formula (1) or the formula (2) includes, for example, metal complexes represented by the following formulae (Ir-1) to (Ir-26). Of them, metal complexes represented by the formula (Ir-1), (Ir-2), (Ir-3), (Ir-4), (Ir-15), (Ir-16), (Ir-17), (Ir-18) (Ir-19) or (Ir-20) are preferable, metal complexes represented by the formula (Ir-1), (Ir-2), (Ir-3), (Ir-4), (Ir-15) or (Ir-16) are more preferable, since the metal complex of the present invention shows more excellent quantum yield. Of them, metal complexes represented by the formula (Ir-1), (Ir-2), (Ir-3) or (Ir-4) are further preferable, metal complexes represented by the formula (Ir-1) or (Ir-3) are particularly preferable, since synthesis of the metal complex of the present invention is easy.

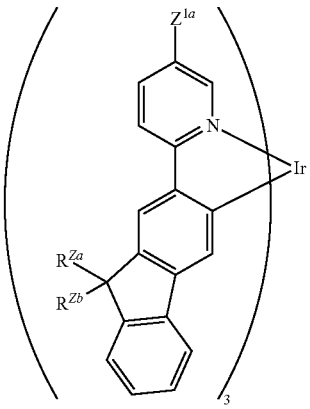

(Ir-1)

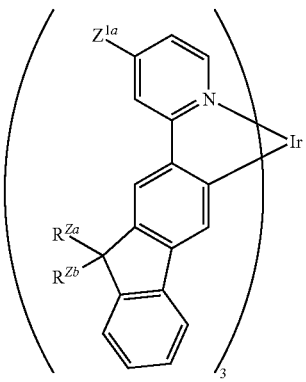

(Ir-2)

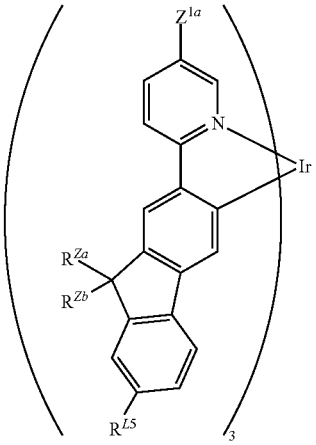

(Ir-3)

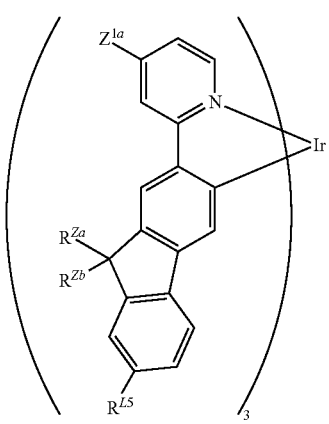 (Ir-4)
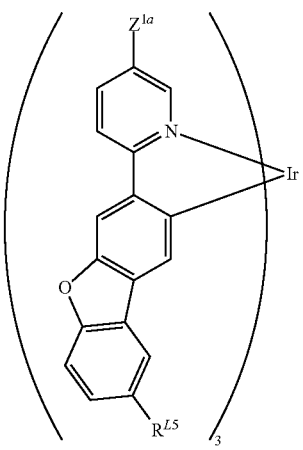 (Ir-7)
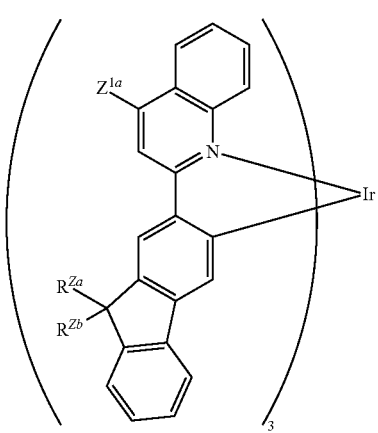 (Ir-5)
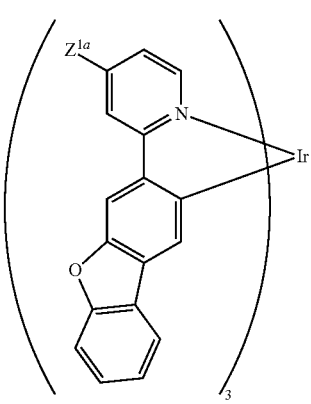 (Ir-8)
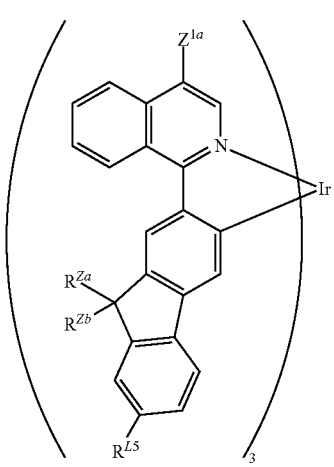 (Ir-6)
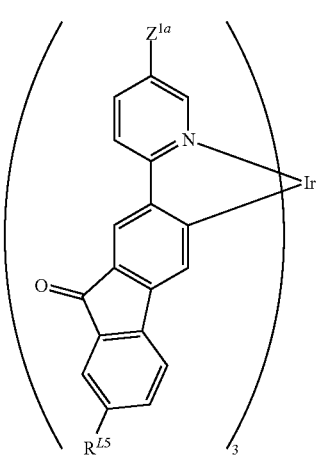 (Ir-9)

-continued
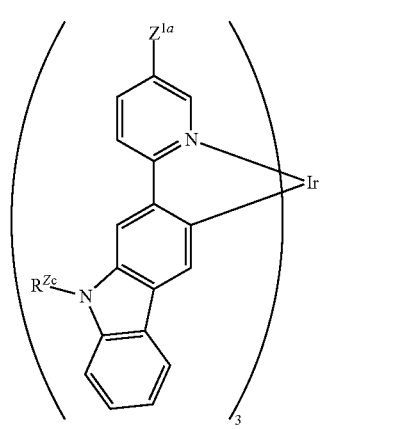
(Ir-10)
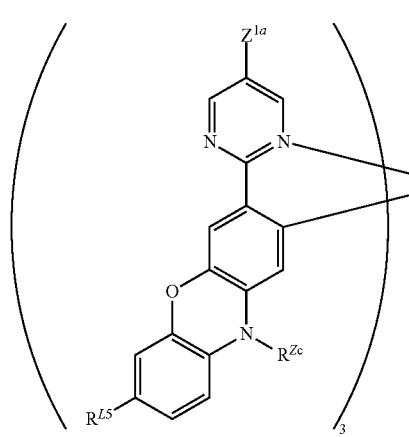
(Ir-11)
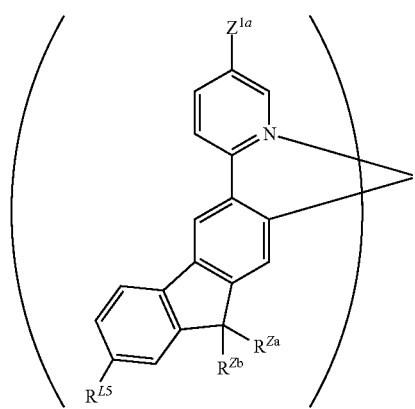
(Ir-12)
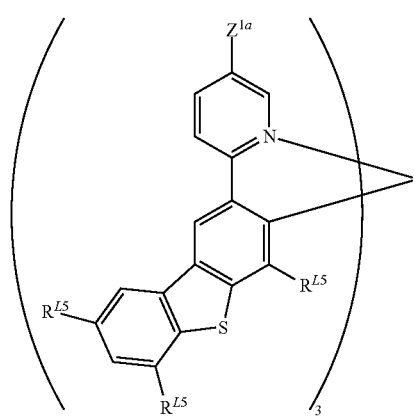
(Ir-13)
-continued
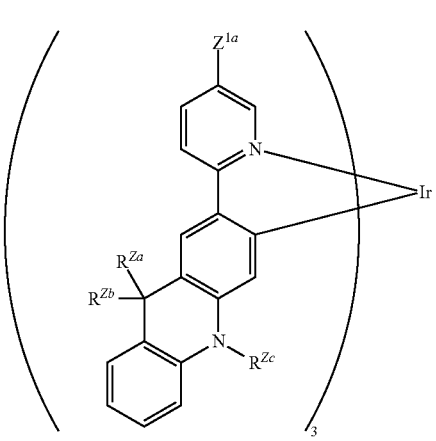
(Ir-14)
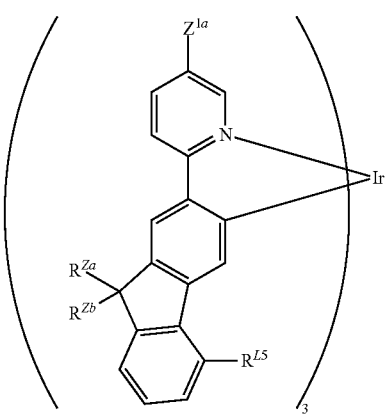
(Ir-15)
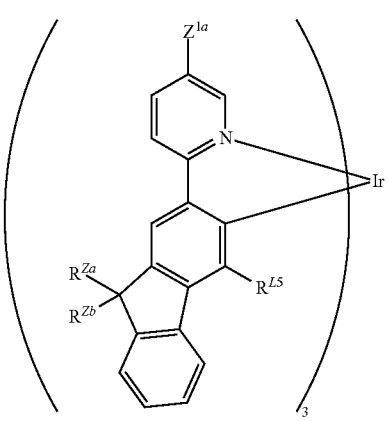
(Ir-16)

(Ir-17)
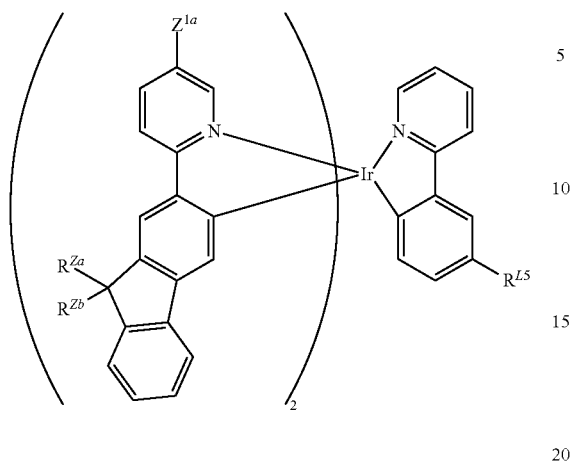
(Ir-18)
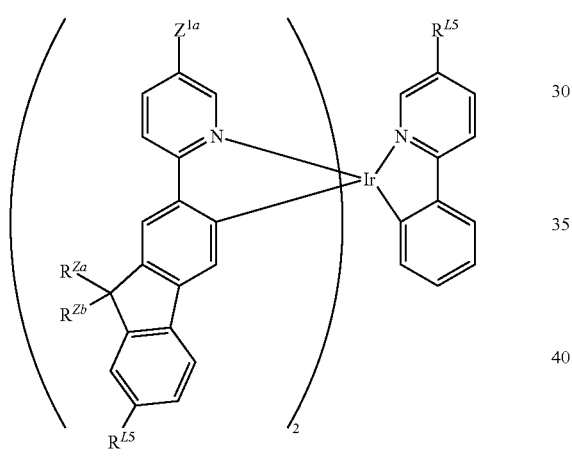
(Ir-19)
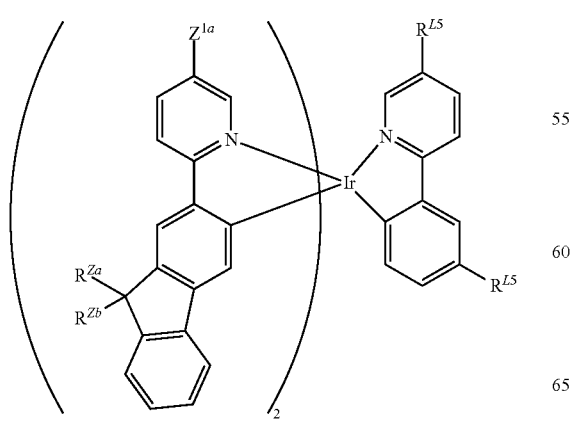
(Ir-20)
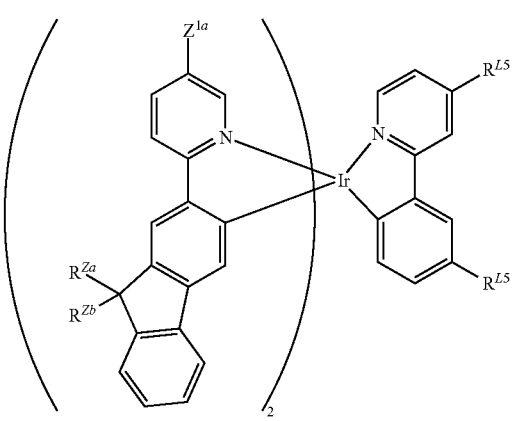
(Ir-21)
(Ir-22)

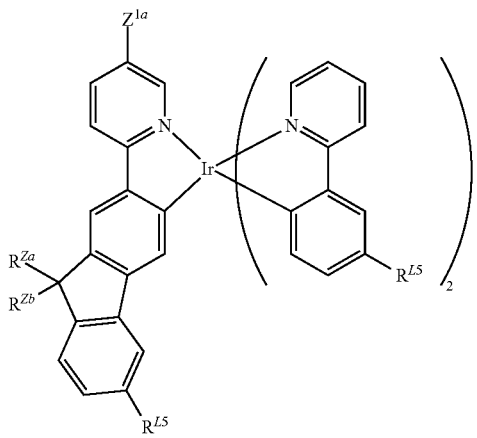
(Ir-23)

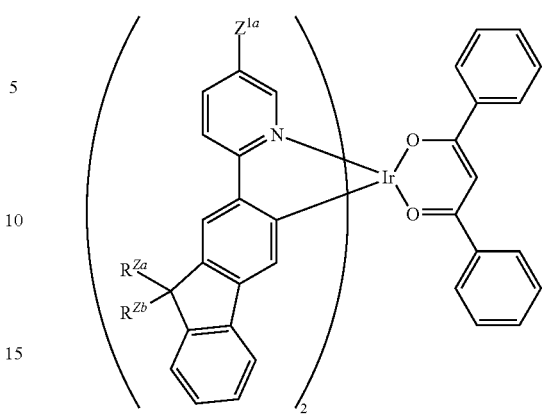
(Ir-26)

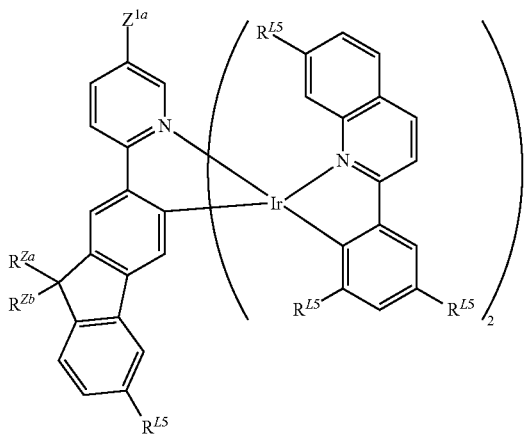
(Ir-24)

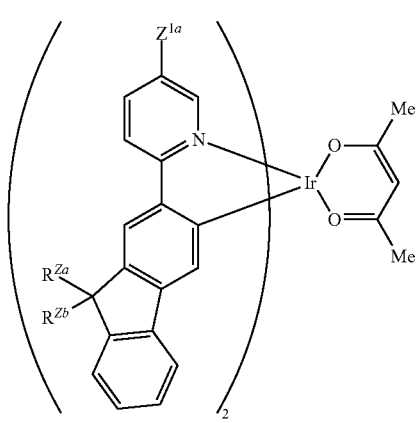
(Ir-25)

[In the formulae (Ir-1) to (Ir-26), $R^{L5}$ is a group selected from an alkyl group, a cycloalkyl group, a halogen atom, an aryl group, a 1,3,5-triazin-2-yl group having an aryl group at positions 4 and 6 as a substituent, a 1,3,5-pyrimidin-2-yl group having an aryl group at positions 4 and 6 as a substituent, or a dendron. When a plurality of $R^{L5}$ are present, they may be the same or different.

$R^{Za}$ is a group represented by the above-described $R^{Xa}$ or $R^{Ya}$, $R^{Zb}$ is a group represented by the above-described $R^{Xa}$ or $R^{Yb}$, and $R^{Zc}$ is a group represented by the above-described $R^{Xa}$ or $R^{Yc}$. When $R^{Za}$ is a group represented by $R^{Xa}$, $R^{Zb}$ and $R^{Zc}$ are a group represented by $R^{Xa}$, and when $R^{Za}$ is a group represented by $R^{Ya}$, $R^{Zb}$ is a group represented by $R^{Yb}$ and $R^{Zc}$ is a group represented by $R^{Yc}$. When a plurality of $R^{Za}$ are present, they may be the same or different, when a plurality of $R^{Zb}$ are present, they may be the same or different, and when a plurality of $R^{Zc}$ are present, they may be the same or different.

$Z^{1a}$ is a hydrogen atom, an alkyl group, a cycloalkyl group, an aryl group, or a group represented by the above-described formula (D-A) or (D-B). $Z^{1a}$ is a group represented by the formula (D-A) or (D-B), when $R^{Za}$ is a group represented by $R^{Xa}$ and when $R^{Zb}$ is a group represented by $R^{Xa}$. When a plurality of $Z^{1a}$ are present, they may be the same or different.]

In the formulae (Ir-1) to (Ir-26), $R^{L5}$ is preferably a group selected from groups represented by the formula (II-1) to the formula (II-15) in Group II described below and groups represented by the formula (III-1) to the formula (III-17) in Group III described below.

$Z^{1a}$ is preferably a group selected from groups represented by the formula (III-1) to the formula (III-17) in Group III described below as the group represented by the above-described formula (D-A).

<Group II>

——Me  (II-1)

——$C_3H_7$  (II-2)

——Bu  (II-3)

——t-Bu  (II-4)

——$C_6H_{13}$  (II-5)

(II-6) 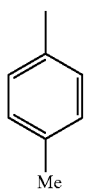
II-7 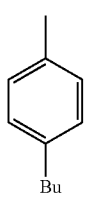
II-8 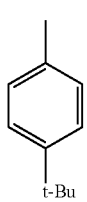
II-9 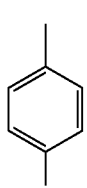
II-10 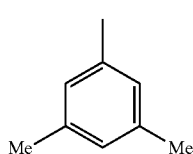
II-11 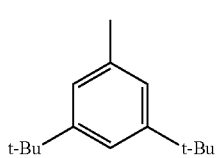
II-12 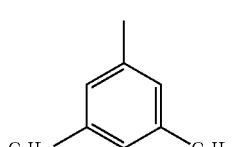
II-14 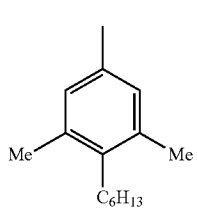
I-15 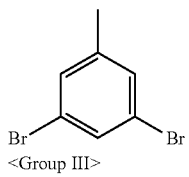
<Group III>
(III-1) 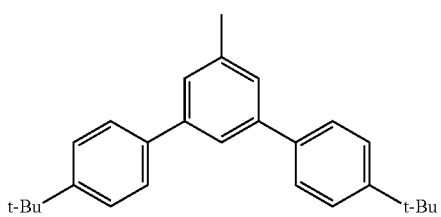
(III-2) 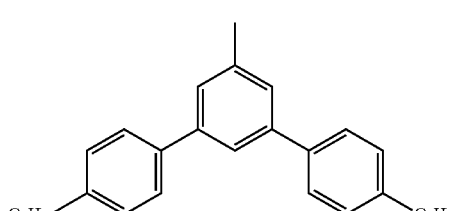
(III-3) 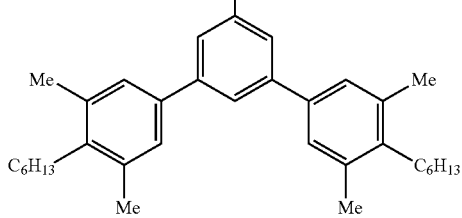
(III-4) 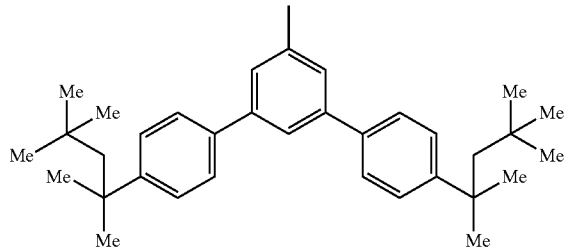
(III-5) 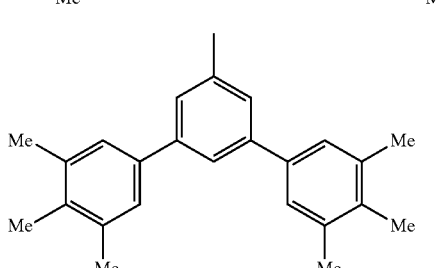
(III-6) 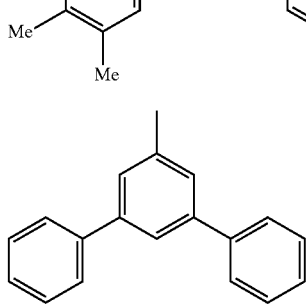

(III-7)
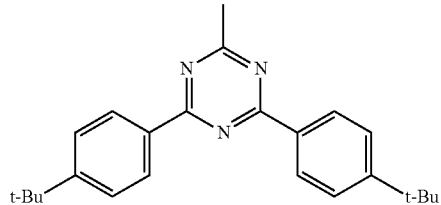

(III-8)
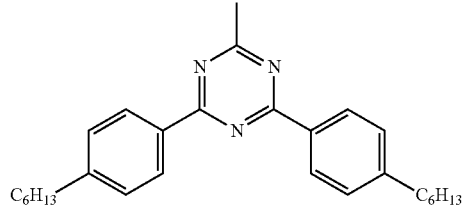

(III-9)
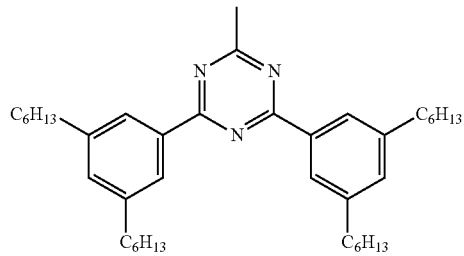

(III-10)

(III-11)
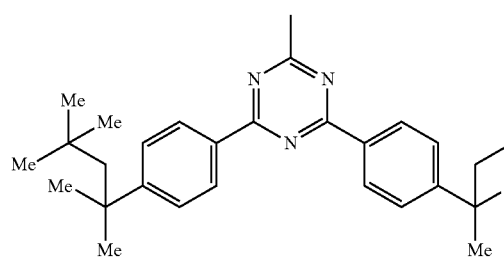

(III-12)
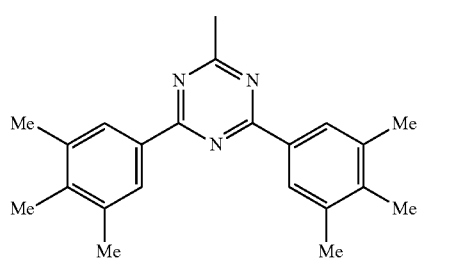

(III-13)
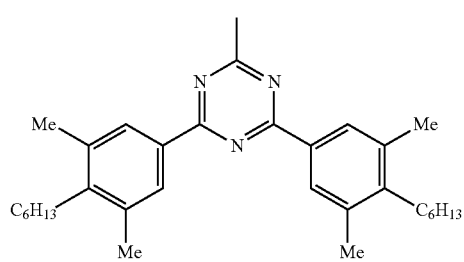

(III-14)
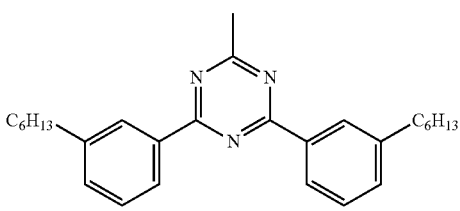

(III-15)
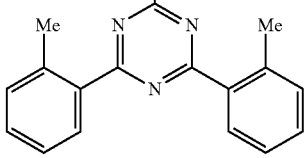

(III-16)
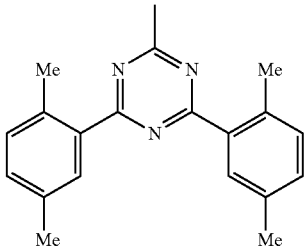

(III-17)
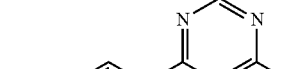
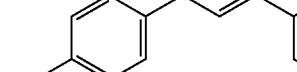

In the formula (Ir-1) to the formula (Ir-26), $Z^{1a}$ is preferably a group selected from the group consisting of groups represented by the formulae (III-1) to (III-13), more preferably a group selected from the group consisting of groups represented by the formulae (III-7) to (III-13).

In the formulae (Ir-1) to (Ir-26), the group $R^{Xa}$ represented by $R^{Za}$, $R^{Zb}$ or $R^{Zc}$ is preferably an alkyl group, a cycloalkyl group, an aryl group or a monovalent heterocyclic group, more preferably an alkyl group, a cycloalkyl group or an aryl group, and these groups optionally have a substituent.

In the formulae (Ir-1) to (Ir-26), the group $R^{Ya}$ represented by $R^{Za}$ is preferably an unsubstituted alkyl group or an unsubstituted cycloalkyl group.

In the formulae (Ir-1) to (Ir-26), the group $R^{Yb}$ represented by $R^{Zb}$ is preferably an aryl group, preferably an aryl group having an alkyl group as a substituent.

In the formulae (Ir-1) to (Ir-26), the group $R^{Yc}$ represented by $R^{Zc}$ is preferably an aryl group, preferably an aryl group having an alkyl group as a substituent.

Examples of the metal complex represented by the formula (1) or the formula (2) include metal complexes represented by the following formulae (Ir-101) to (Ir-122).
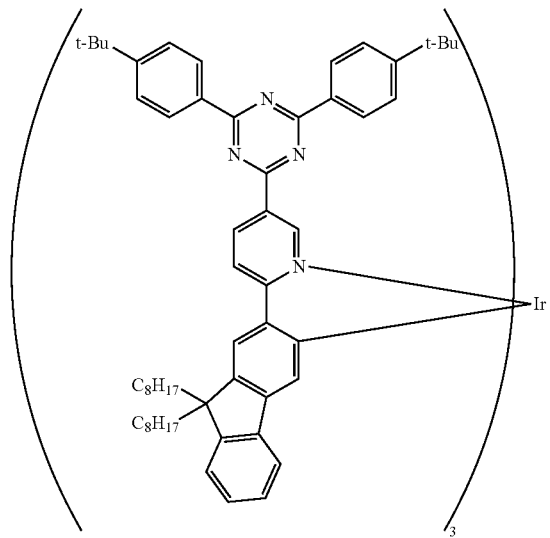
(Ir-101)
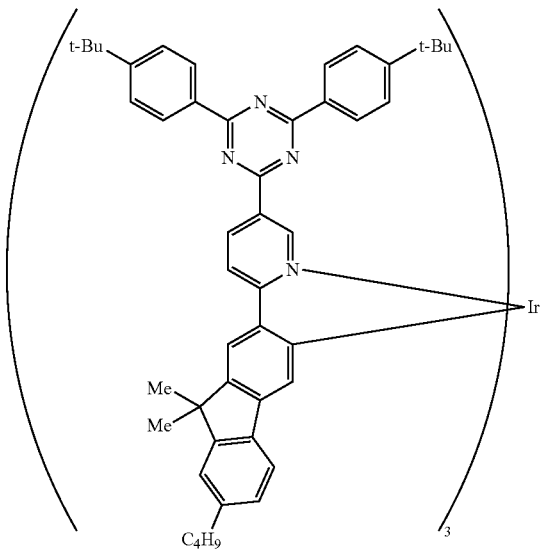
(Ir-102)
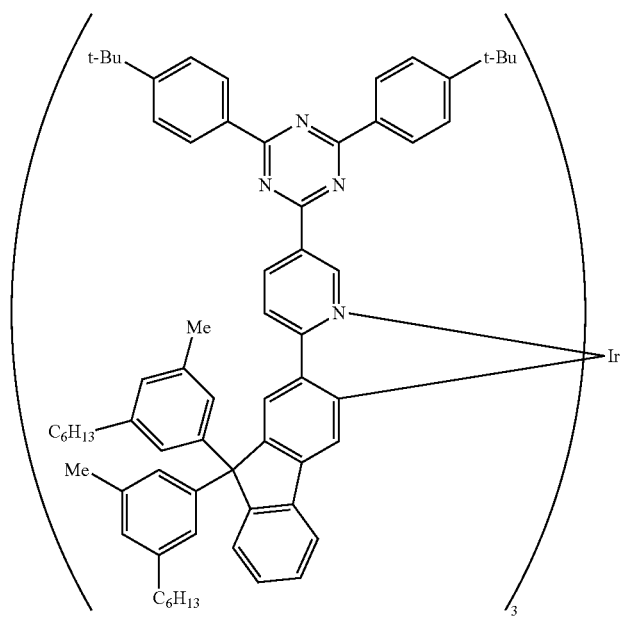
(Ir-103)

-continued
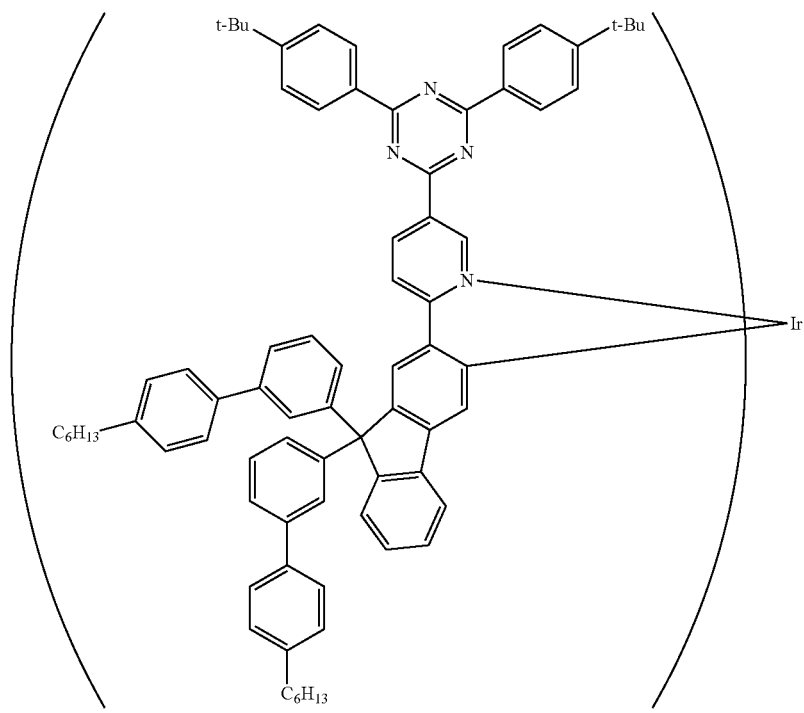
(Ir-104)
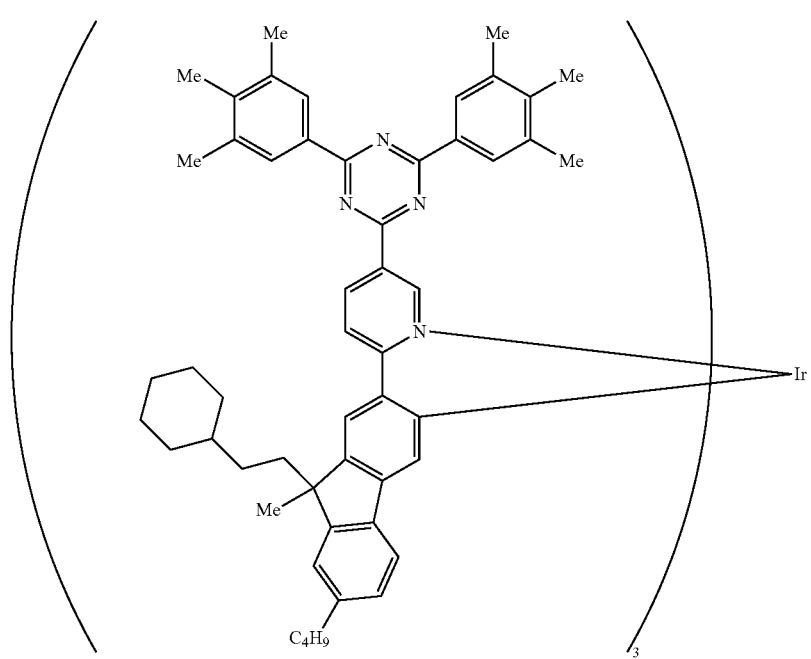
(Ir-105)

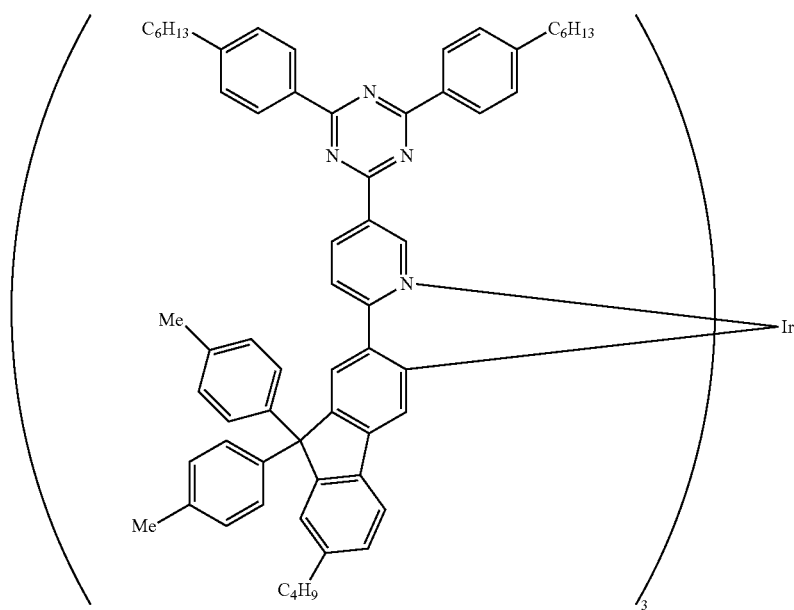
(Ir-106)
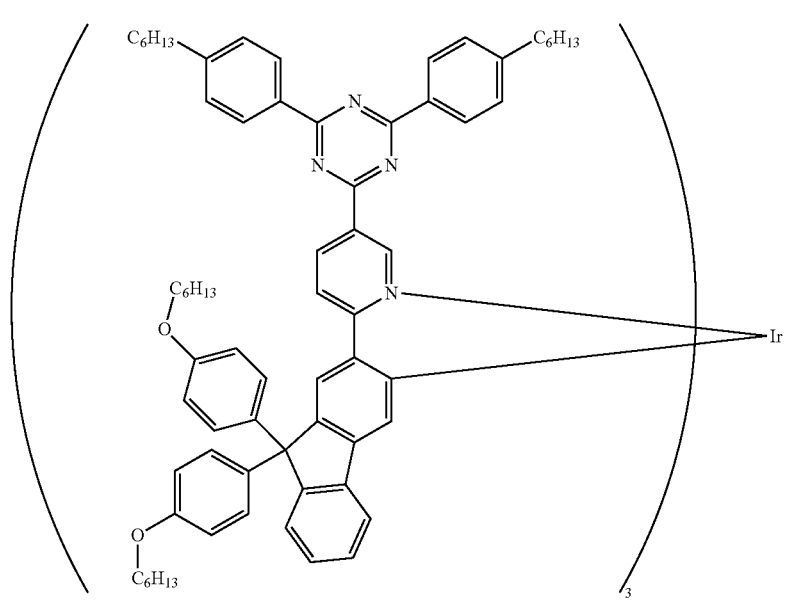
(Ir-107)

-continued
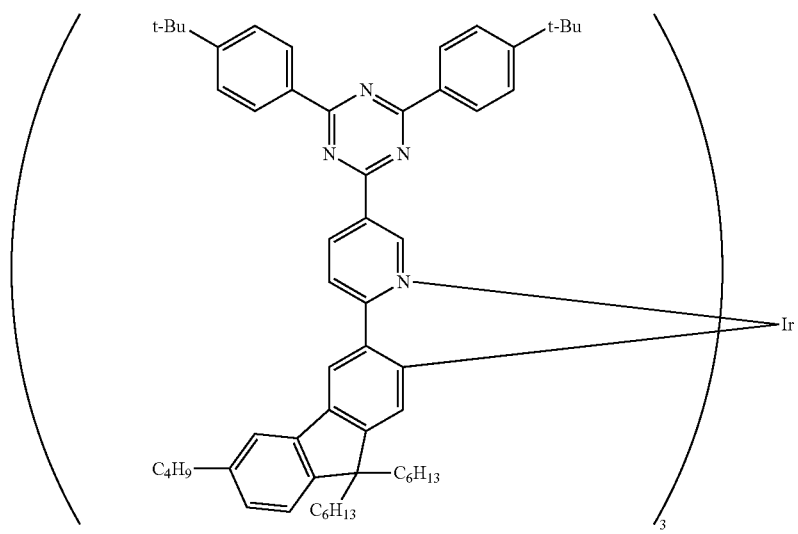
(Ir-108)
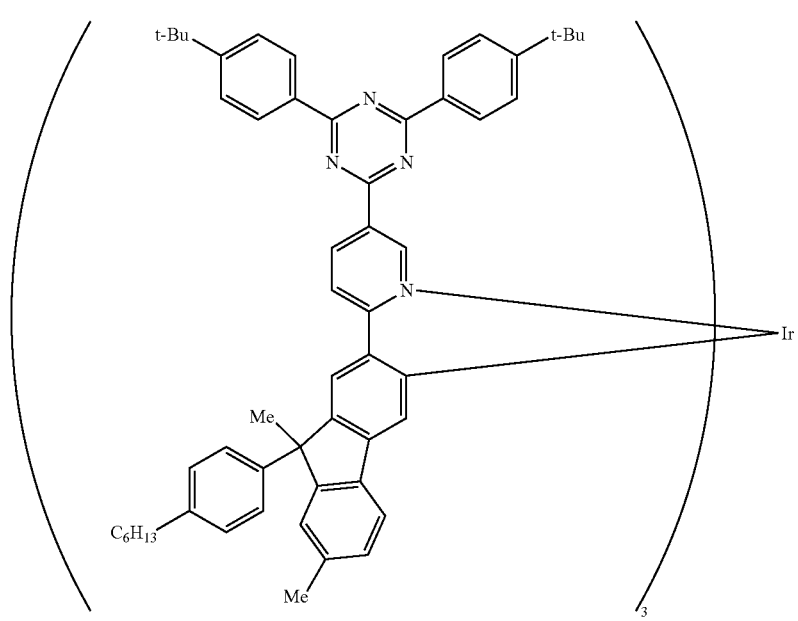
(Ir-109)

-continued
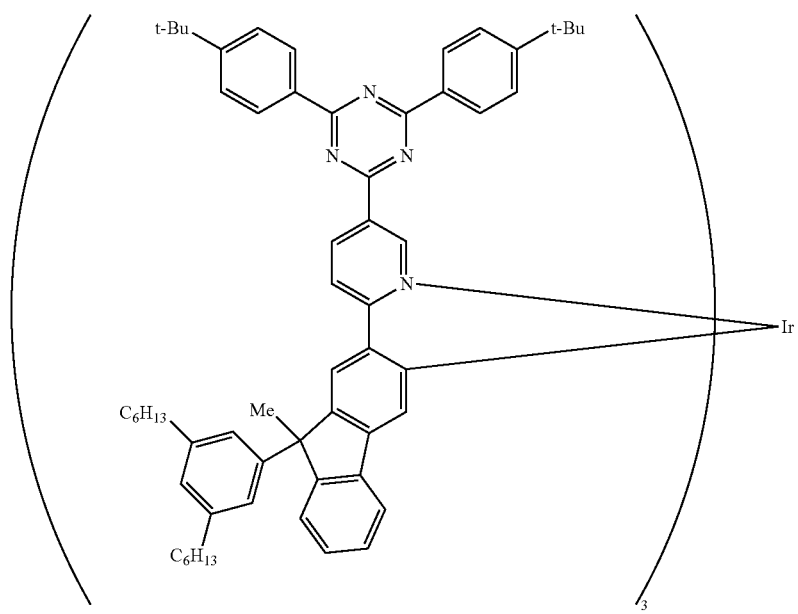
(Ir-110)
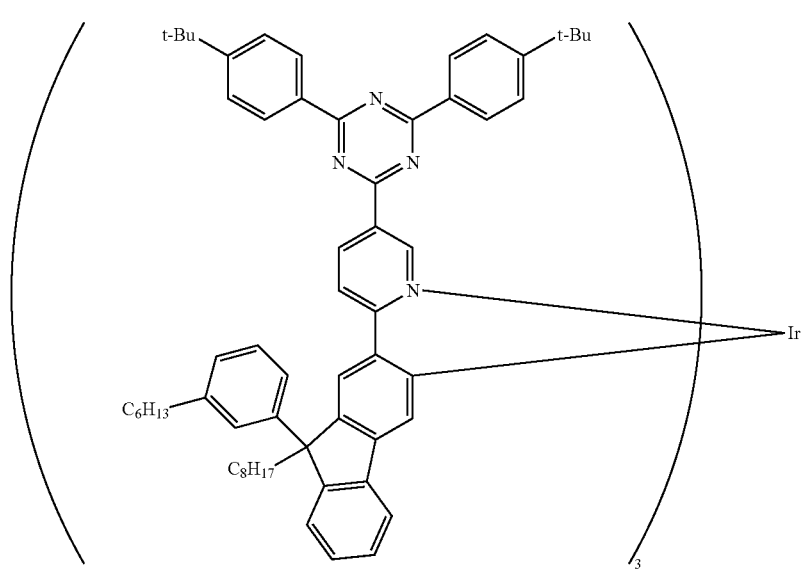
(Ir-111)

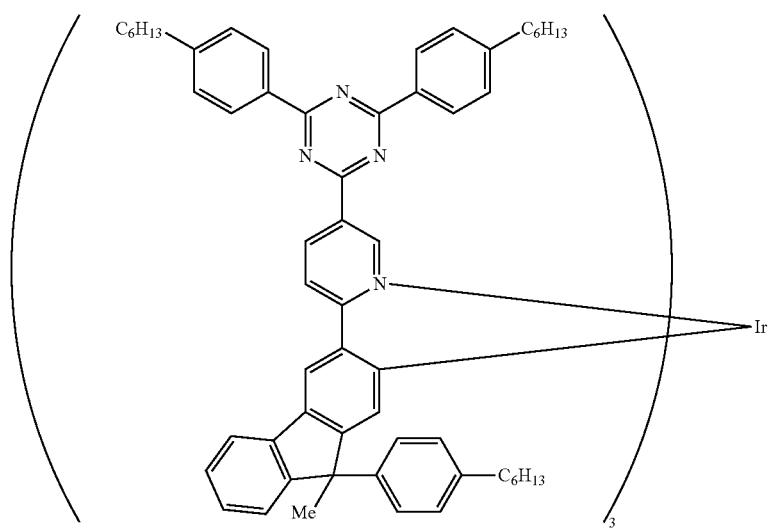
(Ir-112)
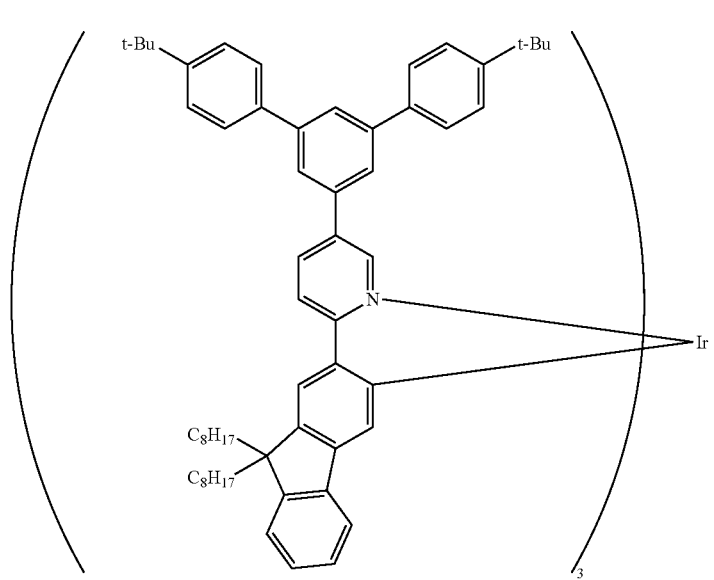
(Ir-113)

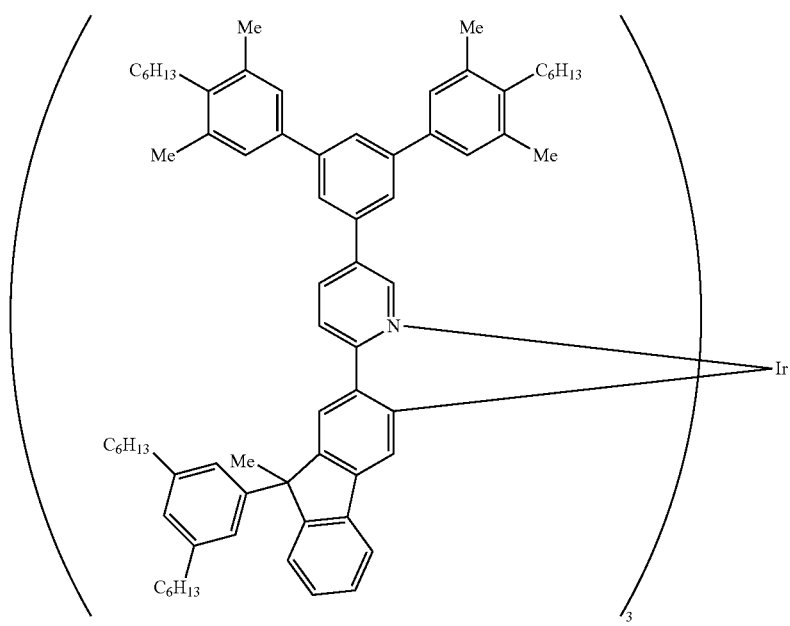
(Ir-114)
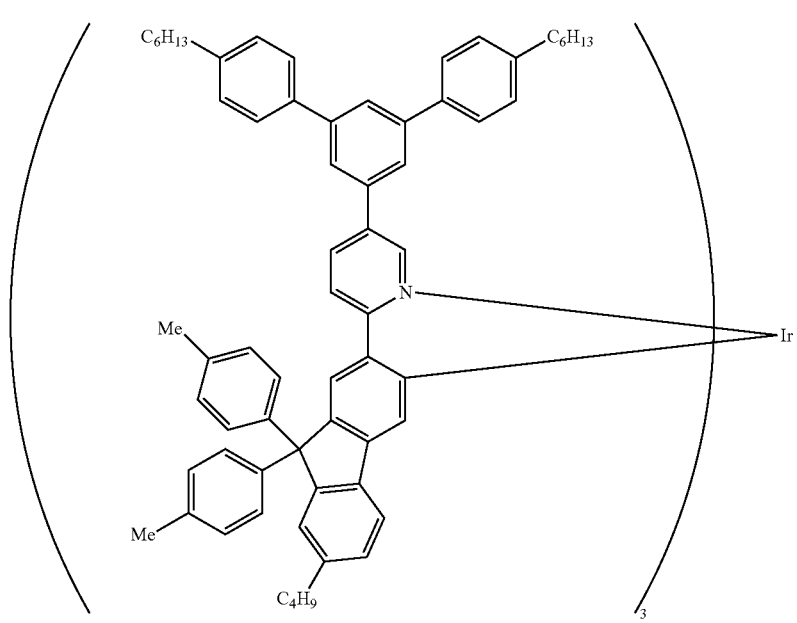
(Ir-115)

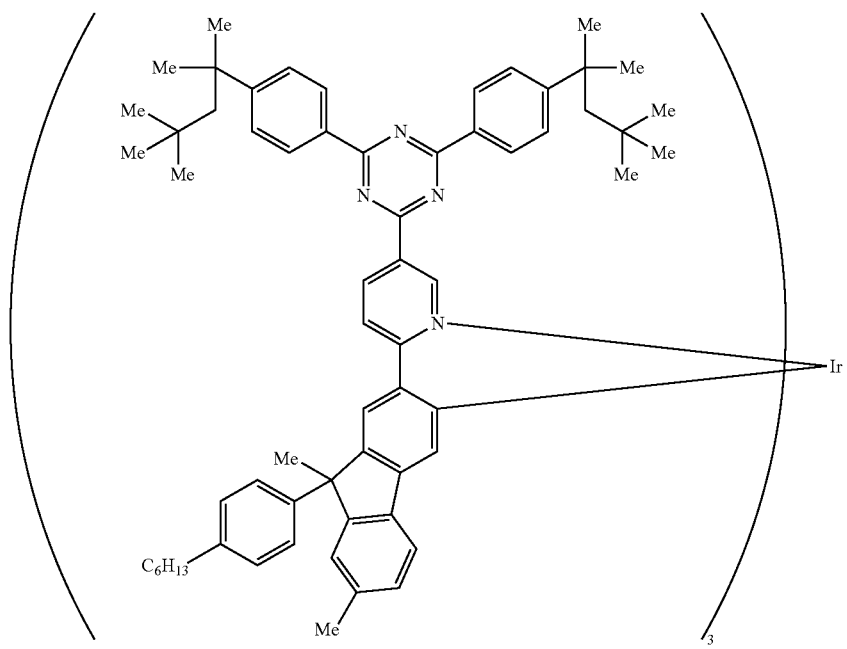
(Ir-116)
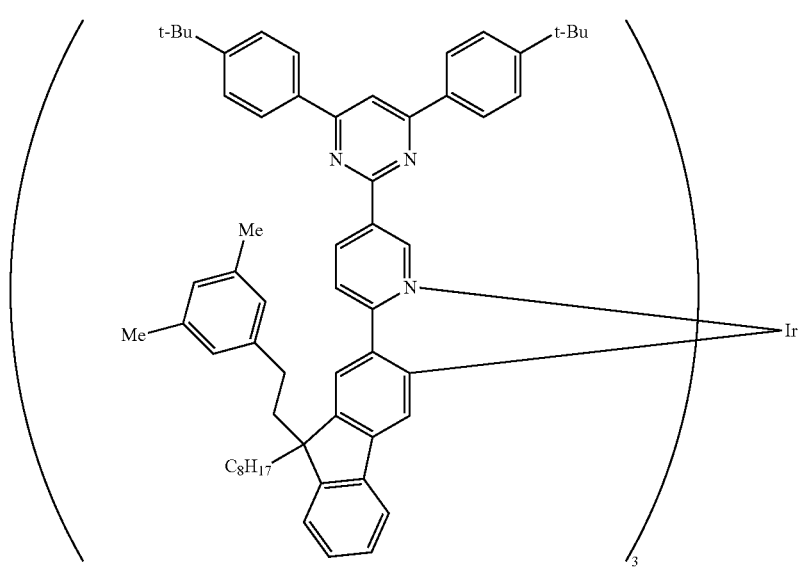
(Ir-117)

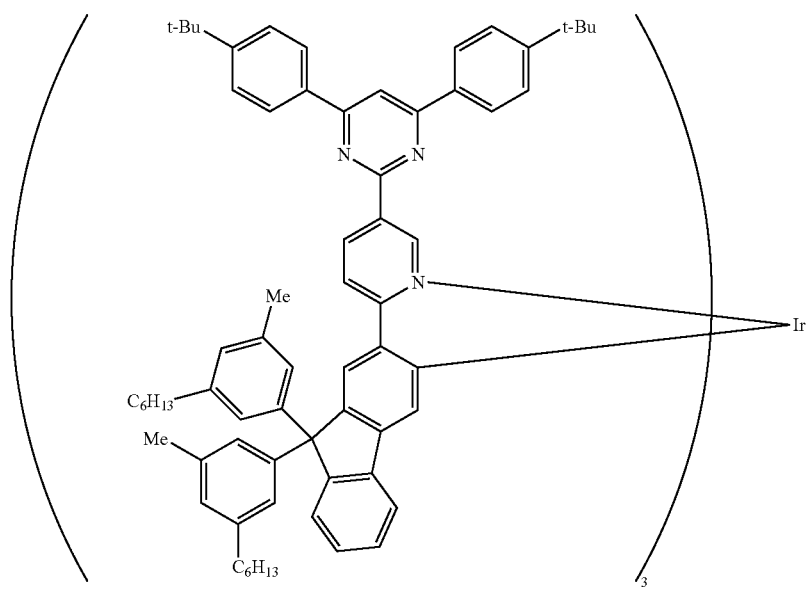
(Ir-118)
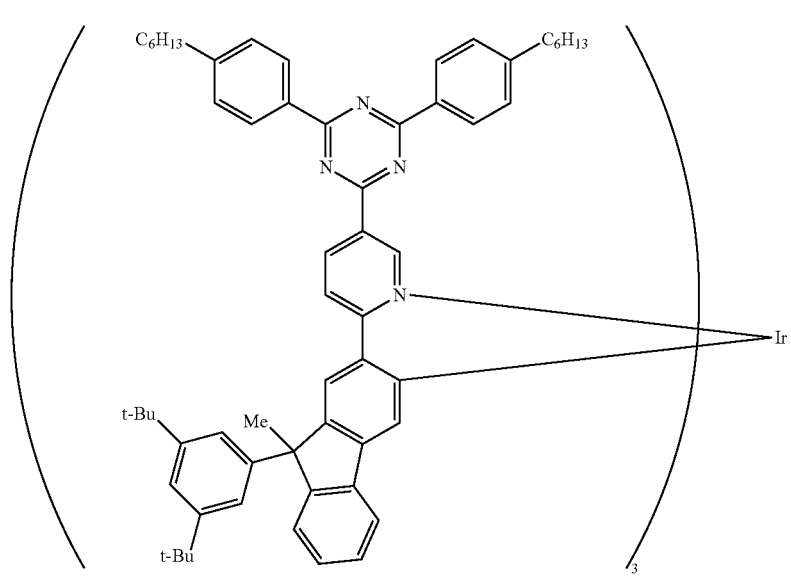
(Ir-119)

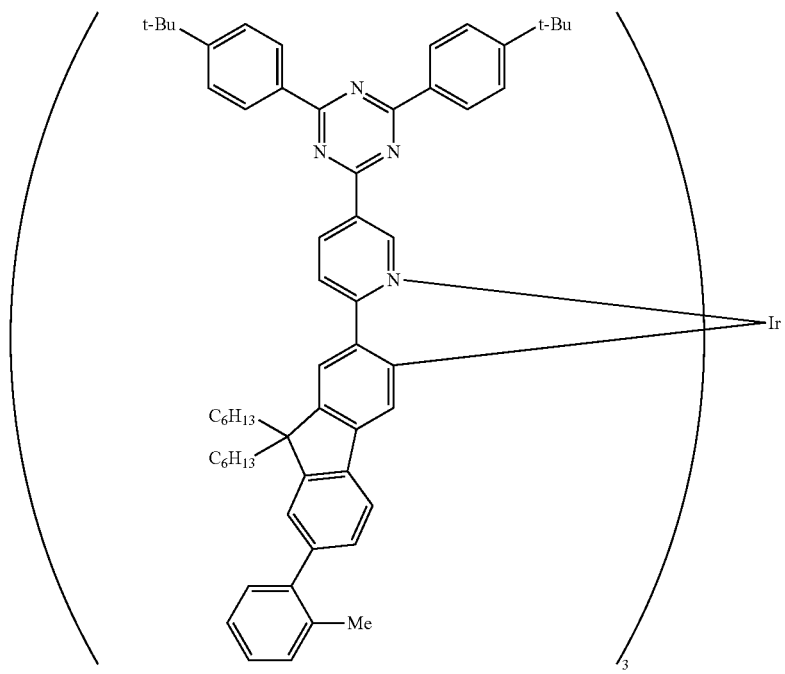
(Ir-120)
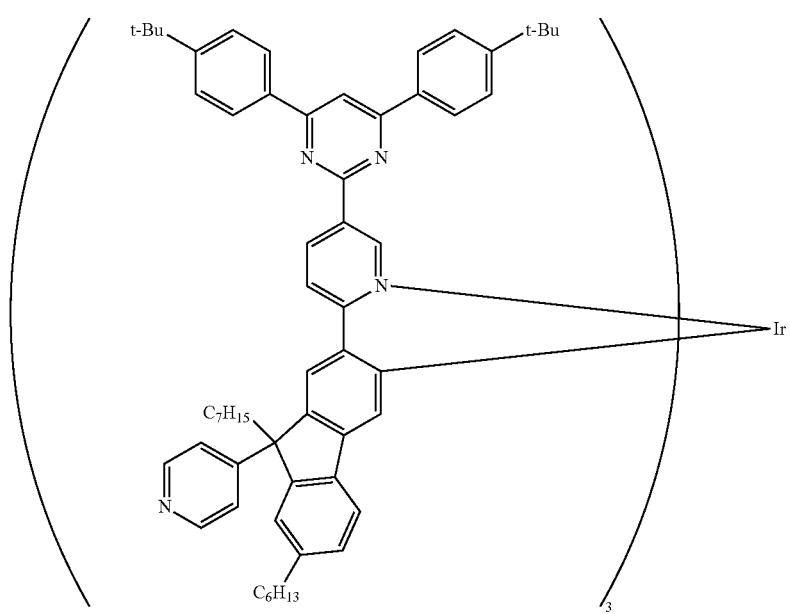
(Ir-121)

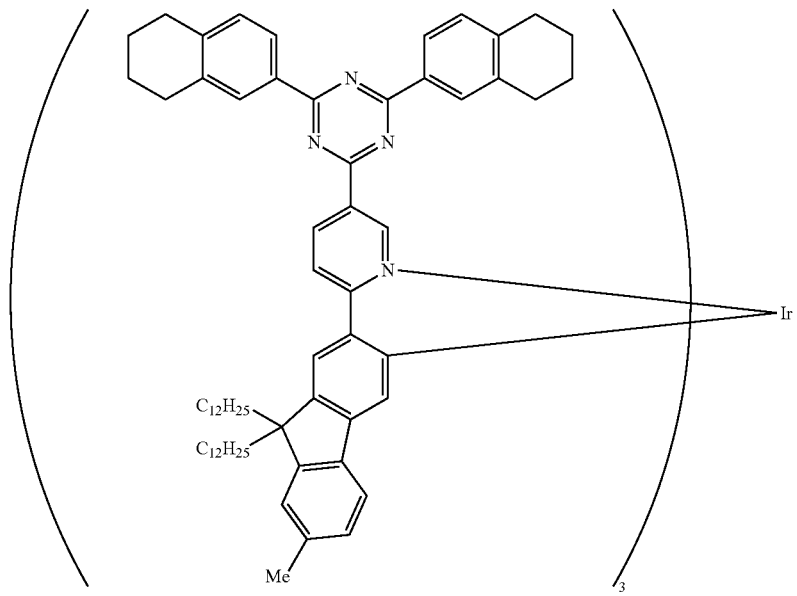

(Ir-122)

The metal complex represented by the formula (1) and the formula (2) can include a plurality of stereoisomers. The metal complex includes, for example, a metal complex having a ligand as an enantiomer, a metal complex having a ligand as a diastereomer, a metal complex which is totally a diastereomer owing to the presence of a plurality of ligands as an enantiomer, and the like.

Of the metal complexes represented by the formula (1) and the formula (2), the metal complex in which M is an iridium atom and $n_2$ is 0 can include stereoisomers as a facial isomer or a meridional isomer, and the proportion of the facial isomer with respect to the total metal complex is preferably 80% by mol or more, more preferably 90% by mol or more, further preferably 99% by mol or more, particularly preferably 100% by mol (that is, no meridional isomer is contained), since the full width at half maximum of the emission spectrum of the metal complex of the present invention is more excellent.

In a light emitting device produced using the metal complex of the present invention, the metal complexes of the present invention may be used singly or in combination of two or more.

<Production Method of Metal Complex Represented by Formula (1)>

[Production Method 1]

A metal complex represented by the formula (1) as the metal complex of the present invention can be produced, for example, by a method of reacting a metal compound and a compound as a ligand. If necessary, a reaction of exchanging functional groups of a ligand of the metal complex may be performed.

Of the metal complexes represented by the formula (1), the metal complex in which M is an iridium atom and n1 is 3 can be produced, for example, by a method comprising a step A1 of reacting a compound represented by the formula (M1-1) and an iridium compound or its hydrate to synthesize a metal complex represented by the formula (M1-2) and a step B1 of reacting the metal complex represented by the formula (M1-2) and the compound represented by the formula (M1-1) or a precursor of a ligand represented by $A^1$-$G^1$-$A^2$.

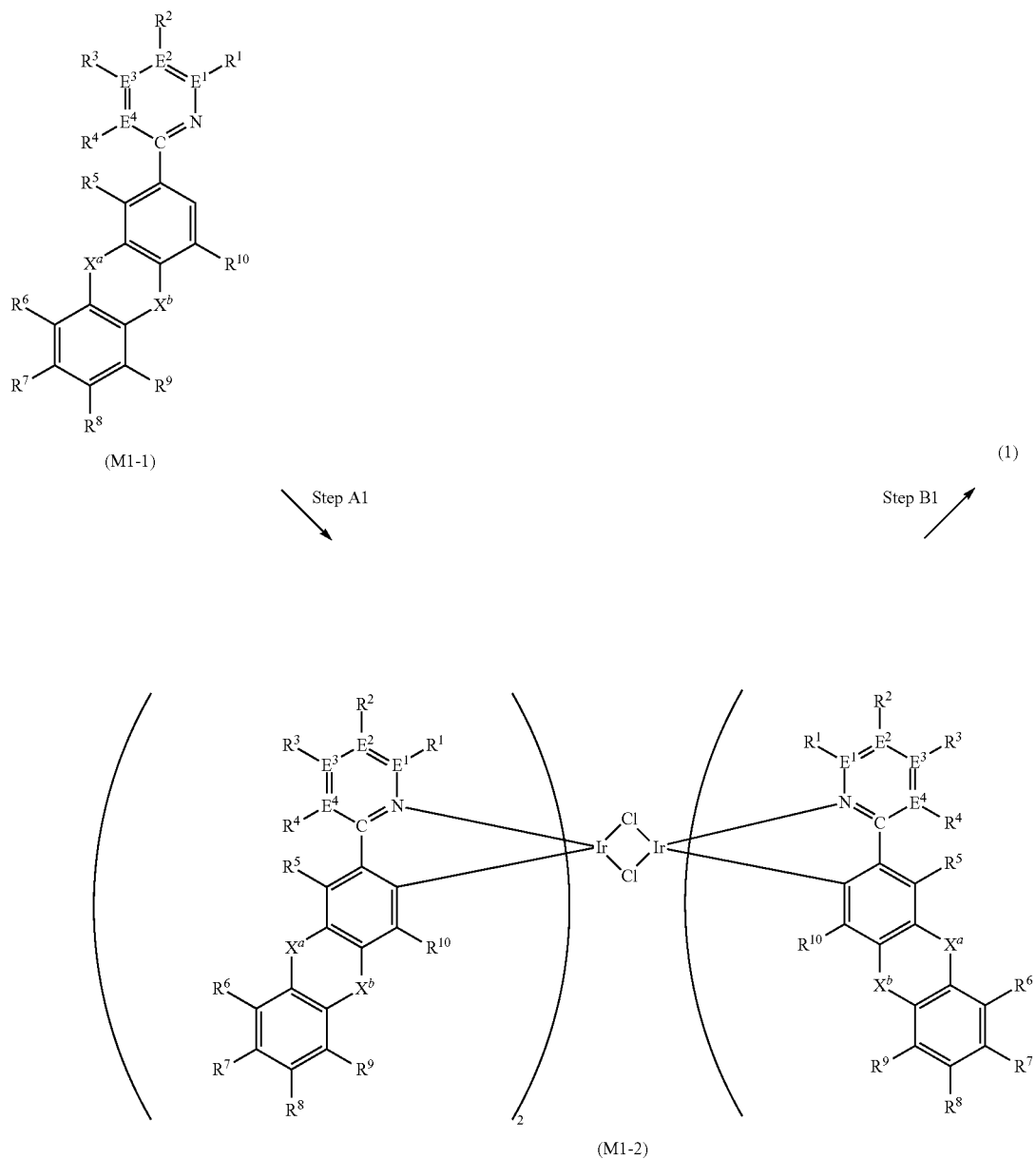

[wherein, $E^1$ to $E^4$, $R^1$ to $R^{10}$, $X^a$ and $X^b$ represent the same meaning as described above.]

In the step A1, the iridium compound includes, for example, iridium chloride, tris(acetylacetonato)iridium(III), chloro(cyclooctadiene)iridium(I) dimer and iridium(III) acetate, and the hydrate of the iridium compound includes, for example, iridium chloride.trihydrate.

The step A1 and the step B1 are usually conducted in a solvent. The solvent includes, for example, alcohol solvents such as methanol, ethanol, propanol, ethylene glycol, propylene glycol, glycerin, 2-methoxyethanol, 2-ethoxyethanol, 2-(2-ethoxyethoxy)ethanol, 2-(i-propoxy)ethanol, 2-(n-butoxy)ethanol, 2-(t-butoxy)ethanol and the like; ether solvents such as tetrahydrofuran, dioxane, cyclopentyl, methyl ether, diglyme and the like; halogen-based solvents such as methylene chloride, chloroform and the like; nitrile solvents such as acetonitrile, benzonitrile and the like; hydrocarbon solvents such as hexane, decalin, toluene, xylene, mesitylene and the like; amide solvents such as N,N-dimethylformamide, N,N-dimethylacetamide and the like; acetone, dimethyl sulfoxide, and water.

In the step A1 and the step B1, the reaction time is usually 30 minutes to 150 hours and the reaction temperature is usually between the melting point and the boiling point of a solvent present in the reaction system.

In the step A1, the amount of the compound represented by the formula (M1-1) is usually 2 to 20 mol with respect to 1 mol of the iridium compound or its hydrate.

In the step B1, the amount of the compound represented by the formula (M1-1) or the precursor of a ligand represented by $A^1$-$G^1$-$A^2$ is usually 1 to 100 mol with respect to 1 mol of the metal complex represented by the formula (M1-2).

In the step B1, the reaction is preferably conducted in the presence of a silver compound such as silver trifluoromethanesulfonate and the like. When a silver compound is used, its amount is usually 2 to 20 mol with respect to 1 mol of the metal complex represented by the formula (M1-2).

The compound represented by the formula (M1-1) can be synthesized, for example, by a step of conducting a coupling reaction such as the Suzuki reaction, the Kumada reaction, the Stille reaction and the like of a compound represented by the formula (M1-3) and a compound represented by the formula (M1-4)

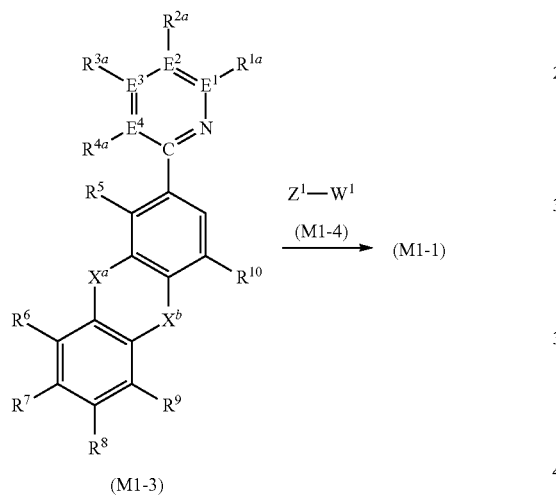

[wherein, $E^1$ to $E^4$, $R^5$ to $R^{10}$, $X^a$ and $X^b$ represent the same meaning as described above.

$Z^1$ represents a group represented by the above-described formula (D-A) or (D-B).

$W^1$ represents a group represented by —B(OR$^{W1}$)$_2$, an alkylsulfonyloxy group, a cycloalkylsulfonyloxy group, an arylsulfonyloxy group, a chlorine atom, a bromine atom or an iodine atom, and these groups optionally have a substituent.

$R^{1a}$, $R^{2a}$, $R^{3a}$ and $R^{4a}$ each independently represent a hydrogen atom, an alkyl group, a cycloalkyl group, an alkoxy group, a cycloalkoxy group, an aryl group, an aryloxy group, a monovalent heterocyclic group, a group represented by —B(OR$^{W1}$)$_2$, an alkylsulfonyloxy group, a cycloalkylsulfonyloxy group, an arylsulfonyloxy group, a chlorine atom, a bromine atom or an iodine atom, and these groups optionally have a substituent, $R^{1a}$ and $R^{2a}$, $R^{2a}$ and $R^{3a}$, $R^{3a}$ and $R^{4a}$, and $R^{4a}$ and $R^5$ each may be combined together to form a ring together with atoms to which they are attached. At least one selected from the group consisting of $R^{1a}$, $R^{2a}$, $R^{3a}$ and $R^{4a}$ is a group represented by —B(OR$^{W1}$)$_2$, an alkylsulfonyloxy group, a cycloalkylsulfonyloxy group, an arylsulfonyloxy group, a chlorine atom, a bromine atom or an iodine atom.

$R^{W1}$ represents a hydrogen atom, an alkyl group, a cycloalkyl group, an aryl group or an amino group, and these groups optionally have a substituent. A plurality of $R^{W1}$ may be the same or different, and may be combined together to form a ring structure together with oxygen atoms to which they are attached.]

The group represented by —B(OR$^{W1}$)$_2$ includes, for example, groups represented by the following formulae (W-1) to (W-10).

(W-1)

(W-2)

(W-3)

(W-4)

(W-5)

(W-6)

(W-7)

(W-8)

-continued

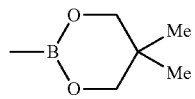
(W-9)

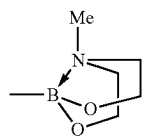
(W-10)

The alkylsulfonyloxy group represented by $W^1$ includes, for example, a methanesulfonyloxy group, an ethanesulfonyloxy group and a trifluoromethanesulfonyloxy group.

The arylsulfonyloxy group represented by $W^1$ includes, for example, a p-toluenesulfonyloxy group.

$W^1$ is preferably a group represented by $-B(OR^{W1})_2$, a trifluoromethanesulfonyloxy group, a chlorine atom, a bromine atom or an iodine atom since the coupling reaction of a compound represented by the formula (M1-3) and a compound represented by the formula (M1-4) progresses easily, and of them, a chlorine atom, a bromine atom or a group represented by the formula (W-7) is more preferable since synthesis of a compound represented by the formula (M1-4) is easy.

The alkylsulfonyloxy group, the cycloalkylsulfonyloxy group and the arylsulfonyloxy group represented by $R^{1a}$ to $R^{4a}$ represent the same meaning as the alkylsulfonyloxy group, the cycloalkylsulfonyloxy group and the arylsulfonyloxy group represented by $W^1$, respectively.

$R^{2a}$ is preferably a bromine atom, an iodine atom or a group represented by the formula (W-7).

$Z^1$ represents preferably a group represented by the formula (D-A), more preferably groups represented by the formula (P-A1) to the formula (D-A3).

The coupling reaction of a compound represented by the formula (M1-3) and a compound represented by the formula (M1-4) is usually conducted in a solvent. The solvent to be used, the reaction time and the reaction temperature are the same as those explained in the step A1 and the step B1.

In the coupling reaction of a compound represented by the formula (M1-3) and a compound represented by the formula (M1-4), the amount of the compound represented by the formula (M1-4) is usually 0.05 to 20 mol with respect to 1 mol of the compound represented by the formula (M1-3).

The compound represented by the formula (M1-4) includes, for example, compounds in which $Z^1$ is a group represented by the formulae (D-A1) to (D-A3) and $W^1$ is a group represented by $-B(OR^{W1})_2$, a trifluoromethanesulfonyloxy group, a chlorine atom, a bromine atom or an iodine atom.

A compound represented by the formula (M1-4-1) as one embodiment of the compound represented by the formula (M1-4) can be synthesized, for example, by the following method.

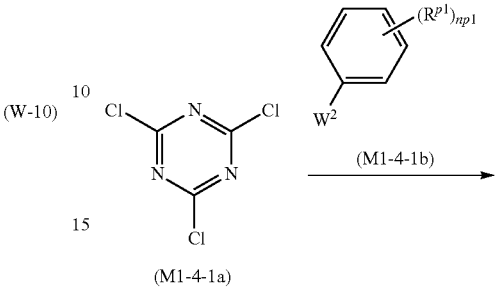

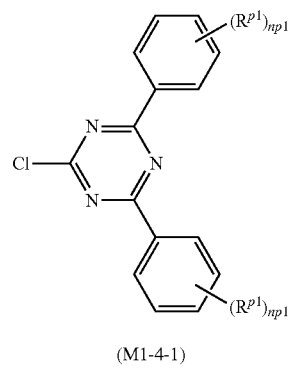

[wherein, $R^{p1}$ and np1 represent the same meaning as described above.

$W^2$ represents a group represented by $-B(OR^{W1})_2$, an alkylsulfonyloxy group, a cycloalkylsulfonyloxy group, an arylsulfonyloxy group, a chlorine atom, a bromine atom or an iodine atom, and these groups optionally have a substituent.]

The compound represented by the formula (M1-4-1) can be produced, for example, by conducting a coupling reaction of a compound represented by the formula (M1-4-1a) and a compound represented by the formula (M1-4-1b). This coupling reaction is the same as that explained for the compound represented by the formula (M1-1).

A compound represented by the formula (M1-4-2) as one embodiment of the compound represented by the formula (M1-4) can be synthesized, for example, by the following method.

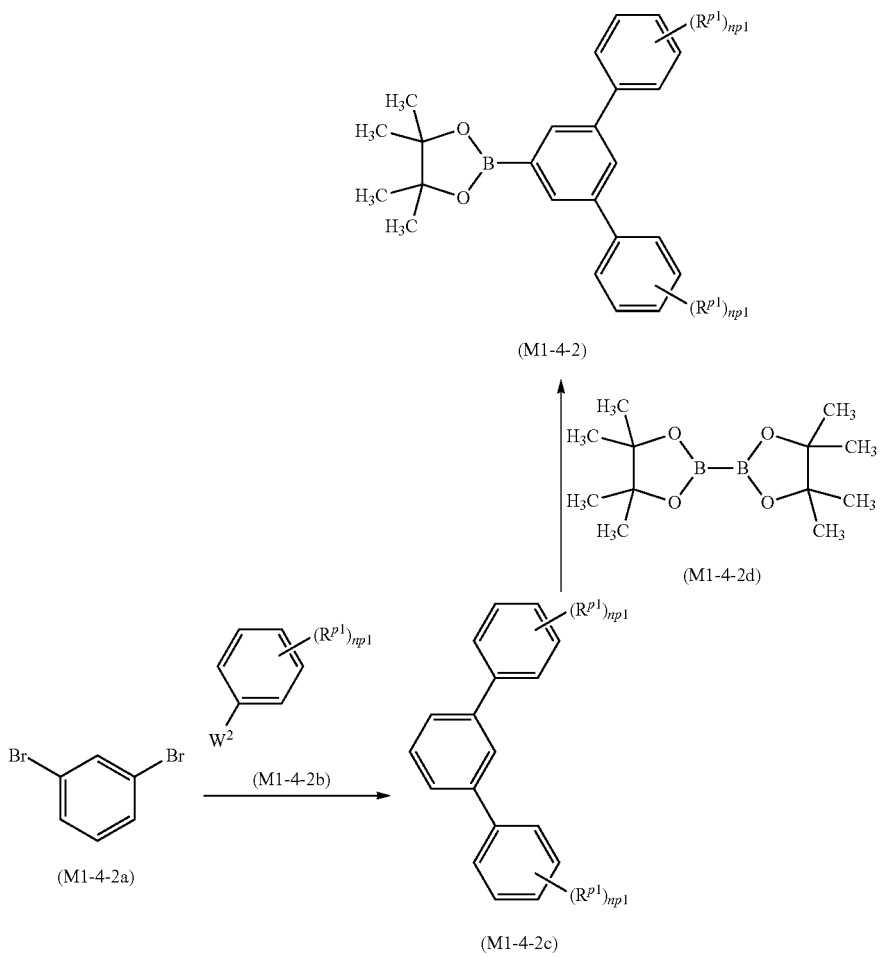

(M1-4-2)

(M1-4-2d)

(M1-4-2b)

(M1-4-2a)

(M1-4-2c)

[wherein, $R^{p1}$, np1 and $W^2$ represent the same meaning as described above.]

A compound represented by the formula (M1-4-2c) can be produced, for example, by conducting a coupling reaction of a compound represented by the formula (M1-4-2a) and a compound represented by the formula (M1-4-2b). This coupling reaction is the same as that explained for the compound represented by the formula (M1-1).

The compound represented by the formula (M1-4-2) can be synthesized, for example, by conducting the Ishiyama-Miyaura-Hartwig reaction of the compound represented by the formula (M1-4-2c) and a compound represented by the formula (M1-4-2d).

A compound represented by the formula (M1-3) can be produced, for example, by conducting a coupling reaction of a compound represented by the formula (M1-5) and a compound represented by the formula (M1-6). This coupling reaction is the same as that explained for the compound represented by the formula (M1-1).

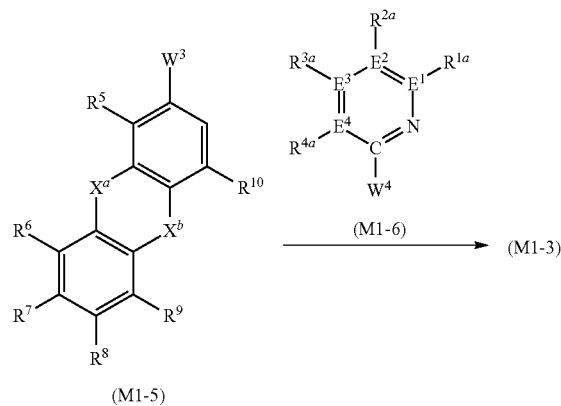

(M1-5)

(M1-6)  →  (M1-3)

[wherein,
$E^1$ to $E^4$, $R^5$ to $R^{10}$, $R^{1a}$ to $R^{4a}$, $X^a$ and $X^b$ represent the same meaning as described above.

$W^3$ and $W^4$ each independently represent a group represented by $-B(OR^{W1})_2$, an alkylsulfonyloxy group, a cycloalkylsulfonyloxy group, an arylsulfonyloxy group, a chlorine atom, a bromine atom or an iodine atom, and these groups optionally have a substituent.]

[Production Method 2]

A metal complex represented by the formula (1) as the metal complex of the present invention can also be produced, for example, by a method of reacting a precursor of a metal complex and a precursor of a ligand of a metal complex.

The metal complex represented by the formula (1) can be produced, for example, by conducting a coupling reaction of the compound represented by the formula (M1-4) described above and a metal complex represented by the formula (M1-7). This coupling reaction is the same as that explained for the compound represented by the formula (M1-1).

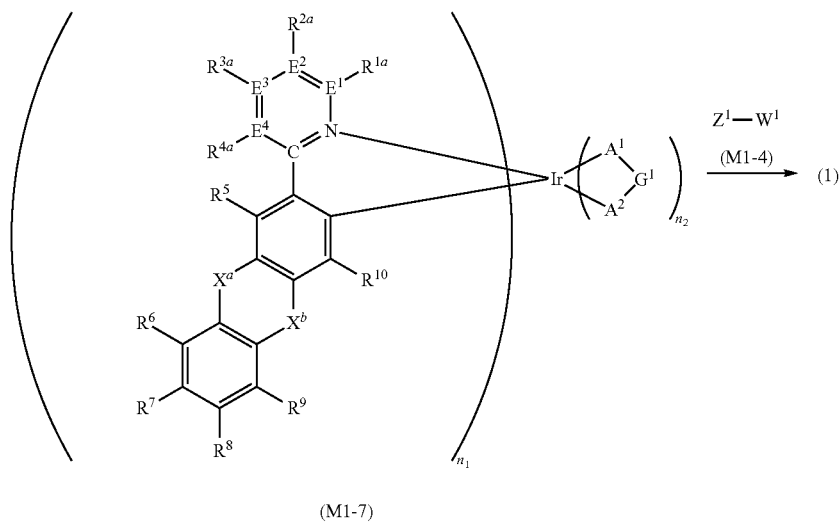

(M1-7)

[wherein, $R^5$ to $R^{10}$, $R^{1a}$ to $R^{4a}$, $E^1$ to $E^4$, $n_1$, $n_2$, $X^a$, $X^b$ and $A_1$-$G_1$-$A^2$ represent the same meaning as described above.]

The metal complex represented by the formula (M1-7) can be synthesized, for example, by using a compound represented by the above-described formula (M1-3) instead of the compound represented by the formula (M1-1) in the step A1 and the step B1 in [Production method 1] of the metal complex represented by the formula (1) described above.

<Production Method of Metal Complex Represented by Formula (2)>

[Production Method 3]

A metal complex represented by the formula (2) as the metal complex of the present invention can be produced, for example, by the same method as in [Production method 1] of the metal complex represented by the formula (1) described above.

Specifically, it can be produced by a method comprising a step A2 of synthesizing a metal complex represented by the formula (M22) by using a compound represented by the formula (M2-1) instead of the compound represented by the formula (M1-1) in [Production method 1] of the metal complex represented by the formula (1) described above and a step B2 of reacting the metal complex represented by the formula (M2-2) and the compound represented by the formula (M2-1) or a precursor of a ligand represented by $A^1$-$G^1$-$A^2$. The step A2 and the step B2 can be carried out by the same methods as for the step A1 and the step B1 in [Production method 1] of the metal complex represented by the formula (1) described above, respectively.

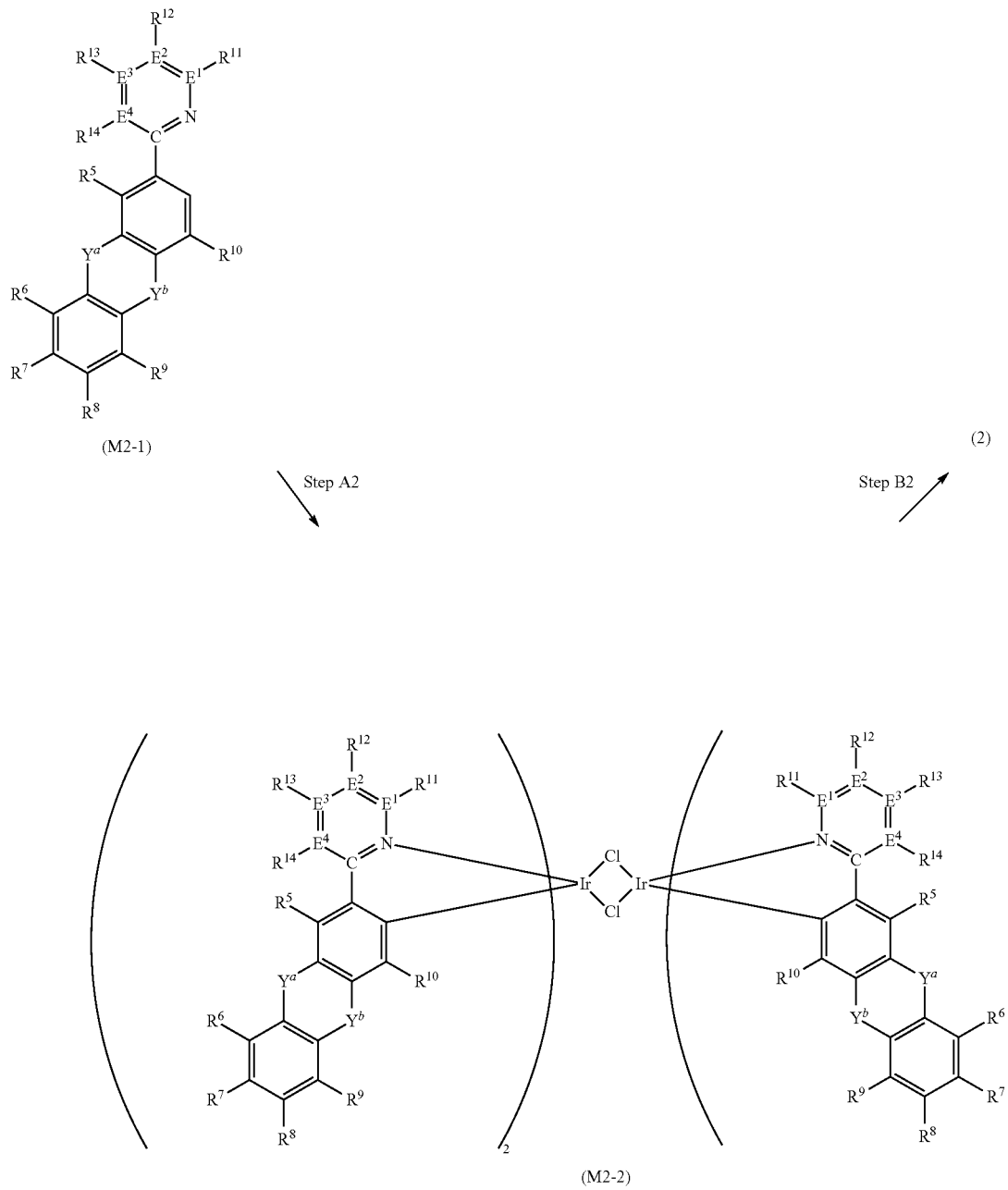

[wherein, $E^1$ to $E^4$, $R^5$ to $R^{14}$, $Y^a$ and $Y^b$ represent the same meaning as described above.]

When at least one selected from the group consisting of $R^{11}$, $R^{12}$, $R^{13}$ and $R^{14}$ is a group represented by the above-described formula (D-A) or (D-B) in the compound represented by the formula (M2-1), this can be synthesized, for example, by using a compound the formula (M2-3) instead of the compound represented by the formula (M1-3) in [Production method 1] of the metal complex represented by the formula (1) described above.

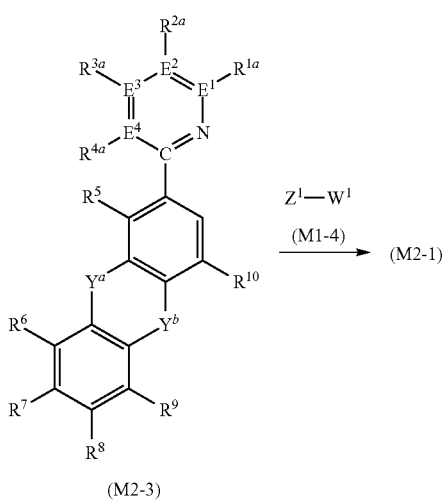

(M2-3)

[wherein, $E^1$ to $E^4$, $R^5$ to $R^{10}$, $R^{1a}$ to $R^{4a}$, $Y^a$, $Y^b$, $Z^1$ and $W^1$ represent the same meaning as described above.]

[wherein, $E^1$ to $E^4$, $R^5$ to $R^{10}$, $R^{1a}$ to $R^{4a}$, $Y^a$, $Y^b$, $W^3$ and $W^4$ represent the same meaning as described above.]

[Production Method 4]

A metal complex represented by the formula (2) as the metal complex of the present invention can be produced, for example, by the same method as in [Production method 2] of the metal complex represented by the formula (1) described above.

Specifically, it can be produced by using a compound represented by the formula (M2-7) instead of the compound represented by the formula (M1-7) in [Production method 2] of the metal complex represented by the formula (1) described above. This reaction can be carried out by the same method as for the reaction in [Production method 2] of the metal complex represented by the formula (1) described above.

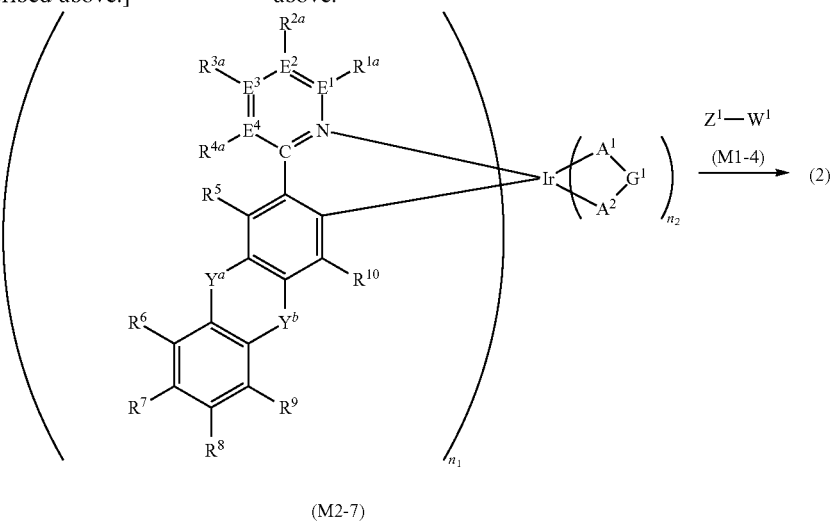

(M2-7)

The compound represented by the formula (M2-3) can be synthesized, for example, by using a compound represented by the formula (M2-5) instead of the compound represented by the formula (M1-5) in [Production method 1] of the metal complex represented by the formula (1) described above.

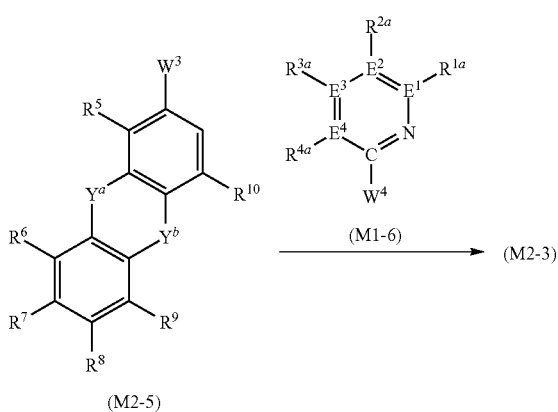

(M2-5)

[wherein, $R^5$ to $R^{10}$, $R^{1a}$ to $R^{4a}$, $E^1$ to $E^4$, $n_1$, $n_2$, $Y^a$, $Y^b$ and $A^1$-$G^1$-$A^2$ represent the same meaning as described above.]

[Coupling Reaction in Production Method 1, Production Method 2, Production Method 3 and Production Method 4]

In the coupling reaction, catalysts such as a palladium catalyst and the like may be used for promoting the reaction. The palladium catalyst includes, for example, palladium acetate, bis(triphenylphosphine)palladium(II) dichloride, tetrakis(triphenylphosphine)palladium(0), [1,1'-bis(diphenylphosphino)ferrocene]dichloropalladium(II) and tris(dibenzylideneacetone)dipalladium(0).

The palladium catalyst may also be used together with a phosphorus compound such as triphenylphosphine, tri(o-tolyl)phosphine, tri(tert-butyl)phosphine, tricyclohexylphosphine, 1,1'-bis(diphenylphosphino)ferrocene and the like.

When the palladium catalyst is used in the coupling reaction, its amount is, for example, usually an effective amount with respect to 1 mol of a compound represented by the formula (M1-3), the formula (M1-4), the formula (M1-5), the formula (M1-7), the formula (M2-3), the formula (M2-5) or the formula (M2-7), and preferably 0.00001 to 10 mol in terms of a palladium element.

In the coupling reaction, a base may be used together, if necessary.

For the compounds, the catalysts and the solvents used in the reactions explained in <Production method of metal complex>, each of them may be used singly or in combination of two or more.

<Metal-containing Polymer Compound>

A polymer compound containing a constitutional unit having a group derived from a metal complex represented by the formula (1) or (2) described above (hereinafter, also referred to as "metal-containing constitutional unit") (hereinafter, also referred to as "metal-containing polymer compound") performs an equivalent effect to the metal complex of the present invention.

The metal-containing constitutional unit includes, for example, an arylene group or a divalent heterocyclic group having as a substituent a group obtained by removing one hydrogen atom from a metal complex represented by the formula (1) or (2) described above, a group obtained by removing one hydrogen atom from a metal complex represented by the formula (1) or (2) described above, a group obtained by removing two hydrogen atoms from a metal complex represented by the formula (1) or (2) described above, and a group obtained by removing three hydrogen atoms from a metal complex represented by the formula (1) or (2) described above.

When the metal-containing polymer compound contains as a constitutional unit a group obtained by removing one hydrogen atom from a metal complex represented by the formula (1) or (2) described above, the constitutional unit is usually an end constitutional unit. When the metal-containing polymer compound contains as a metal-containing constitutional unit a group obtained by removing three hydrogen atoms from a metal complex represented by the formula (1) or (2) described above, the metal-containing polymer compound is branched at a position of the metal-containing constitutional unit.

The metal-containing constitutional unit includes, for example, constitutional units represented by the following formulae (3a) to (3h), and constitutional units represented by the formula (3b), (3c), (3e), (3f) or (3h) are preferable, constitutional units represented by the formula (3c), (3f) or (3h) are more preferable, constitutional units represented by the formula (3f) or (3h) are further preferable, since synthesis of the metal-containing polymer compound is easy.

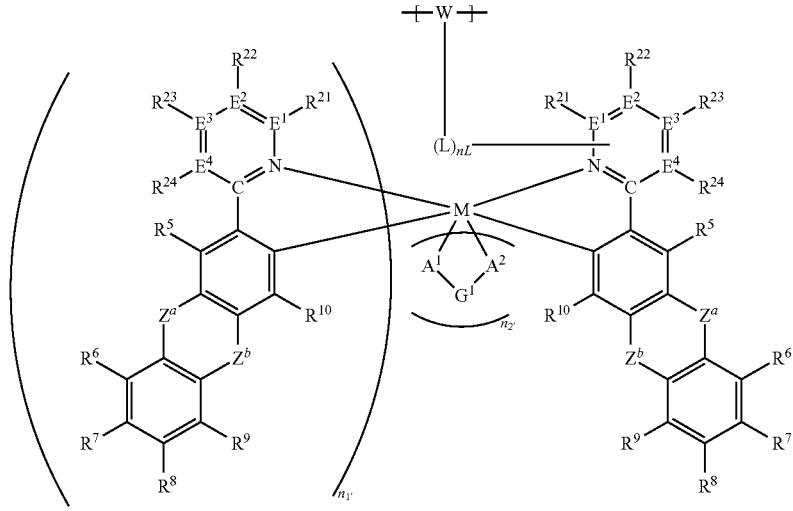

(3a)

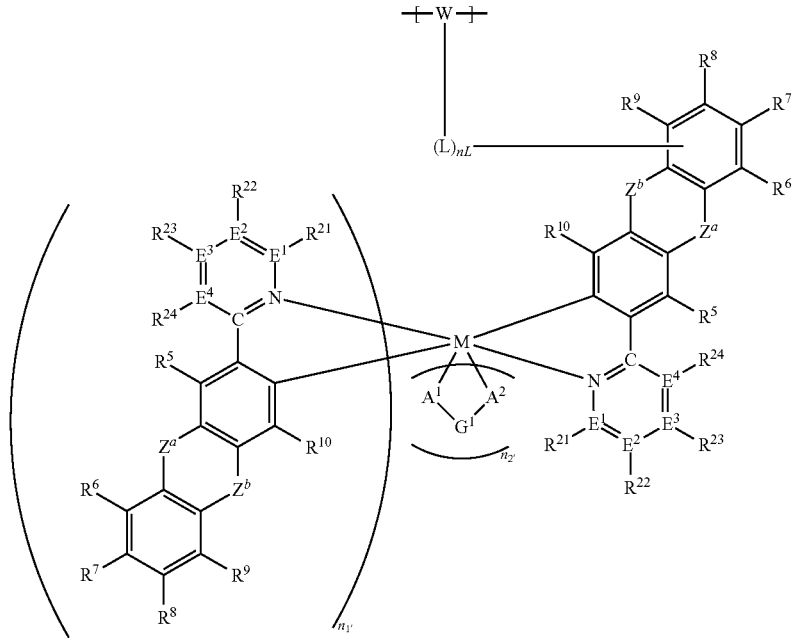

(3b)

-continued
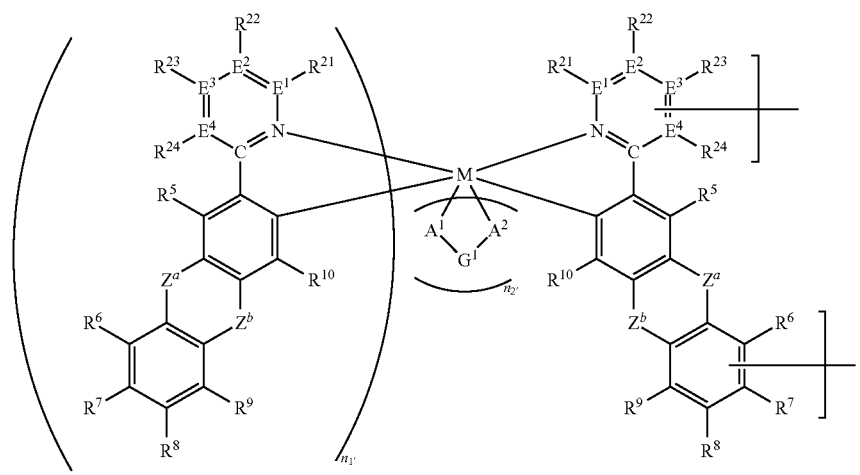
(3c)
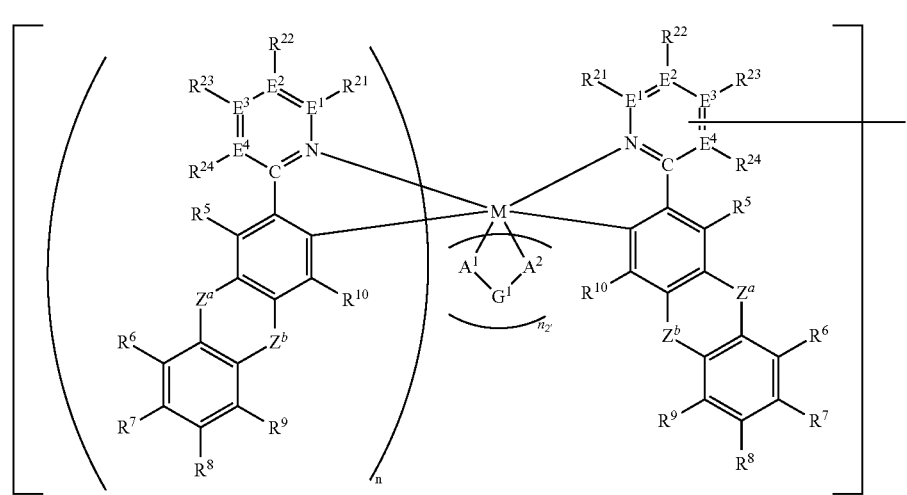
(3d)
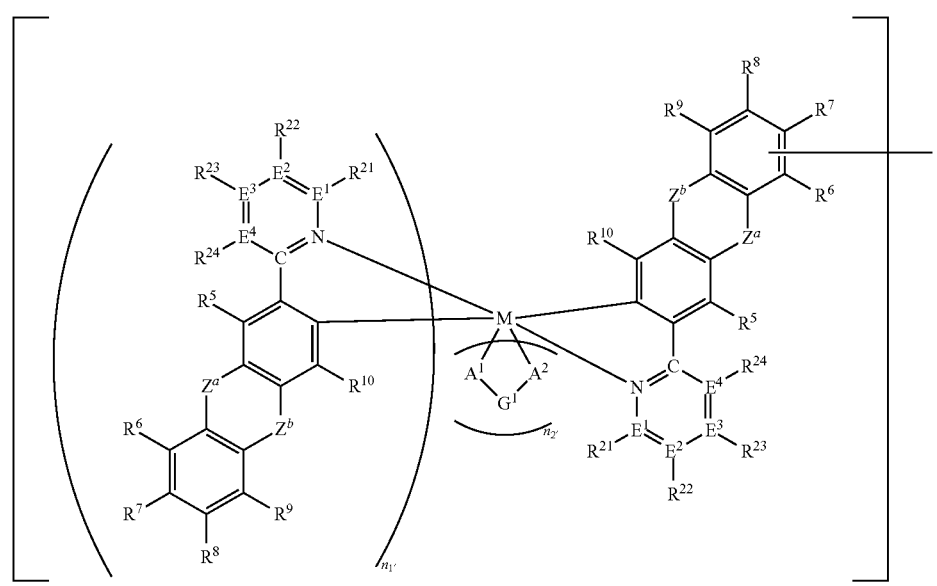
(3e)

(3f)
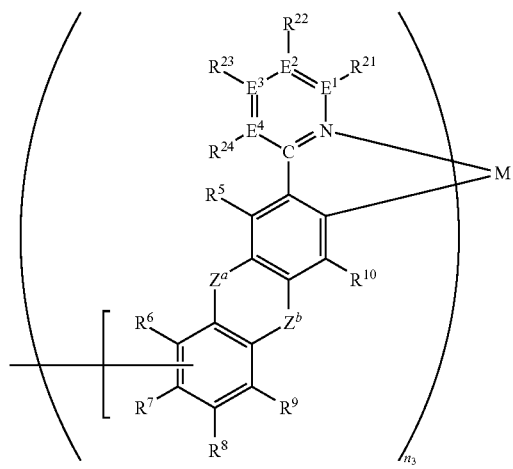
(3g)
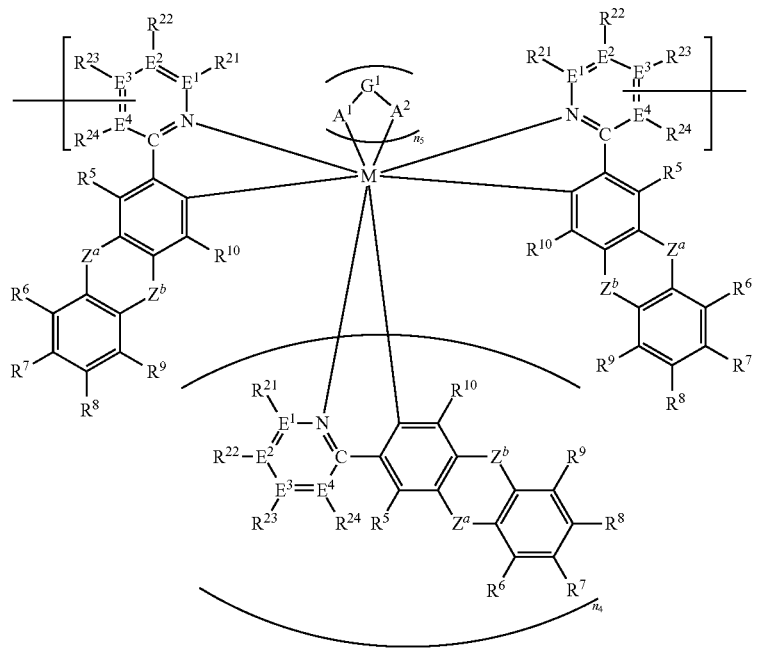

-continued (3h)

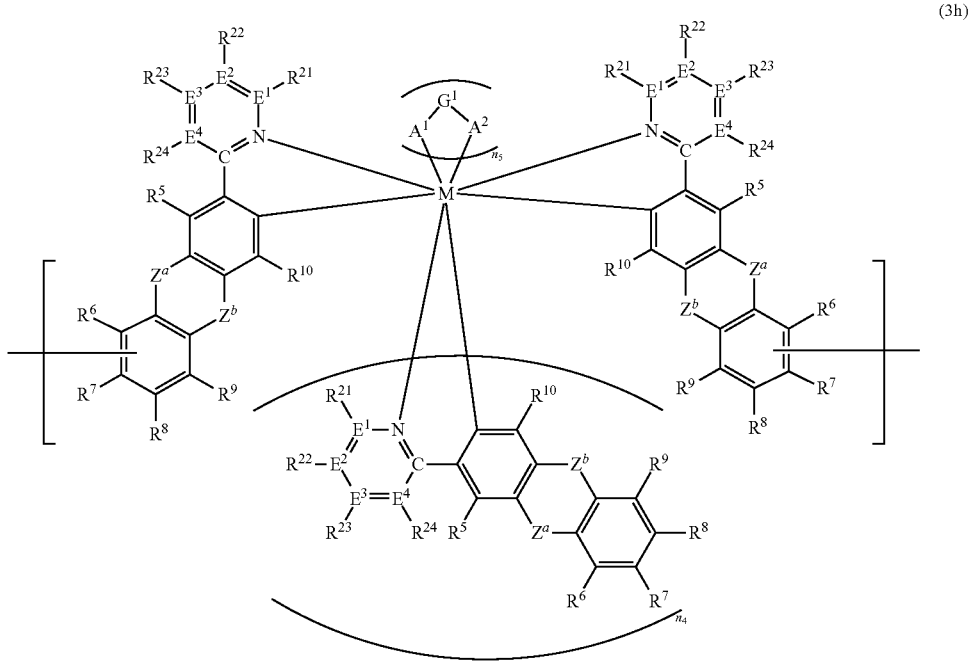

[wherein,

M, $E^1$, $E^2$, $E^3$, $E^4$, $R^5$, $R^6$, $R^7$, $R^8$, $R^9$, $R^{10}$ and $A^1$-$G^1$-$A^2$ represent the same meaning as described above. When $E^1$ is a nitrogen atom, $R^{21}$ is not present, when $E^2$ is a nitrogen atom, $R^{22}$ is not present, when $E^3$ is a nitrogen atom, $R^{23}$ is not present, and when $E^4$ is a nitrogen atom, $R^{24}$ is not present.

$n_1'$ represents 0, 1 or 2. $n_2'$ represents 0, 1 or 2. $n_1'+n_2'$ is 2 when M is an iridium atom, and $n_1'+n_2'$ is 1 when M is a platinum atom.

$n_3$ represents 2 or 3. $n_3$ is 3 when N is an iridium atom and $n_3$ is 2 when M is a platinum atom.

$n_4$ represents 0 or 1. $n_5$ represents 0 or 1. $n_4+n_5$ is 1 when M is an iridium atom and $n_4+n_5$ is 0 when N is a platinum atom.

$R^{21}$, $R^{22}$, $R^{23}$ and $R^{24}$ each independently represent a hydrogen atom, an alkyl group, a cycloalkyl group, an alkoxy group, a cycloalkoxy group, an aryl group, an aryloxy group, a monovalent heterocyclic group or a halogen atom, and these groups optionally have a substituent. When a plurality of $R^{21}$, $R^{22}$, $R^{23}$ and $R^{24}$ are present, they may be the same or different at each occurrence. $R^{21}$ and $R^{22}$, $R^{22}$ and $R^{23}$, $R^{23}$ and $R^{24}$, and $R^{24}$ and $R^5$ each may be combined together to form a ring together with atoms to which they are attached.

$Z^a$ and $Z^b$ each independently represent a direct bond, an oxygen atom, a sulfur atom, —C(=O)—, —$CR^{Za}R^{Zb}$—, —$CR^{Zc}_2$— or —$NR^{Zc}$—. $R^{Za}$ represents an alkyl group or a cycloalkyl group, and these groups optionally have an aryl group or a monovalent heterocyclic group as a substituent. $R^{Zb}$ represents an aryl group or a monovalent heterocyclic group, and these groups optionally have a substituent. $R^{Zc}$ represents a hydrogen atom, an alkyl group, a cycloalkyl group, an aryl group or a monovalent heterocyclic group, and these groups optionally have a substituent. When a plurality of $R^{Zc}$ are present, they may be the same or different and may be combined together to form a ring together with carbon atoms to which they are attached.

When a plurality of $Z^a$ and $Z^b$ are present, they may be the same or different at each occurrence. At least one of $Z^a$ and $Z^b$ is an oxygen atom, a sulfur atom, —C(=O)—, —$CR^{Za}R^{Zb}$—, —$CR^{Zc}_2$— or —$NR^{Zc}$—.

At least one selected from the group consisting of $R^{21}$, $R^{22}$, $R^{23}$ and $R^{24}$ is a group represented by the formula (D-A) or (D-B) described above, or at least one of $Z^a$ and $Z^b$ is $CR^{Za}R^{Zb}$—.

W represents a group represented by the following formula (W1), (W2) or (W3).

nL represents an integer of 0 or more and 5 or less.

L represents an alkylene group, a cycloalkylene group, an arylene group or a divalent heterocyclic group, and these groups optionally have a substituent. When a plurality of L are present, they may be the same or different.

In the formula (3a), $E^1$, $E^2$, $E^3$ or $E^4$ binds to L. In the formula (3b), a carbon atom binding to $R^6$, $R^7$, $R^8$ or $R^9$ binds to L. In the formula (3c), $E^1$, $E^2$, $E^3$ or $E^4$ binds to other constitutional units and a carbon atom binding to $R^6$, $R^7$, $R^8$ or $R^9$ binds to other constitutional units. In the formula (3d), $E^1$, $E^2$, $E^3$ or $E^4$ binds to other constitutional units. In the formula (3), a carbon atom binding to $R^6$, $R^7$, $R^8$ or $R^9$ binds to other constitutional-units. In the formula (3f), a carbon atom binding to $R^6$, $R^7$, $R^8$ or $R^9$ binds to other constitutional units. In the formula (3g), $E^1$, $E^2$, $E^3$ or $E^4$ binds to other constitutional units. In the formula (3h), a carbon atom binding to $R^6$, $R^7$, $R^8$ or $R^9$ binds to other constitutional units. When $E^1$ binds to L or other constitutional units, $R^{21}$ is not present. When $E^2$ binds to L or other constitutional units, $R^{22}$ is not present. When $E^6$ binds to L or other constitutional units, $R^{23}$ is not present. When $E^4$ binds to L or other constitutional units, $R^{24}$ is not present. When a carbon atom binding to $R^6$ binds to L or other constitutional units, $R^6$ is not present. When a carbon atom binding to $R^7$ binds to L or other constitutional units, $R^7$ is not present. When a carbon atom binding to $R^8$ binds to L or other constitutional units, $R^8$ is not present. When a carbon atom binding to $R^9$ binds to L or other constitutional units, $R^9$ is not present.]

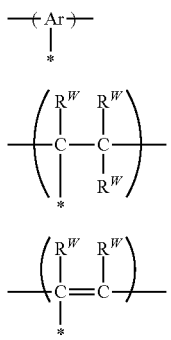

(W1)

(W2)

(W3)

[wherein,

* represents a connecting bond to L.

Ar represents an aromatic hydrocarbon group or a heterocyclic group, and these groups optionally have a substituent.

$R^W$ represents a hydrogen atom, an alkyl group, a cycloalkyl group, an alkoxy group, a cycloalkoxy group, an aryl group, an aryloxy group, a monovalent heterocyclic group or a halogen atom, and these groups optionally have a substituent. A plurality of $R^W$ may be the same or different, and may be combined together to form a ring together with atoms to which they are attached.]

In the formulae (3a) to (3e), when M is an iridium atom, $n_1'$ is preferably 1 or 2, more preferably 2, since the luminance life of a light emitting device using the metal-containing polymer compound is excellent. When P is a platinum atom, $n_1'$ is preferably 1, since the luminance life of a light emitting device using the metal-containing polymer compound is excellent.

In the formula (3g) and the formula (3h), when M is an iridium atom, $n_4$ is preferably 1, since the luminance life of a light emitting device using the metal-containing polymer compound is excellent.

In the formulae (3a) to (3h), at least one selected from the group consisting of $R^{21}$, $R^{22}$, $R^{23}$ and $R^{24}$ is preferably a group represented by the formula (D-A) or (D-B), since the metal-containing polymer compound shows more excellent quantum yield.

In the formulae (3a) to (3h), when a plurality of $R^{21}$, $R^{22}$, $R^{23}$ and $R^{24}$ are present, it is preferable that all of the plurality of $R^{21}$, all of the plurality of $R^{22}$, all of the plurality of $R^{23}$ or all of the plurality of $R^{24}$ are a group represented by the formula (D-A) or (D-B).

In the formulae (3a) to (3h), at least one selected from the group consisting of $R^{21}$, $R^{22}$, $R^{23}$ and $R^{24}$ is preferably a group represented by the formula (D-A), more preferably a group represented by the formula (D-A1), (D-A2) or (D-A3), further preferably a group represented by the formula (D-A3), since the metal-containing polymer compound shows more excellent quantum yield.

In the formulae (3a) to (3h), $R^{22}$ is preferably a group represented by the formula (D-A) or (D-B), more preferably a group represented by the formula (D-A), further preferably a group represented by the formula (D-A1), (D-A2) or (D-A3), particularly preferably a group represented by the formula (D-A3), since the metal-containing polymer compound shows more excellent quantum yield.

In the formulae (3a) to (3h), when $R^{21}$, $R^{22}$, $R^{23}$ and $R^{24}$ are a group other than the group represented by the formula (D-A) or (D-B), $R^{21}$, $R^{22}$, $R^{23}$ and $R^{24}$ are preferably a hydrogen atom, an alkyl group, a cycloalkyl group, an aryl group, a monovalent heterocyclic group or a halogen atom, more preferably a hydrogen atom, an alkyl group, a cycloalkyl group or an aryl group, further preferably a hydrogen atom, since synthesis of the metal-containing polymer compound is easy.

In the formulae (3a) to (3h), $Z^a$ is preferably a direct bond, an oxygen atom, a sulfur atom, $-CR^{Za}R^{Zb}-$, $-CR^{Zc}{}_2-$ or $-NR^{Zc}-$, more preferably a direct bond, $-CR^{Za}R^{Zb}-$ or $-CR^{Zc}{}_2-$, further preferably $-CR^{Za}R^{Zb}-$ or $-CR^{Zc}{}_2-$, particularly preferably $-CR^{Za}R^{Zb}-$.

In the formulae (3a) to (3h), $Z^b$ is preferably a direct bond, an oxygen atom, a sulfur atom, $-CR^{Za}R^{Zb}-$, $-CR^{Zc}{}_2-$ or $-NR^{Zc}-$, more preferably a direct bond, $-CR^{Za}R^{Zb}-$ or $-CR^{Zc}{}_2-$, further preferably a direct bond or $-CR^{Za}R^{Zb}-$, particularly preferably a direct bond.

At least one of $Z^a$ and $Z^b$ is an oxygen atom, a sulfur atom, $-C(=O)-$, $-CR^{Za}R^{Zb}-$, $-CR^{Zc}{}_2-$ or $-NR^{Zc}-$.

In the formulae (3a) to (3h), the combination of $Z^a$ and $Z^b$ is preferably a combination in which $Z^a$ is $-CR^{Za}R^{Zb}-$ and $Z^b$ is a direct bond, a combination in which $Z^a$ is $-CR^{Za}R^{Zb}-$ and $Z^b$ is $-NR^{Zc}-$, a combination in which $Z^a$ is $-CR^{Za}R^{Zb}-$ and $Z^b$ is an oxygen atom, a combination in which $Z^a$ is $-CR^{Za}R^{Zb}-$ and $Z^b$ is a sulfur atom, a combination in which $Z^a$ is a direct bond and $Z^b$ is $-CR^{Za}R^{Zb}-$, a combination in which $Z^a$ is $-NR^{Zc}-$ and $Z^b$ is $-CR^{Za}R^{Zb}-$, a combination in which $Z^a$ is an oxygen atom and $Z^b$ is $-CR^{Za}R^{Zb}-$, a combination in which $Z^a$ is a sulfur atom and $Z^b$ is $-CR^{Za}R^{Zb}-$, a combination in which $Z^a$ is $-CR^{Zc}{}_2-$ and $Z^b$ is a direct bond, a combination in which $Z^a$ is $-CR^{Zc}{}_2-$ and $Z^b$ is $-NR^{Zc}-$, a combination in which $Z^a$ is an oxygen atom and $Z^b$ is a direct bond, a combination in which $Z^a$ is an oxygen atom and $Z^b$ is $-NR^{Zc}-$, a combination in which $Z^a$ is a sulfur atom and $Z^b$ is a direct bond, a combination in which $Z^a$ is $-C(=O)-$ and $Z^b$ is a direct bond, a combination in which $Z^a$ is $-NR^{Zc}-$ and $Z^b$ is a direct bond, a combination in which $Z^a$ is a direct bond and $Z^b$ is $-CR^{Zc}{}_2-$ or a combination in which $Z^a$ is a direct bond and $Z^b$ is a sulfur atom, more preferably a combination in which $Z^a$ is $-CR^{Za}R^{Zb}-$ and $Z^b$ is a direct bond, a combination in which $Z^a$ is a direct bond and $Z^b$ is $-CR^{Za}R^{Zb}-$, a combination in which $Z^a$ is $-CR^{Zc}{}_2-$ and $Z^b$ is a direct bond or a combination in which $Z^a$ is a direct bond and $Z^b$ is $-CR^{Zc}{}_2-$, further preferably a combination in which $Z^a$ is $-CR^{Za}R^{Zb}-$ and $Z^b$ is a direct bond or a combination in which $Z^a$ is $-CR^{Zc}{}_2-$ and $Z^b$ is a direct bond, particularly preferably a combination in which $Z^a$ is $-CR^{Za}R^{Zb}-$ and $Z^b$ is a direct bond, since the metal-containing polymer compound shows more excellent quantum yield.

In the formulae (3a) to (3h), $R^{Za}$ is preferably an alkyl group optionally having a substituent, since the luminance life of a light emitting device using the metal-containing polymer compound is excellent.

In the formulae (3a) to (3h), $R^{Zb}$ is preferably an aryl group optionally having a substituent, more preferably a phenyl group optionally having a substituent, since the luminance life of a light emitting device using the metal-containing polymer compound is excellent.

In the formulae (3a) to (3h), $R^{Zc}$ is preferably an alkyl group, a cycloalkyl group, an aryl group or a monovalent heterocyclic group, more preferably an alkyl group or an aryl group, since the luminance life of a light emitting device using the metal-containing polymer compound is excellent.

In the formula (3a) and the formula (3b), W is preferably a group represented by the formula (W1), since the external quantum efficiency of a light emitting device using the metal-containing polymer compound is excellent.

In the formula (3a) and the formula (3b), nL is preferably an integer of 0 to 2, more preferably 0 or 1.

In the formula (3a) and the formula (3b), L is preferably an alkylene group or an arylene group, more preferably an arylene group.

In the formula (W1), Ar is preferably an aromatic hydrocarbon group.

In the formulae (W2) and (W3), $R^W$ is preferably a hydrogen atom or an alkyl group, more preferably a hydrogen atom.

The metal-containing constitutional unit includes, for example, constitutional units represented by the following formulae (Ir-301) to (Ir-310).

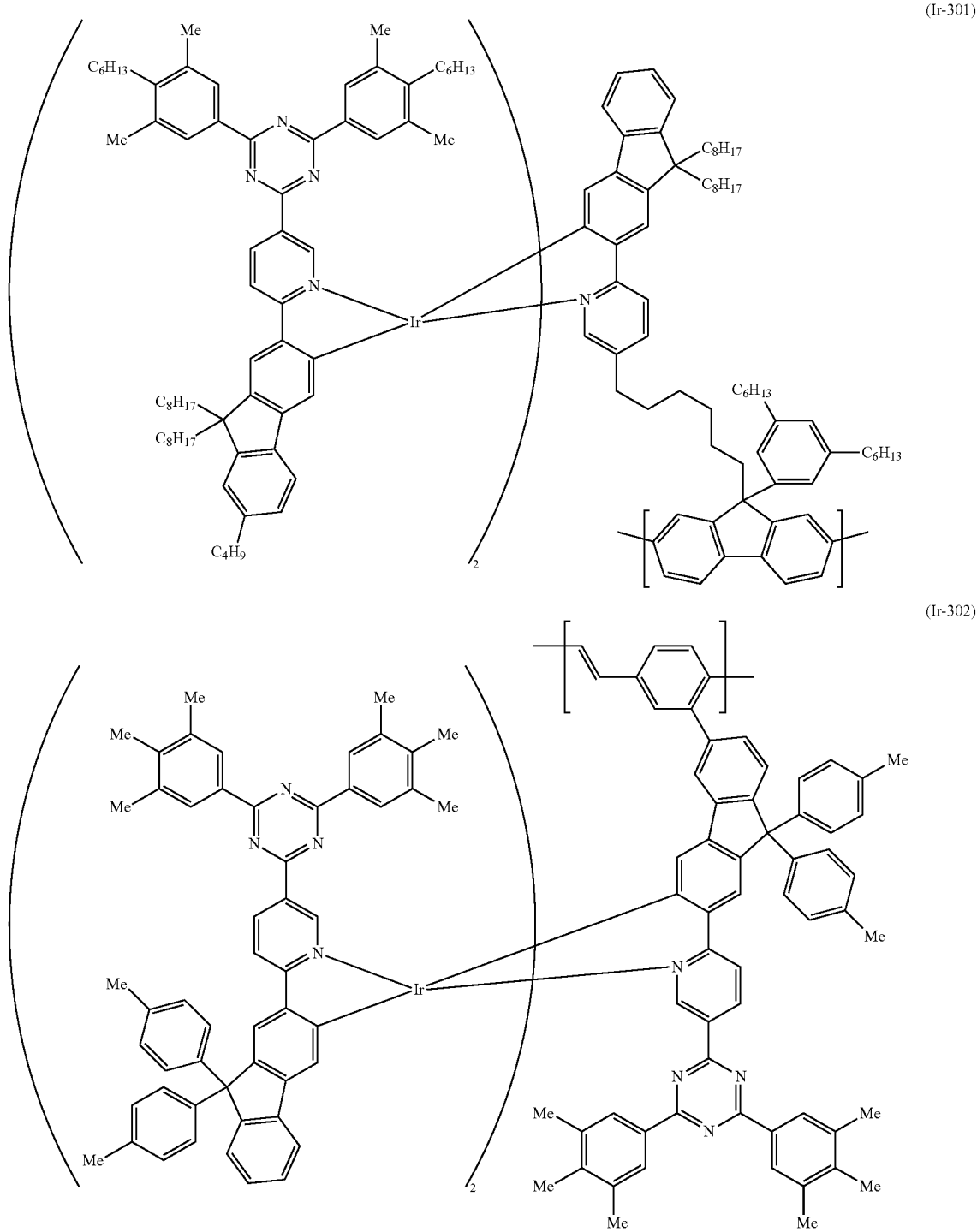

(Ir-303)
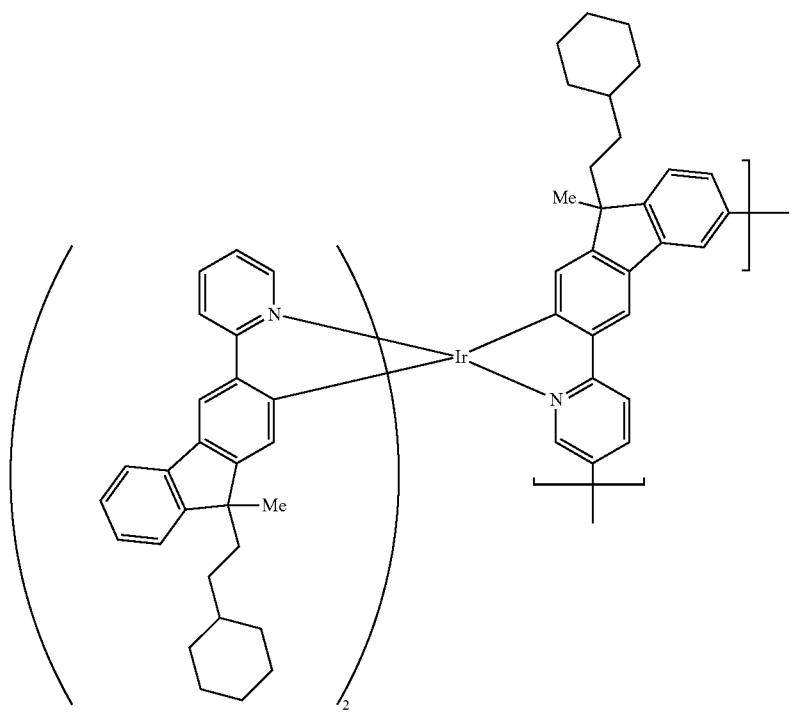
(Ir-304)
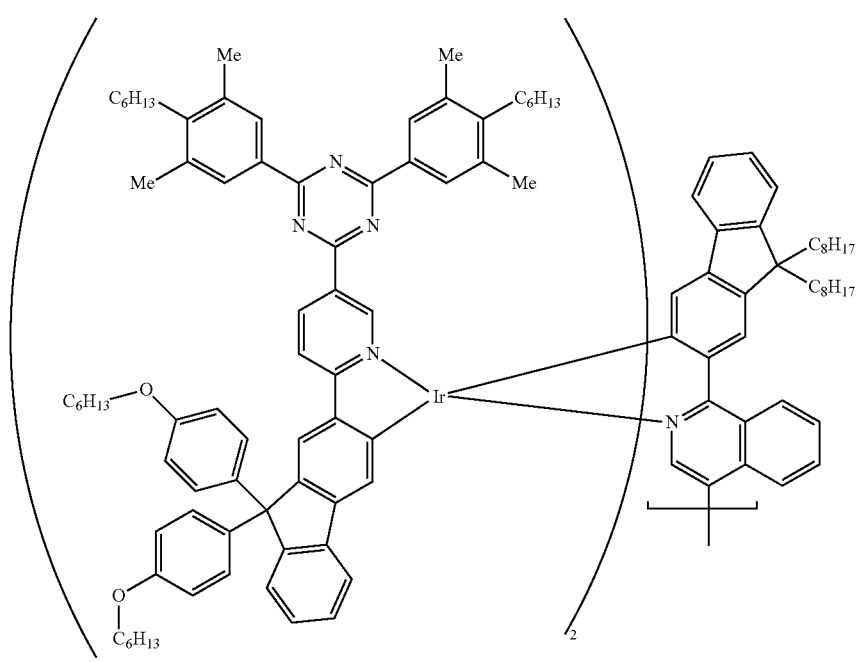

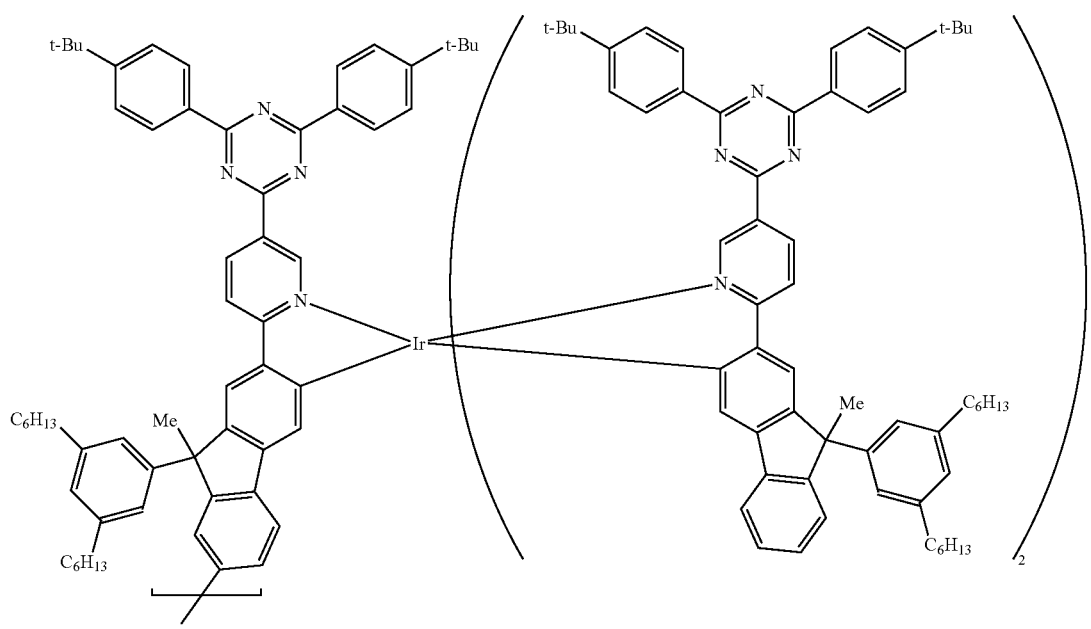
(Ir-305)
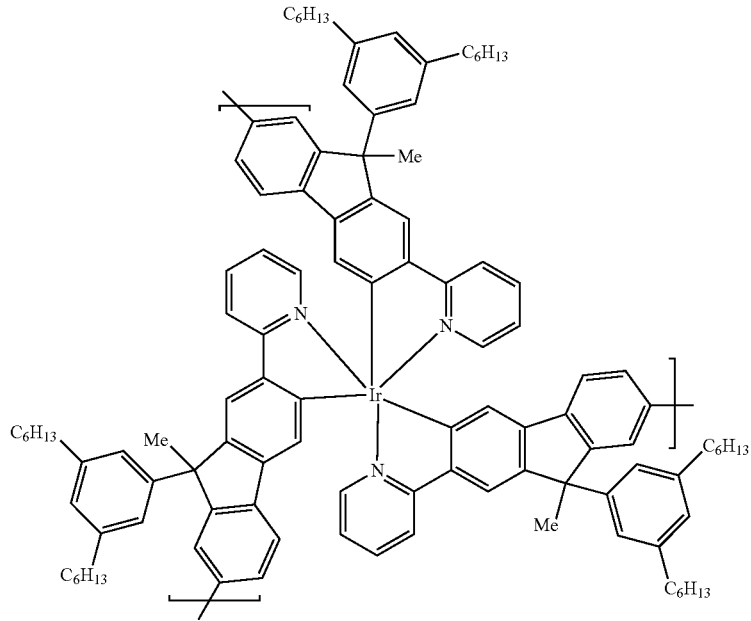
(Ir-306)

-continued
(IR-307)
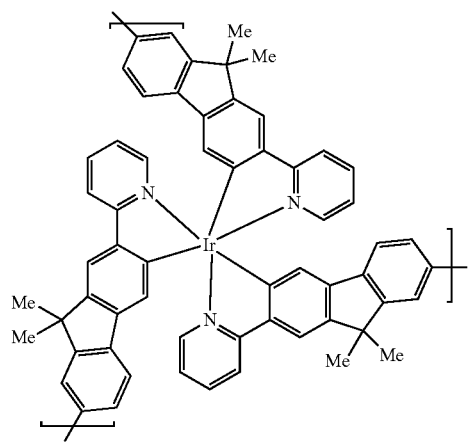
(IR-308)
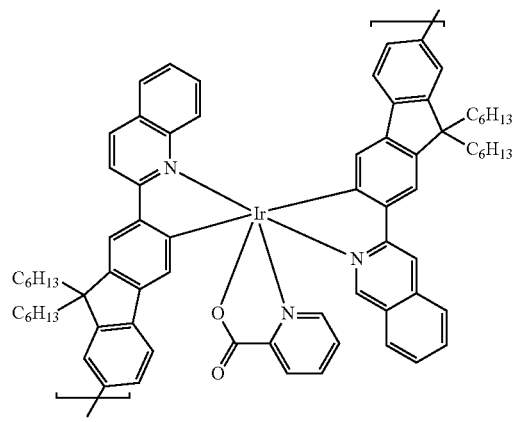
(Ir-309)
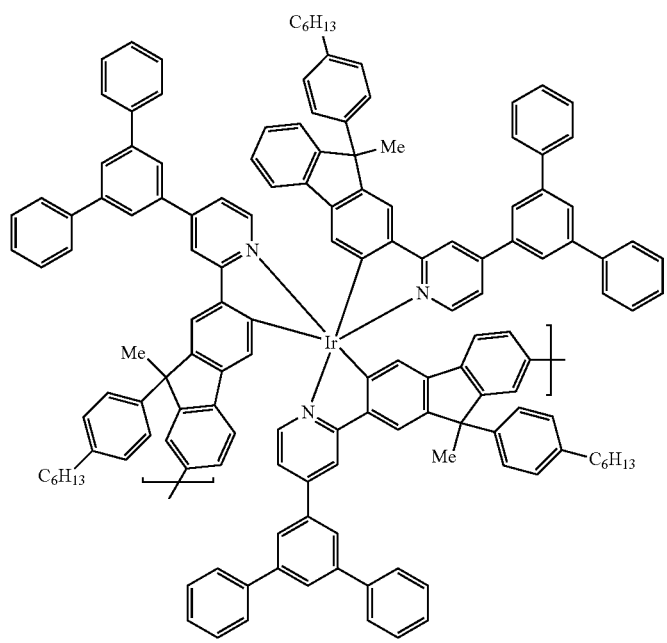

-continued (Ir-310)

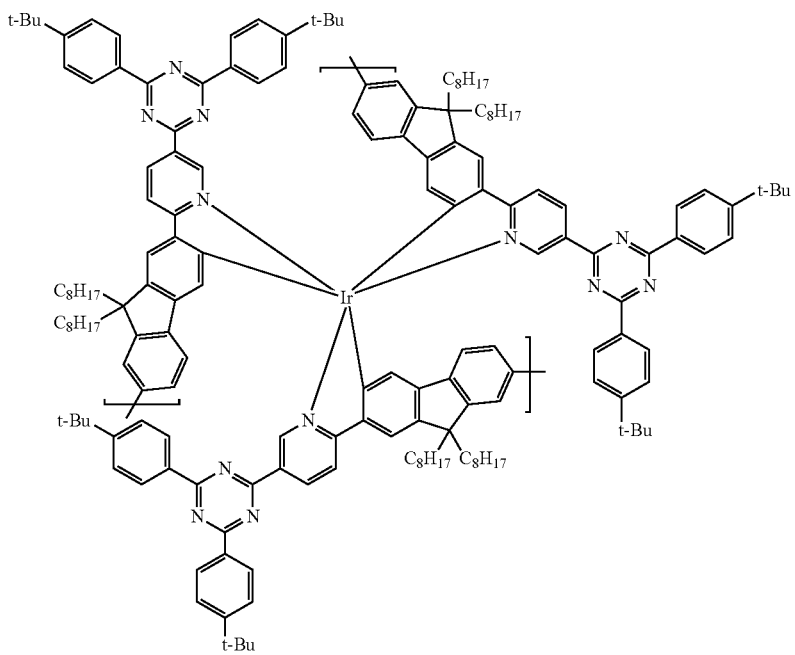

In the metal-containing polymer compound, the metal-containing constitutional units may be contained singly or in combination of two or more.

It is preferable for the metal-containing polymer compound to contain a constitutional unit other than the metal-containing constitutional unit. The constitutional unit other than the metal-containing constitutional unit is preferably at least one constitutional unit selected from the group consisting of constitutional units represented by the formula (Y) and constitutional units represented by the formula (X) described below.

In the metal-containing polymer compound, the content of the metal-containing constitutional unit with respect to the total amount of constitutional units contained in the metal-containing polymer compound is preferably 0.1 to 30% by mol, more preferably 0.5 to 15% by mol, further preferably 1 to 8% by mol, since the external quantum efficiency of a light emitting device using the metal-containing polymer compound is excellent.

The metal-containing polymer compound can be synthesized, for example, according to the same method as for <Production method of polymer host> described later, using a compound represented by the following formula (4).

[wherein,

MR represents a metal-containing constitutional unit.

nV represents 1, 2 or 3.

V represents a group selected from Group A of substituent or a group selected from Group B of substituent. When a plurality of V are present, they may be the same or different.]

<Group A of Substituent>

A chlorine atom, a bromine atom, an iodine atom, and a group represented by —O—S(=O)$_2$R$^{C1}$ (wherein, R$^{C1}$ represents an alkyl group, a cycloalkyl group or an aryl group, and these groups optionally have a substituent.

<Group B of Substituent>

A group represented by —B(OR$^{C2}$)$_2$ (wherein, R$^{C2}$ represents a hydrogen atom, an alkyl group, a cycloakyl group or an aryl group, and these groups optionally have a substituent, and the plurality of R$^{C2}$ may be the same or different and may be combined together to form a ring structure together with the oxygen atom to which they are attached.);

a group represented by —BF$_3$Q' (wherein, Q' represents Li, Na, K, Rb or Cs.);

a group represented by —MgY' (wherein, Y' represents a chlorine atom, a bromine atom or an iodine atom.);

a group represented by —ZnY" (wherein, Y" represents a chlorine atom, a bromine atom or an iodine atom.); and a group represented by —Sn(R$^{C3}$)$_3$ (wherein, R$^{C3}$ represents a hydrogen atom, an alkyl group, a cycloalkyl group or an aryl group, and these groups optionally have a substituent, and the plurality of R$^{C3}$ may be the same or different and may be combined together to form a ring structure together with the tin atom to which they are attached.)

As the group represented by —B(OR$^{C2}$)$_2$, groups represented by the following formulae are exemplified.

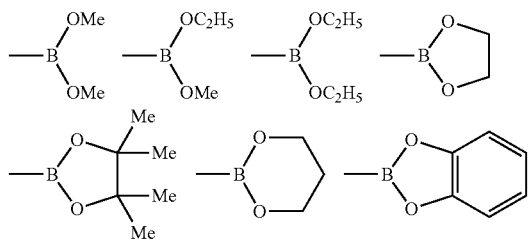

<Composition>

The composition of the present invention comprises at least one material selected from the group consisting of a hole transporting material, a hole injection material, an electron transporting material, an electron injection material, a light emitting material (the light emitting material is different from the metal complex of the present invention), an antioxidant and a solvent, and the metal complex of the present invention.

In the composition of the present invention, the metal complex of the present invention may be contained singly or in combination.

[Host Material]

By a composition comprising the metal complex of the present invention and a host material having at least one function selected from hole injectability, hole transportability, electron injectability and electron transportability, a light emitting device produced using the metal complex of the present invention has more excellent external quantum efficiency. In the composition of the present invention, a host material may be contained singly or two or more host materials may be contained.

In the composition comprising the metal complex of the present invention and the host material, the content of the metal complex of the present invention is usually 0.01 to 80 parts by weight, preferably 0.05 to 40 parts by weight, more preferably 0.1 to 20 parts by weight, further preferably 1 to 20 parts by weight, when the total amount of the metal complex of the present invention and the host material is 100 parts by weight.

It is preferable that the lowest excited triplet state ($T_1$) of the host material has energy level equal to or higher than the lowest excited triplet state ($T_1$) of the metal complex of the present invention since then a light emitting device produced using the composition of the present invention has more excellent external quantum efficiency.

It is preferable that the host material shows solubility in a solvent which is capable of dissolving the metal complex of the present invention from the standpoint of producing a light emitting device produced using the composition of the present invention by a solution coating process.

The host materials are classified into low molecular weight compounds and polymer compounds.

The low molecular weight compound used as the host material includes, for example, a compound having a carbazole skeleton, a compound having a triarylamine skeleton, a compound having a phenanthroline skeleton, a compound having a triaryltriazine skeleton, a compound having an azole skeleton, a compound having a benzothiophene skeleton, a compound having a benzofuran skeleton, a compound having a fluorene skeleton and a compound having a spirofluorene skeleton. The low molecular weight compound used as the host material includes, for example, compounds shown below.

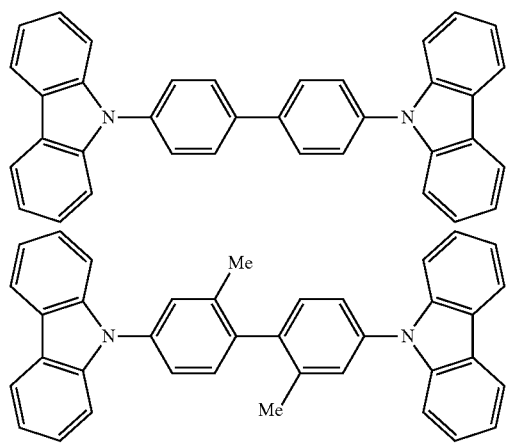

-continued

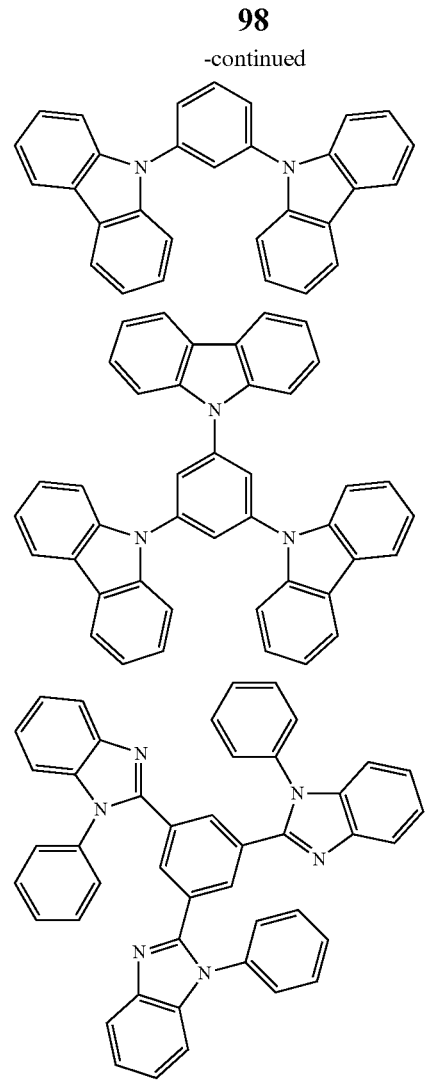

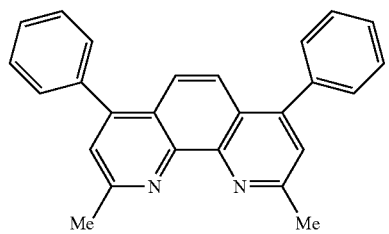

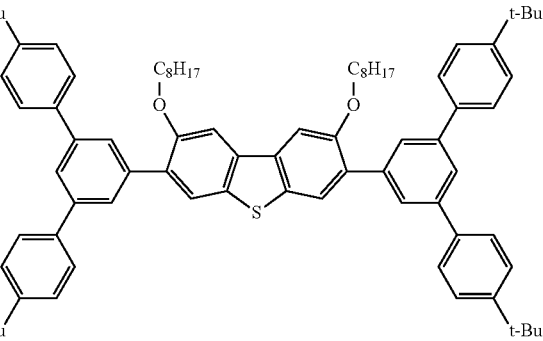

-continued

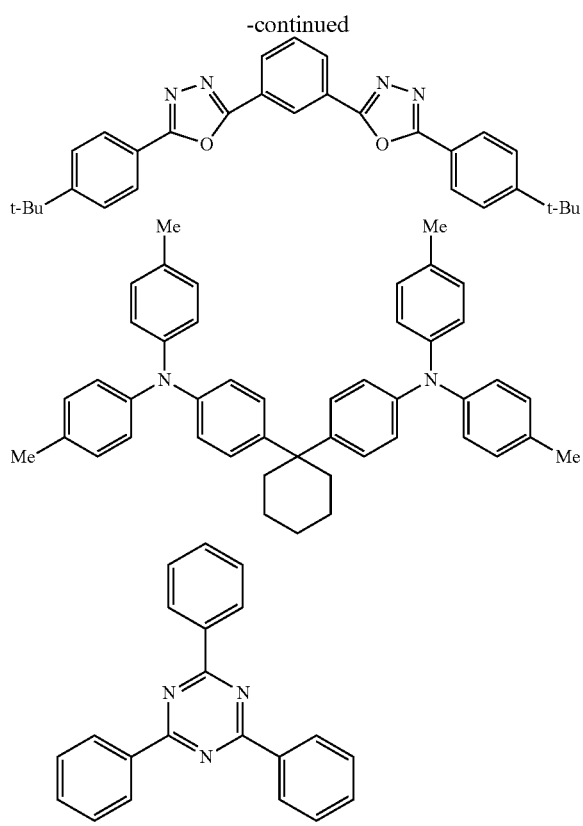

The polymer compound used as a host material includes, for example, polymer compounds as a hole transporting material described later and polymer compounds as an electron transporting material described later.

[Polymer Host]

The polymer compound which is preferable as a host compound (hereinafter, referred to also as "polymer host") will be explained.

The polymer host is preferably a polymer compound comprising a constitutional unit represented by the formula (Y):

 (Y)

[wherein, $Ar^{Y1}$ represents an arylene group, a divalent heterocyclic group or a divalent group in which at least one arylene group and at least one divalent heterocyclic group are bonded directly to each other, and these groups each optionally have a substituent.]

The arylene group represented by $Ar^{Y1}$ is more preferably a group represented by the formula (A-1), the formula (A-2), the formulae (A-6) to (A-10), the formula (A-19) or the formula (A-20), further preferably a group represented by the formula (A-1), the formula (A-2), the formula (A-7), the formula (A-9) or the formula (A-19), and these groups each optionally have a substituent.

The divalent heterocyclic group represented by $Ar^{Y1}$ is more preferably a group represented by the formulae (AA-1) to (AA-4), the formulae (AA-10) to (AA-15), the formulae (AA-18) to (AA-21), the formula (AA-33) or the formula (AA-34), further preferably a group represented by the formula (AA-4), the formula (AA-10), the formula (AA-12), the formula (AA-14) or the formula (AA-33), and these groups each optionally have a substituent.

The more preferable range and the further preferable range of the arylene group and the divalent heterocyclic group in the divalent group in which at least one arylene group and at least one divalent heterocyclic group are bonded directly to each other represented by $Ar^{Y1}$ are the same as the more preferable range and the further preferable range of the arylene group and the divalent heterocyclic group represented by $Ar^{Y1}$ described above, respectively.

"The divalent group in which at least one arylene group and at least one divalent heterocyclic group are bonded directly to each other" includes, for example, groups represented by the following formulae, and each of them optionally has a substituent.

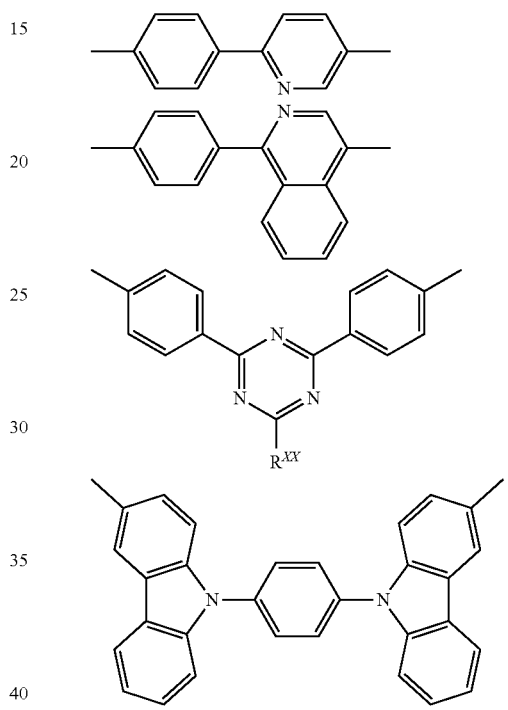

[wherein, $R^{XX}$ represents a hydrogen atom, an alkyl group, a cycloalkyl group, an aryl group or a monovalent heterocyclic group and these groups each optionally have a substituent.]

$R^{XX}$ is preferably an alkyl group, a cycloalkyl group or an aryl group, and these groups each optionally have a substituent.

The substituent which the group represented by $Ar^{Y1}$ optionally has is preferably an alkyl group, a cycloalkyl group or an aryl group, and these groups optionally further have a substituent.

The constitutional unit represented by the formula (Y) includes, for example, constitutional units represented by the formulae (Y-1) to (Y-10), and from the standpoint of the luminance life of the light emitting device produced using the composition comprising the polymer host and the metal complex of the present invention preferable are constitutional units represented by the formula (Y-1), (Y-2) or (Y-3), from the standpoint of electron transportability preferable are constitutional units represented by the formulae (Y-4) to (Y-7), and from the standpoint of hole transportability preferable are constitutional units represented by the formulae (Y-8) to (Y-10).

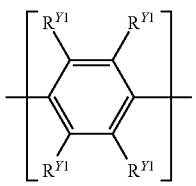

(Y-1)

[wherein, $R^{Y1}$ represents a hydrogen atom, an alkyl group, a cycloalkyl group, an alkoxy group, a cycloalkoxy group, an aryl group or a monovalent heterocyclic group, and these groups each optionally have a substituent. The plurality of $R^{Y1}$ may be the same or different, and adjacent $R^{Y1}$s may be combined together to form a ring together with the carbon atoms to which they are attached.]

$R^{Y1}$ is preferably a hydrogen atom, an alkyl group, a cycloalkyl group or an aryl group, and these groups each optionally have a substituent.

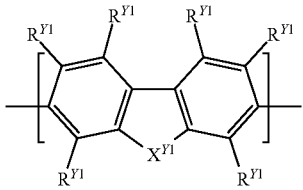

(Y-2)

[wherein, $R^{Y1}$ represents the same meaning as described above. $X^{Y1}$ represents a group represented by —C($R^{Y2}$)$_2$—, —C($R^{Y2}$)=C($R^{Y2}$)— or —C($R^{Y2}$)$_2$—C($R^{Y2}$)$_2$—. $R^{Y2}$ represents a hydrogen atom, an alkyl group, a cycloalkyl group, an alkoxy group, a cycloalkoxy group, an aryl group or a monovalent heterocyclic group and these groups each optionally have a substituent. The plurality of $R^{Y2}$ may be the same or different, and these $R^{Y2}$s may be combined together to form a ring together with the carbon atoms to which they are attached.]

$R^{Y2}$ is preferably an alkyl group, a cycloalkyl group, an aryl group or a monovalent heterocyclic group, more preferably an alkyl group a cycloalkyl group or an aryl group, and these groups each optionally have a substituent.

Regarding the combination of two $R^{Y2}$s in the group represented by —C($R^{Y2}$)$_2$— in $X^{Y1}$, it is preferable that the both are an alkyl group or a cycloalkyl group, the both are an aryl group, the both are a monovalent heterocyclic group, or one is an alkyl group or a cycloalkyl group and the other is an aryl group or a monovalent heterocyclic group, it is more preferable that one is an alkyl group or cycloalkyl group and the other is an aryl group, and these groups each optionally have a substituent. The two groups $R^{Y2}$ may be combined together to form a ring together with the atoms to which they are attached, and when the groups $R^{Y2}$ form a ring, the group represented by —C($R^{Y2}$)$_2$— is preferably a group represented by the formulae (Y-A1) to (Y-A5), more preferably a group represented by the formula (Y-A4), and these groups each optionally have a substituent.

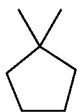

(Y-A1)

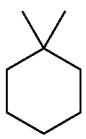

(Y-A2)

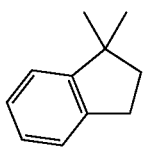

(Y-A3)

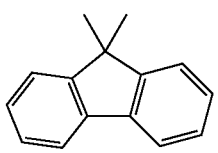

(Y-A4)

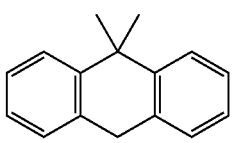

(Y-A5)

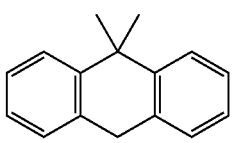

Regarding the combination of two $R^2$ s in the group represented by —C($R^{Y2}$)=C($R^{Y2}$)— in $X^{Y1}$, it is preferable that the both are an alkyl group or cycloalkyl group, or one is an alkyl group or a cycloalkyl group and the other is an aryl group, and these groups each optionally have a substituent.

Four $R^{Y2}$ s in the group represented by —C($R^{Y2}$)$_2$—C($R^{Y2}$)$_2$— in $X^{Y1}$ are preferably an alkyl group or a cycloalkyl group optionally having a substituent. The plurality of $R^{Y2}$ may be combined together to form a ring together with the atoms to which they are attached, and when the groups $R^{Y2}$ form a ring, the group represented by —C($R^{Y2}$)$_2$—C($R^{Y2}$)$_2$— is preferably a group represented by the formulae (Y-B1) to (Y-B5), more preferably a group represented by the formula (Y-B3), and these groups each optionally have a substituent.

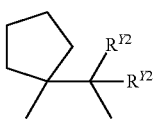

(Y-B1)

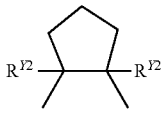

(Y-B2)

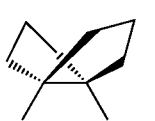

(Y-B3)

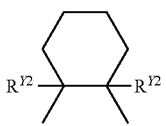

(Y-B4)

-continued

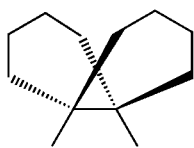
(Y-B5)

[wherein, $R^{Y2}$ represents the same meaning as described above.]

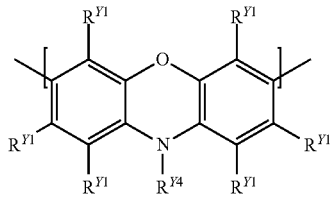
(Y-4)

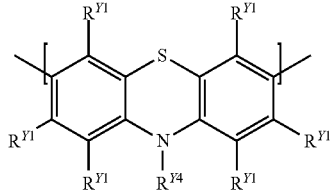
(Y-5)

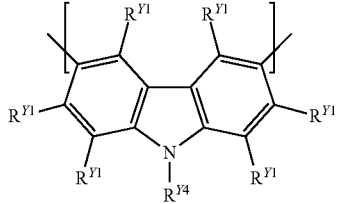
(Y-6)

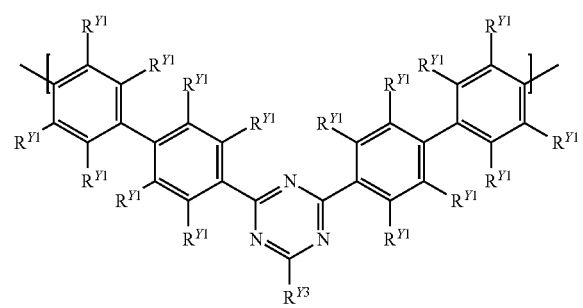
(Y-6)

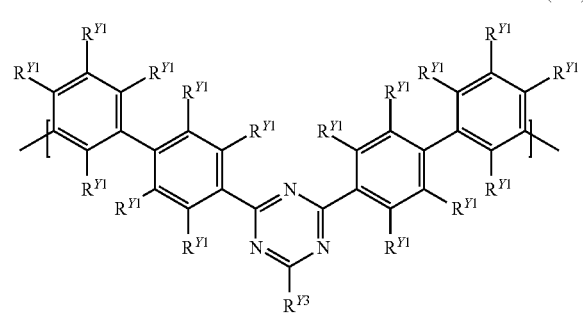
(Y-7)

[wherein, $R^{Y1}$ represents the same meaning as described above. $R^{Y3}$ represents a hydrogen atom, an alkyl group, a cycloalkyl group, an alkoxy group, a cycloalkoxy group, an aryl group or a monovalent heterocyclic group and these groups each optionally have a substituent.]

$R^{Y3}$ is preferably an alkyl group, a cycloalkyl group, an alkoxy group, a cycloalkoxy group, an aryl group or a monovalent heterocyclic group, more preferably an aryl group, and these groups each optionally have a substituent.

(Y-8)

(Y-9)

(Y-10)

[wherein, $R^{Y1}$ represents the same meaning as described above. $R^{Y4}$ represents a hydrogen atom, an alkyl group, a cycloalkyl group, an alkoxy group, a cycloalkoxy group, an aryl group or a monovalent heterocyclic group and these groups each optionally have a substituent.]

$R^{Y4}$ is preferably an alkyl group, a cycloalkyl group, an alkoxy group, a cycloalkoxy group, an aryl group or a monovalent heterocyclic group, more preferably an aryl group, and these groups each optionally have a substituent.

The constitutional unit represented by the formula (Y) includes, for example, a constitutional unit composed of an arylene group represented by the formulae (Y-101) to (Y-121), a constitutional unit composed of a divalent heterocyclic group represented by the formulae (Y-201) to (Y-206), and a constitutional unit composed of a divalent group in which at least one arylene group and at least one divalent heterocyclic group are bonded directly to each other represented by the formulae (Y-301) to (Y-304).

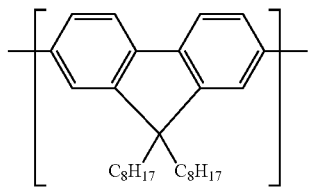
(Y-101)

(Y-102) 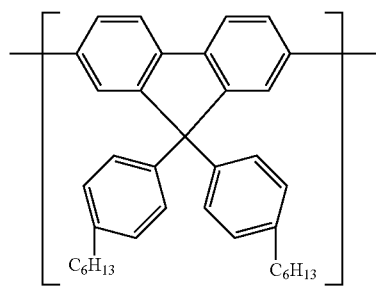
(Y-103) 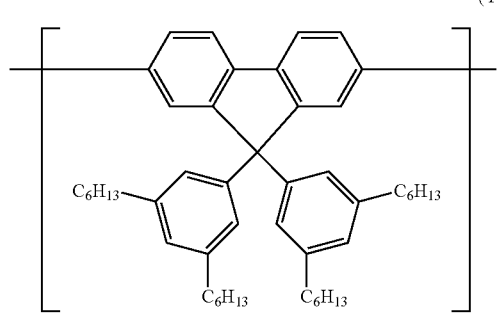
(Y-104) 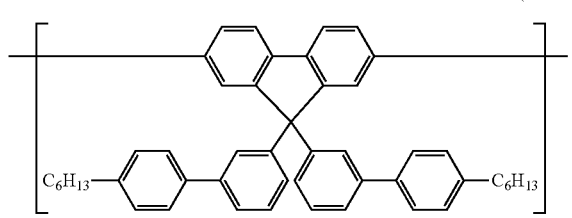
(Y-105) 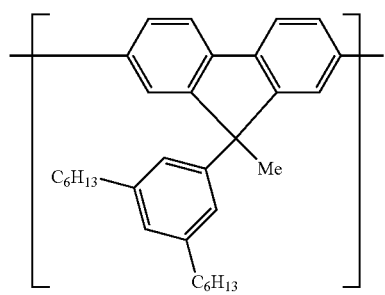
(Y-106) 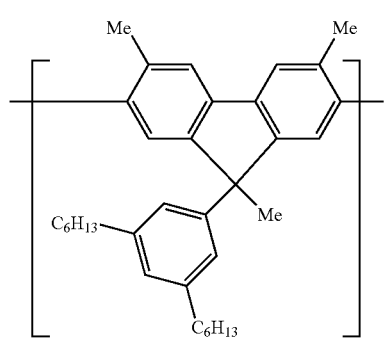
(Y-107) 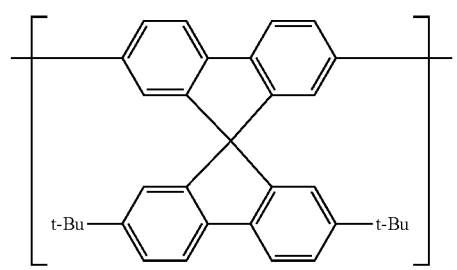
(Y-108) 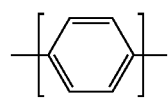
(Y-109) 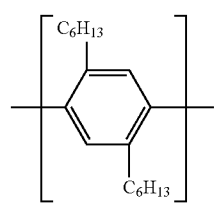
(Y-110) 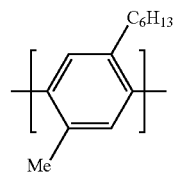
(Y-111) 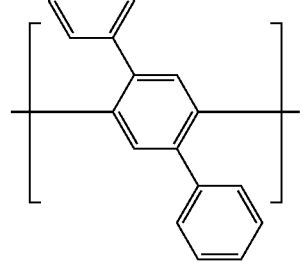
(Y-112) 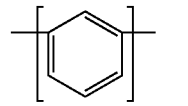
(Y-113) 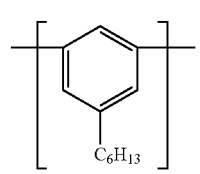
(Y-114) 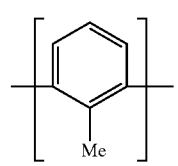

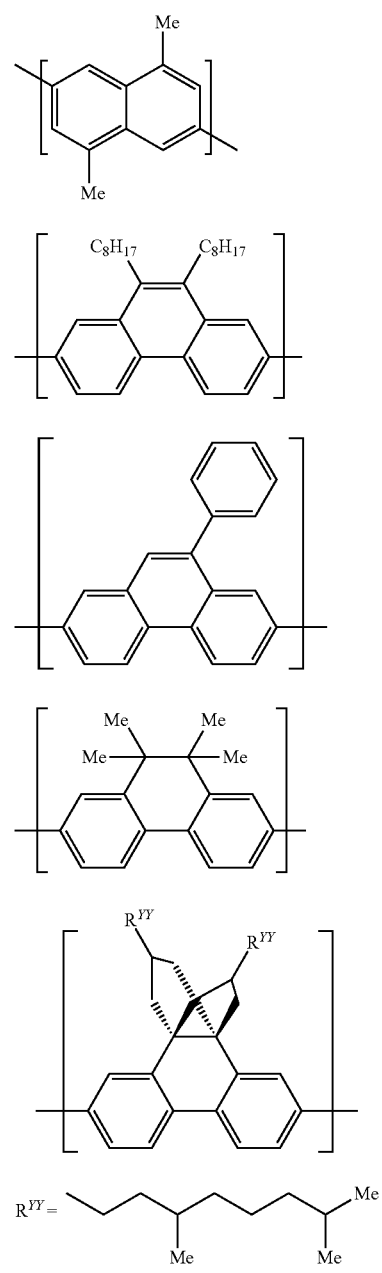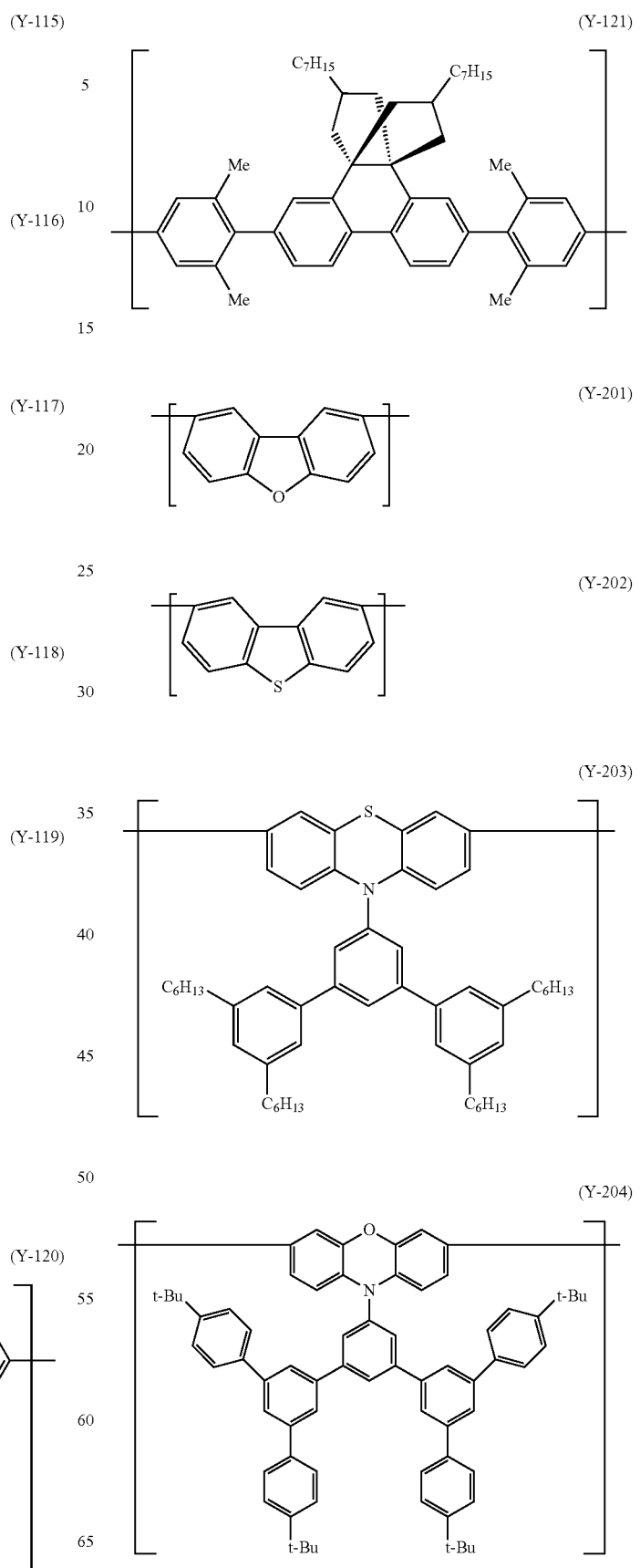

(Y-205)
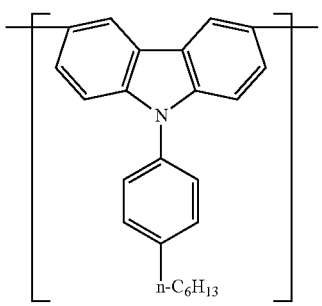

(Y-206)
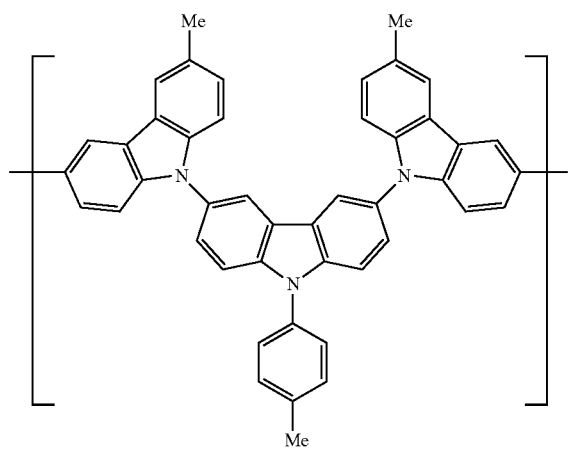

(Y-301)
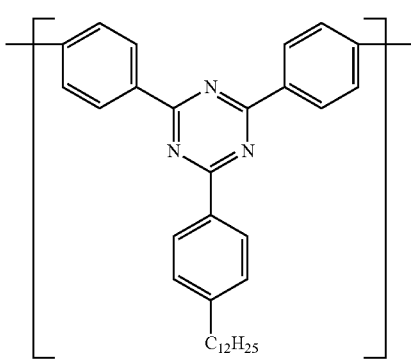

(Y-302)
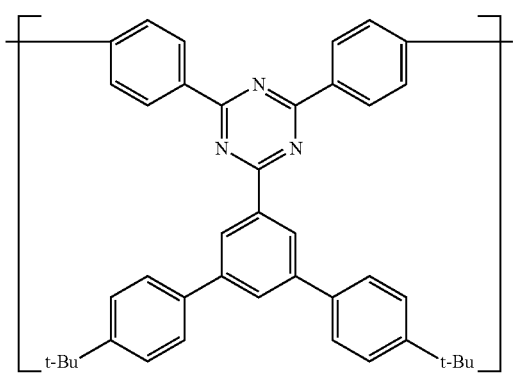

(Y-303)
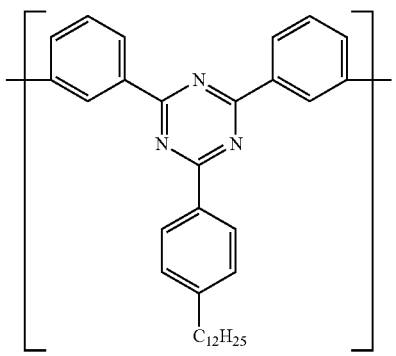

(Y-304)

The amount of the constitutional unit represented by the formula (Y) in which $Ar^{Y1}$ is an arylene group is preferably 0.5 to 100 mol %, more preferably 60 to 95 mol % with respect to the total amount of constitutional units contained in a polymer compound, because the luminance life of a light emitting device by using a composition comprising a polymer host and the metal complex of the present invention is excellent.

The amount of the constitutional unit represented by the formula (Y) in which $Ar^{Y1}$ is a divalent heterocyclic group or a divalent group in which at least one arylene group and at least one divalent heterocyclic group are bonded directly to each other is preferably 0.5 to 30 mol %, more preferably 3 to 20 mol % with respect to the total amount of constitutional units contained in a polymer compound, because the charge transportability of a light emitting device by using a composition comprising a polymer host and the metal complex of the present invention is excellent.

The constitutional unit represented by the formula (Y) may be contained only singly or two or more units thereof may be contained in the polymer host.

It is preferable that the polymer host further comprises a constitutional unit represented by the following formula (X), because then hole transportability is excellent.

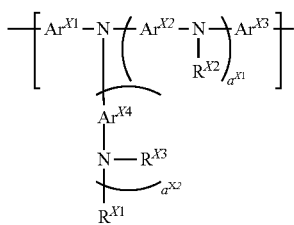

(X)

[wherein, $a^{X1}$ and $a^{X2}$ each independently represent an integer of 0 or more. $Ar^{X1}$ and $Ar^{X3}$ each independently represent an arylene group or a divalent heterocyclic group and these groups each optionally have a substituent. $Ar^{X2}$ and $Ar^{X4}$ each independently represent an arylene group, a divalent heterocyclic group or a divalent group in which at least one arylene group and at least one divalent heterocyclic group are bonded directly to each other, and these groups each optionally have a substituent. $R^{X1}$, $R^{X2}$ and $R^{X3}$ each independently represent a hydrogen atom, an alkyl group, a cycloalkyl group, an aryl group or a monovalent heterocyclic group and these groups each optionally have a substituent.]

$a^{X1}$ is preferably 2 or less, more preferably 1 because the luminance life of the light emitting device by using the composition comprising the polymer host and the metal complex of the present invention is excellent.

$a^{X2}$ is preferably 2 or less, more preferably 0 because the luminance life of the light emitting device by using the composition comprising the polymer host and the metal complex of the present invention is excellent.

$R^{X1}$, $R^{X2}$ and $R^{X3}$ are preferably an alkyl group, a cycloalkyl group, an aryl group or a monovalent heterocyclic group, more preferably an aryl group, and these groups each optionally have a substituent.

The arylene group represented by $Ar^{X1}$ and $Ar^{X3}$ is more preferably a group represented by the formula (A-1) or the formula (A-9), further preferably a group represented by the formula (A-1), and these groups each optionally have a substituent.

The divalent heterocyclic group represented by $Ar^{X1}$ and $Ar^{X3}$ is more preferably a group represented by the formula (AA-1), the formula (AA-2) or the formulae (AA-7) to (AA-26), and these groups each optionally have a substituent.

$Ar^{X1}$ and $Ar^{X3}$ are preferably an arylene group optionally having a substituent.

The arylene group represented by $Ar^{X2}$ and $Ar^{X4}$ is more preferably a group represented by the formula (A-1), the formula (A-6), the formula (A-7), the formulae (A-9) to (A-11) or the formula (A-19), and these groups each optionally have a substituent.

The more preferable range of the divalent heterocyclic group represented by $Ar^{X2}$ and $Ar^{X4}$ is the same as the more preferable range of the divalent heterocyclic group represented by $Ar^{X1}$ and $Ar^{X3}$.

The more preferable range and the further preferable range of the arylene group and the divalent heterocyclic group in the divalent group in which at least one arylene group and at least one divalent heterocyclic group are bonded directly to each other represented by $Ar^{X2}$ and $Ar^{X4}$ are the same as the more preferable range and the further preferable range of the arylene group and the divalent heterocyclic group represented by $Ar^{X1}$ and $Ar^{X3}$, respectively.

The divalent group in which at least one arylene group and at least one divalent heterocyclic group are bonded directly to each other represented by $Ar^{X2}$ and $Ar^{X4}$ includes the same groups as the divalent group in which at least one arylene group and at least one divalent heterocyclic group are bonded directly to each other represented by $Ar^{Y1}$ in the formula (Y).

$Ar^{X2}$ and $Ar^{X4}$ are preferably an arylene group optionally having a substituent.

The substituent which the group represented by $Ar^{X1}$ to $Ar^{X4}$ and $R^{X1}$ to $R^{X3}$ optionally has is preferably an alkyl group, a cycloalkyl group or an aryl group, and these groups optionally further have a substituent.

The constitutional unit represented by the formula (X) is preferably a constitutional unit represented by the formulae (X-1) to (X-7), more preferably a constitutional unit represented by the formulae (X-1) to (X-6), further preferably a constitutional unit represented by the formulae (X-3) to (X-6).

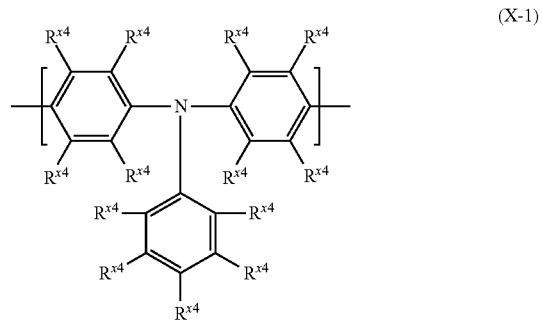

(X-1)

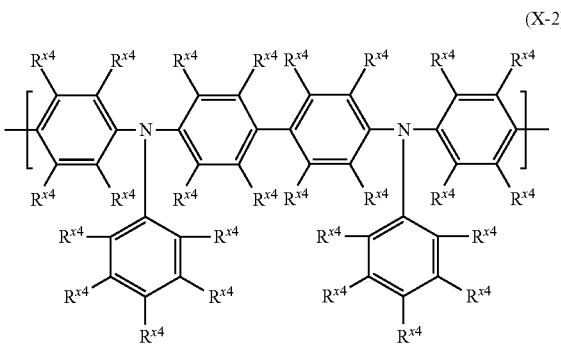

(X-2)

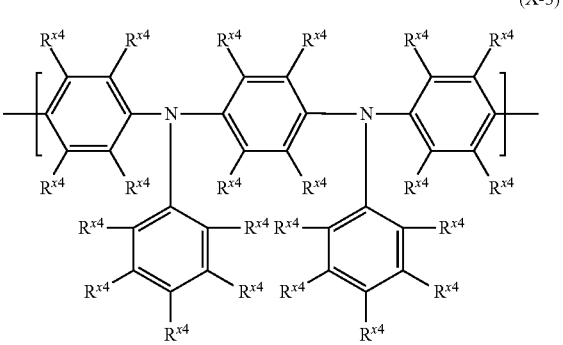

(X-3)

-continued

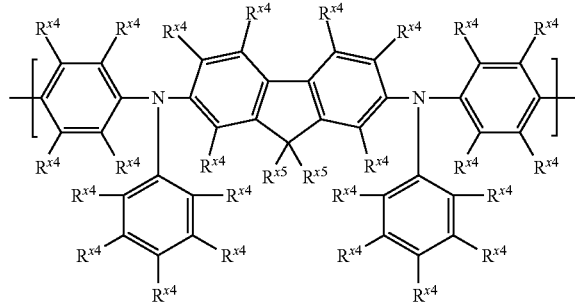

(X-4)

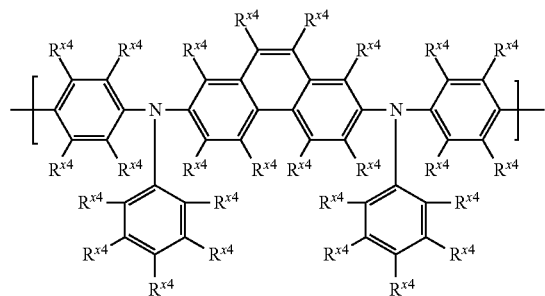

(X-5)

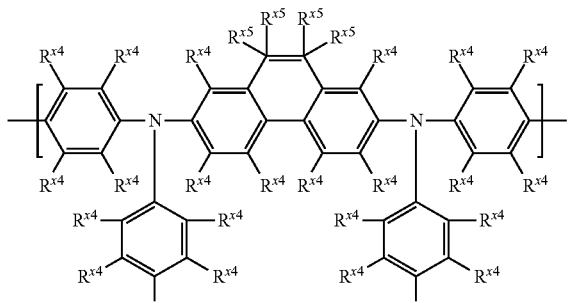

(X-6)

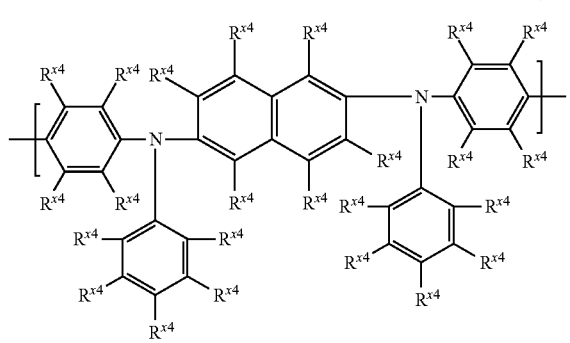

(X-7)

[wherein, $R^{X4}$ and $R^{X5}$ each independently represent a hydrogen atom, an alkyl group, a cycloalkyl group, an alkoxy group, a cycloalkoxy group, an aryl group, an aryloxy group, a halogen atom, a monovalent heterocyclic group or a cyano group and these groups each optionally have a substituent. The plurality of $R^{X4}$ may be the same or different. The plurality of $R^{X5}$ may be the same or different, and adjacent groups $R^{X5}$ may be combined together to form a ring together with the carbon atoms to which they are attached.]

The amount of the constitutional unit represented by the formula (X) is preferably 0.1 to 50 mol %, more preferably 1 to 40 mol %, further preferably 2 to 30 mol % with respect to the total amount of constitutional units contained in a polymer host, because hole transportability is excellent.

The constitutional unit represented by the formula (X) includes, for example, constitutional units represented by the formulae (X1-1) to (X1-11), preferably constitutional units represented by the formulae (X1-3) to (X1-10).

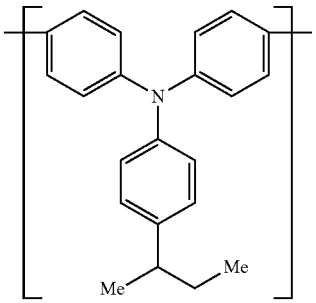

(X1-1)

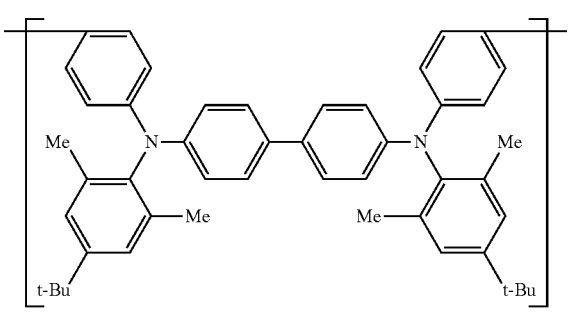

(X1-2)

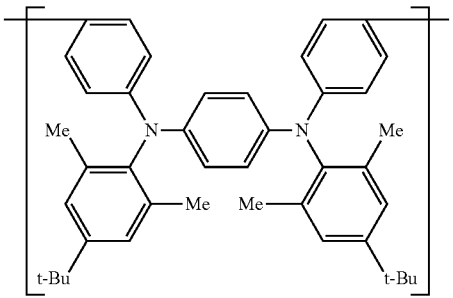

(X1-3)

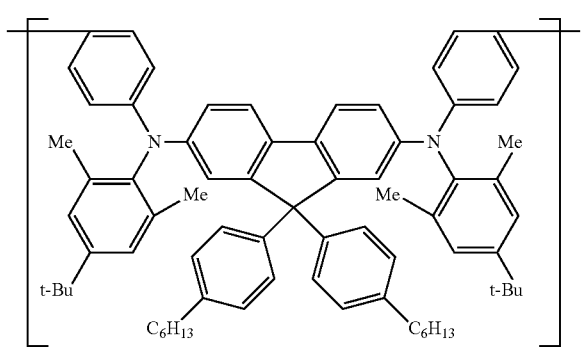

(X1-4)

-continued (X1-5)
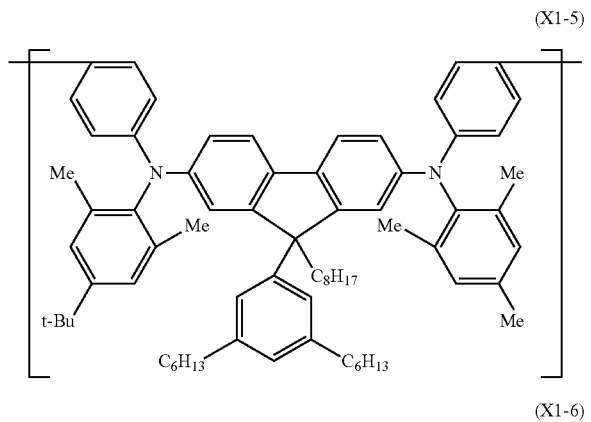

(X1-6)
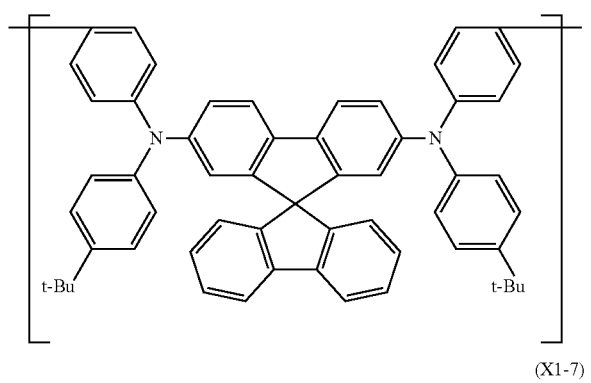

(X1-7)
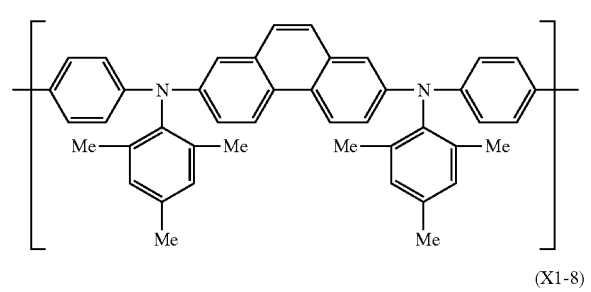

(X1-8)
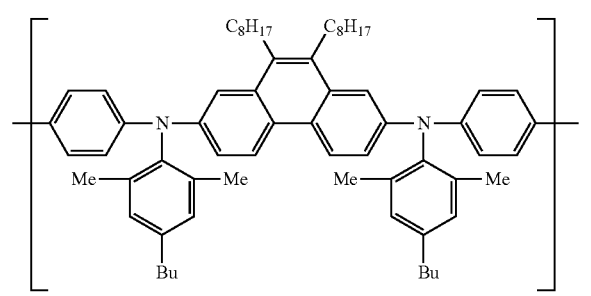

(X1-9)
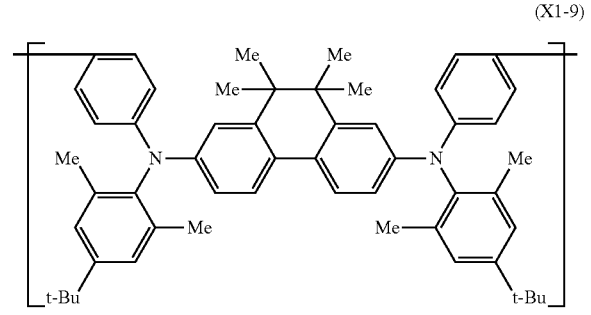

(X1-10)
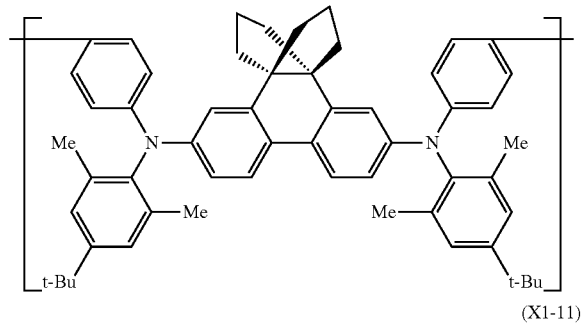

(X1-11)
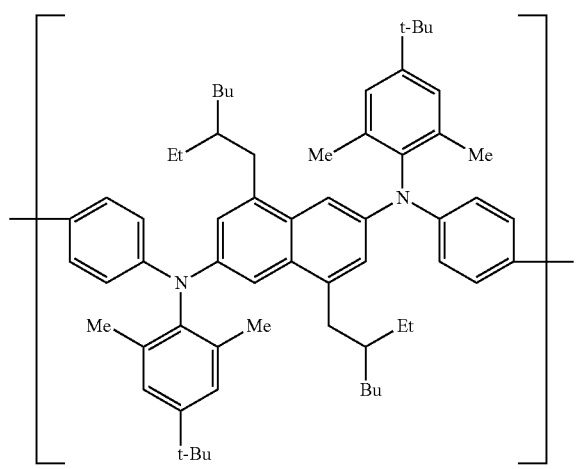

The constitutional unit represented by the formula (X) may be contained only singly or two or more units thereof may be contained in the polymer host.

Examples of the polymer host include polymer compounds P-1 to P-7 in "Table 1" below. Here, "other" constitutional unit denotes a constitutional unit other than the constitutional unit represented by the formula (Y) and the constitutional unit represented by the formula (X)

TABLE 1

| | constitutional unit and mole fraction thereof | | | | |
|---|---|---|---|---|---|
| | formula (Y) | | | formula (X) | |
| polymer compound | formulae (Y-1) to (Y-3) p | formulae (Y-4) to (Y-7) q | formulae (Y-8) to (Y-10) r | formulae (X-1) to (X-7) s | other t |
| P-1 | 0.1 to 99.9 | 0.1 to 99.9 | 0 | 0 | 0 to 30 |
| P-2 | 0.1 to 99.9 | 0 | 0.1 to 99.9 | 0 | 0 to 30 |
| P-3 | 0.1 to 99.9 | 0 | 0 | 0.1 to 99.9 | 0 to 30 |
| P-4 | 0.1 to 99.8 | 0.1 to 99.8 | 0 | 0.1 to 99.8 | 0 to 30 |
| P-5 | 0.1 to 99.8 | 0.1 to 99.8 | 0.1 to 99.8 | 0 | 0 to 30 |
| P-6 | 0.1 to 99.8 | 0 | 0.1 to 99.8 | 0.1 to 99.8 | 0 to 30 |
| P-7 | 0.1 to 99.7 | 0.1 to 99.7 | 0.1 to 99.7 | 0.1 to 99.7 | 0 to 30 |

[In the table, p, q, r, s and t represent the mole fraction of each constitutional unit. p+q+r+s+t=100, and 100≥p+q+r+ s≥70. Other constitutional unit denotes a constitutional unit other than the constitutional unit represented by the formula (Y) and the constitutional unit represented by the formula (X).]

The polymer host may be any of a block copolymer, a random copolymer, an alternating copolymer or a graft copolymer, and may also be another embodiment, and is preferably a copolymer produced copolymerizing a plurality of raw material monomers.

<Production Method of Polymer Host>

The polymer host can be produced by using known polymerization methods described in Chem. Rev., vol. 109, pp. 897-1091 (2009) and the like, for example, methods for causing polymerization by a coupling reaction using a transition metal catalyst such as the Suzuki reaction, the Yamamoto reaction, the Buchwald reaction, the Stille reaction, the Negishi reaction, the Kumada reaction and the like.

In the above-described polymerization methods, the monomer charging method includes a method in which the total amount of monomers is charged in a lump into the reaction system, a method in which a part of monomers is charged and reacted, then, the remaining monomers are charged in a lump, continuously or in divided doses, a method in which monomers are charged continuously or in divided doses, and the like.

The transition metal catalyst includes, for example, a palladium catalyst and a nickel catalyst.

The post treatment of the polymerization reaction is conducted by using known methods, for example, a method in which water-soluble impurities are removed by liquid-separation, a method in which the reaction solution after the polymerization reaction is added to a lower alcohol such as methanol and the like, the deposited precipitate is filtrated, then, dried, and other methods, singly or in combination. When the purity of the polymer host is low, purification can be carried out by usual methods such as, for example, recrystallization, reprecipitation, continuous extraction using a Soxhlet extractor, column chromatography and the like.

The composition comprising the metal complex of the present invention and a solvent (hereinafter, referred to as "ink" in some cases) is suitable for fabrication of a light emitting device using a printing method such as an inkjet printing method and a nozzle printing method.

The viscosity of the ink may be adjusted depending on the kind of the printing method, and when a solution goes through a discharge apparatus such as in an inkjet printing method, the viscosity is preferably in the range of 1 to 20 mPa's at 25° C. for preventing curved aviation and clogging in discharging.

As the solvent contained in the ink, those capable of dissolving or uniformly dispersing solid components in the ink are preferable. The solvent includes, for example, chlorine-based solvents such as 1,2-dichloroethane, 1,1,2-trichloroethane, chlorobenzene and o-dichlorobenzene; ether solvents such as tetrahydrofuran, dioxane, anisole and 4-methylanisole; aromatic hydrocarbon solvents such as toluene, xylene, mesitylene, ethylbenzene, n-hexylbenzene and cyclohexylbenzene; aliphatic hydrocarbon solvents such as cyclohexane, methylcyclohexane, n-pentane, n-hexane, n-heptane, n-octane, n-nonane, n-decane, n-dodecane and bicyclohexyl; ketone solvents such as acetone, methylet hylketone, cyclohexanone and acetophenone; ester solvents such as ethyl acetate, butyl acetate, ethylcellosolve acetate, methyl benzoate and phenyl acetate; poly-hydric alcohols such as ethylene glycol, glycerin and 1,2-hexanediol and derivatives thereof; alcohol solvents such as isopropanol and cyclohexanol; sulfoxide solvents such as dimethyl sulfoxide; and amide solvents such as N-methyl-2-pyrrolidone and N,N-dimethylformamide. These solvents may be used singly or two or more of them may be used in combination.

In the ink, the compounding amount of the above-described solvent is usually 1000 to 100000 parts by weight, preferably 2000 to 20000 parts by weight with respect to 100 parts by weight of the metal complex of the present invention.

[Hole Transporting Material]

The hole transporting material is classified into low molecular weight compounds and polymer compounds, and polymer compounds are preferable, polymer compounds having a crosslinkable group are more preferable.

The polymer compound includes, for example, polyvinylcarbazole and derivatives thereof; polyarylene having an aromatic amine structure in the side chain or main chain and derivatives thereof. The polymer compound may also be a compound in which an electron accepting portion is linked. The electron accepting portion includes, for example, fullerene, tetrafluorotetr a cyanoquinodimethane, tetracyanoethyl ene, trinitrofluorenone and the like, preferably fullerene.

In the composition of the present invention, the compounding amount of the hole transporting material is usually 1 to 400 parts by weight, preferably 5 to 150 parts by weight with respect to 100 parts by weight of the metal complex of the present invention.

The hole transporting material may be used singly or two or more hole transporting materials may be used in combination.

[Electron Transporting Material]

The electron transporting material is classified into low molecular weight compounds and polymer compounds. The electron transporting material optionally has a crosslinkable group.

The low molecular weight compound includes, for example, a metal complex having 8-hydroxyquinoline as a ligand, oxadiazole, anthraquinodimethane, benzoquinone, naphthoquinone, anthraquinone, trtracyanoanthraquinodimethane, fluorenone, diphenyldi cyanoethylene, diphenoquinone and derivatives thereof.

The polymer compound includes, for example, polyphenylene, polyfluorene and derivatives thereof. These polymer compounds may be doped with a metal.

In the composition of the present invention, the compounding amount of the electron transporting material is usually 1 to 400 parts by weight, preferably 5 to 150 parts by weight with respect to 100 parts by weight of the metal complex of the present invention.

The electron transporting material may be used singly or two or more electron transporting materials may be used in combination.

[Hole Injection Material and Electron Injection Material]

The hole injection material and the electron injection material are each classified into low molecular weight compounds and polymer compounds. The hole injection material and the electron injection material optionally has a crosslinkable group.

The low molecular weight compound includes, for example, metal phthalocyanines such as copper phthalocyanine; carbon; oxides of metals such as molybdenum and tungsten; metal fluorides such as lithium fluoride, sodium fluoride, cesium fluoride and potassium fluoride.

The polymer compound includes, for example, polyaniline, polythiophene, polypyrrole, polyphenylenevinylene, polythienylenevinylene, polyquinoline and polyquinoxaline, and derivatives thereof; electrically conductive polymers such as a polymer comprising a group represented by the formula (X) in the side chain or main chain.

In the composition of the present invention, the compounding amounts of the hole injection material and the electron injection material are each usually 1 to 400 parts by weight, preferably 5 to 150 parts by weight with respect to 100 parts by weight of the metal complex of the present invention.

The hole injection material and the electron injection material may each be used singly or two or more of them may be used in combination.

[Ion Dope]

When the hole injection material or the electron injection material comprises an electrically conductive polymer, the electric conductivity of the electrically conductive polymer is preferably $1\times10^{-5}$ S/cm to $1\times10^{3}$ S/cm. For adjusting the electric conductivity of the electrically conductive polymer within such a range, the electrically conductive polymer can be doped with a suitable amount of ions.

The kind of the ion to be doped is an anion for a hole injection material and a cation for an electron injection material. The anion includes, for example, a polystyrenesulfonate ion, an alkylbenzenesulfonate ion and a camphorsulfonate ion. The cation includes, for example, a lithium ion, a sodium ion, a potassium ion and a tetrabutylammonium ion.

The ion to be doped may be used singly or two or more ions to be doped may be used.

[Light Emitting Material]

The light emitting material (the light emitting material is different form the metal complex of the present invention) is classified into low molecular weight compounds and polymer compounds. The light emitting material optionally has a crosslinkable group.

The low molecular weight compound includes, for example, naphthalene and derivatives thereof, anthracene and derivatives thereof, perylene and derivatives thereof, and, triplet light emitting complexes having iridium, platinum or europium as the central metal.

The polymer compound includes, for example, polymer compounds comprising a phenylene group, a naphthalenediyl group, a fluorenediyl group, a phenanthrenediyl group, dihydrophenanthrenediyl group, a group represented by the formula (X), a carbazolediyl group, a phenoxazinediyl group, a phenothiazinediyl group, an anthracenediyl group, a pyrenediyl group and the like.

The light emitting material may comprise a low molecular weight compound and a polymer compound, and preferably, comprises a triplet light emitting complex and a polymer compound.

The triplet light emitting complex includes, for example, metal complexes listed below.

Ir(ppy)₃

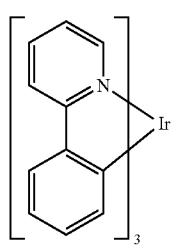

Btp₂Ir(acac)

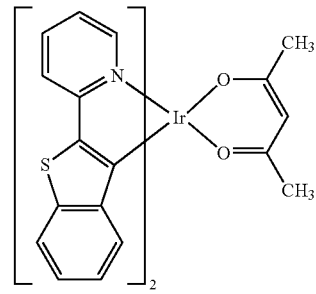

FIrpic

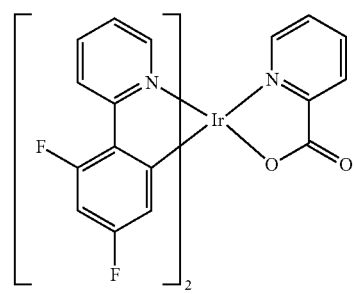

PtOEp

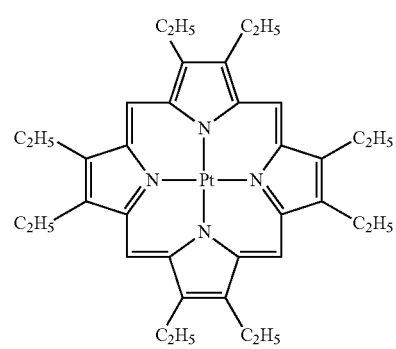

Eu(TTA)₃phen

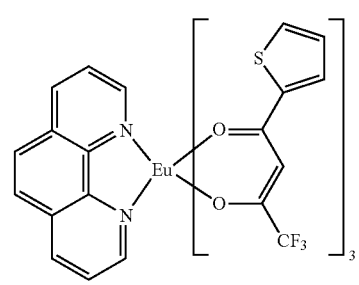

COM-1

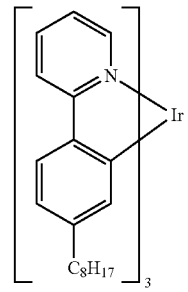

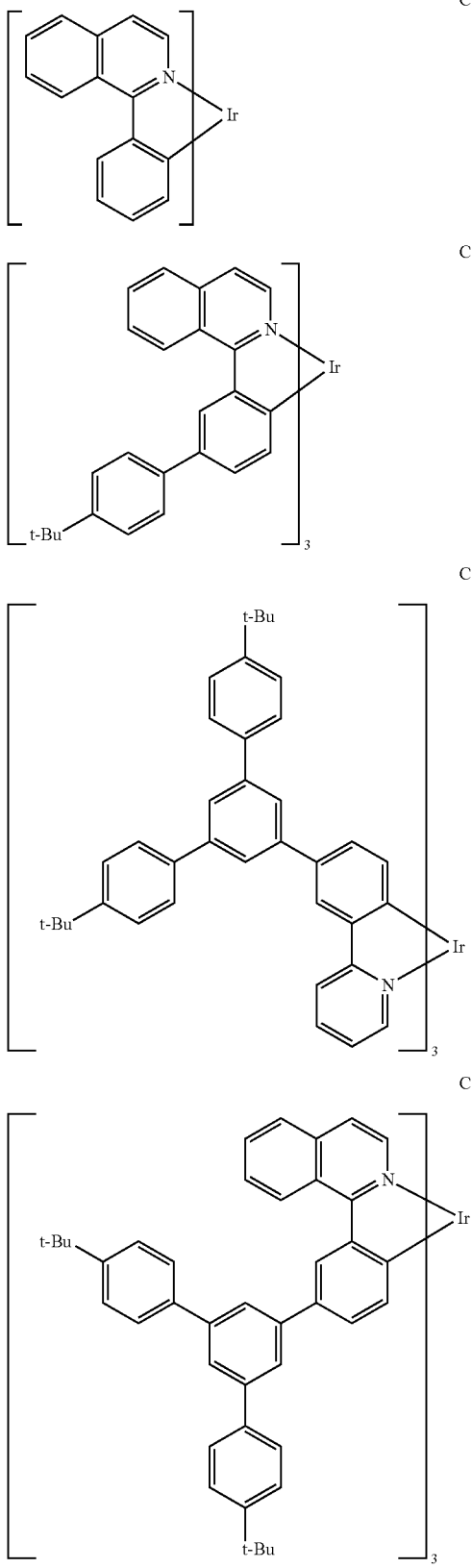

In the composition of the present invention, the compounding amount of the above-described light emitting material is usually 0.1 to 400 parts by weight with respect to 100 parts by weight of the metal complex of the present invention.

[Antioxidant]

The antioxidant may advantageously be one which is soluble in the same solvent as for the metal complex of the present invention and does not disturb light emission and charge transportation, and the examples thereof include phenol antioxidants and phosphorus-based antioxidants.

In the composition of the present invention, the compounding amount of the antioxidant is usually 0.001 to 10 parts by weight with respect to 100 parts by weight of the metal complex of the present invention.

The antioxidant may be used singly or two or more antioxidants may be used in combination.

<Film>

The film produced using the metal complex of the present invention is classified into a film containing the metal complex of the present invention and an insolubilized film produced insolubilizing the metal complex of the present invention in a solvent by cross-linking. The insolubilized film is a film produced cross-linking the metal complex of the present invention by an external stimulus such as heating, light irradiation and the like. Since the insolubilized film is substantially insoluble in a solvent, it can be suitably used for lamination in a light emitting device.

The heating temperature for crosslinking the film is usually 25 to 300° C., and because the external quantum efficiency is improved, preferably 50 to 250° C., more preferably 150 to 200° C.

The kind of light used in light irradiation for crosslinking the film includes, for example, ultraviolet light, near-ultraviolet light and visible light.

The film is suitable as a light emitting layer in a light emitting device.

The film can be fabricated, for example, by a spin coating method, a casting method, a micro gravure coating method, a gravure coating method, a bar coating method, a roll coating method, a wire bar coating method, a dip coating method, a spray coating method, a screen printing method, a flexo printing method, an offset printing method, an inkjet printing method, a capillary coating method or a nozzle coating method, using the ink.

The thickness of the film is usually 1 nm to 10 μm.

<Light Emitting Device>

The light emitting device of the present invention is a light emitting device produced using the metal complex of the present invention, and may be one in which the metal complexes of the present invention are intramolecularly or intermolecularly cross-linked, or one in which the metal complexes of the present inventions are intramolecularly and intermolecularly cross-linked.

The constitution of the light emitting device of the present invention comprises, for example, electrodes consisting of an anode and a cathode, and a layer produced using the metal complex of the present invention disposed between the electrodes.

[Layer Constitution]

The layer produced using the metal complex of the present invention is usually at least one selected from a light emitting layer, a hole transporting layer, a hole injection layer, an electron transporting layer and an electron injection layer, preferably a light emitting layer. These layers comprise a light emitting material, a hole transporting material, a hole injection material, an electron transporting material and an electron injection material, respectively. These layers can be formed by the same method as the above-described film fabrication using inks prepared by dissolving a light emitting material, a hole transporting material, a hole injection material, an electron transporting material and an electron injection material, respectively, in the solvent described above.

The light emitting device comprises a light emitting layer between an anode and a cathode. The light emitting device of the present invention preferably comprises at least one of a hole injection layer and a hole transporting layer between an anode and a light emitting layer from the standpoint of hole injectability and hole transportability, and preferably comprises at least one of an electron injection layer and an electron transporting layer between a cathode and a light emitting layer from the standpoint of electron injectability and electron transportability.

The material of a hole transporting layer, an electron transporting layer, a light emitting layer, a hole injection layer and an electron injection layer includes the above-described hole transporting materials, electron transporting materials, light emitting materials, hole injection materials and electron injection materials, respectively, in addition to the metal complex of the present invention.

When the material of a hole transporting layer, the material of an electron transporting layer and the material of a light emitting layer are soluble in a solvent which is used in forming a layer adjacent to the hole transporting layer, the electron transporting layer and the light emitting layer, respectively, in fabrication of a light emitting device, it is preferable that the materials have a crosslinkable group to avoid dissolution of the materials in the solvent. After forming the layers using the materials having a crosslinkable group, the layers can be insolubilized by crosslinking the crosslinkable group.

Methods of forming respective layers such as a light emitting layer, a hole transporting layer, an electron transporting layer, a hole injection layer and an electron injection layer in the light emitting device of the present invention include, for example, a method of vacuum vapor deposition from a powder and a method of film formation from solution or melted state when a low molecular weight compound is used, and, for example, a method of film formation from solution or melted state when a polymer compound is used.

The order and the number of layers to be laminated and the thickness of each layer may be controlled in view of external quantum efficiency and device life.

[Substrate/Electrode]

The substrate in the light emitting device may advantageously be a substrate on which an electrode can be formed and which does not chemically change in forming an organic layer, and is a substrate made of a material such as, for example, glass, plastic and silicon. In the case of an opaque substrate, it is preferable that an electrode most remote from the substrate is transparent or semi-transparent.

The material of the anode includes, for example, electrically conductive metal oxides and semi-transparent metals, preferably, indium oxide, zinc oxide and tin oxide; electrically conductive compounds such as indium.tin.oxide (ITO) and indium.zinc.oxide; a composite of silver, palladium and copper (APC); NESA, gold, platinum, silver and copper.

The material of the cathode includes, for example, metals such as lithium, sodium, potassium, rubidium, cesium, beryllium, magnesium, calcium, strontium, barium, aluminum, zinc and indium; alloys composed of two or more of them; alloys composed of one or more of them and at least one of silver, copper, manganese, titanium, cobalt, nickel, tungsten and tin; and graphite and graphite intercalation compounds. The alloy includes, for example, a magnesium-silver alloy, a magnesium-indium alloy, a magnesium-aluminum alloy, an indium-silver alloy, a lithium-aluminum alloy, a lithium-magnesium alloy, a lithium-indium alloy and a calcium-aluminum alloy.

The anode and the cathode may each take a lamination structure composed of two or more layers.

[Use]

For producing planar light emission by using a light emitting device, a planar anode and a planar cathode are disposed so as to overlap with each other. Patterned light emission can be produced by a method of placing a mask with a patterned window on the surface of a planer light emitting device, a method of forming extremely thick a layer intended to be a non-light emitting, thereby having the layer essentially no-light emitting or a method of forming an anode, a cathode or both electrodes in a patterned shape. By forming a pattern with any of these methods and disposing certain electrodes so as to switch ON/OFF independently, a segment type display capable of displaying numbers and letters and the like is provided. For producing a dot matrix display, both an anode and a cathode are formed in a stripe shape and disposed so as to cross with each other. Partial color display and multi-color display are made possible by a method of printing separately certain polymer compounds showing different emission or a method of using a color filter or a fluorescence conversion filter. The dot matrix display can be passively driven, or actively driven combined with TFT and the like. These displays can be used in computers, television sets, portable terminals and the like. The planar light emitting device can be suitably used as a planer light source for backlight of a liquid crystal display or as a planar light source for illumination. If a flexible substrate is used, it can be used also as a curved light source and a curved display.

EXAMPLES

The present invention will be illustrated further in detail by examples below, but the present invention is not limited to these examples.

Measurement of LC-MS was carried out according to the following method.

A measurement sample was dissolved in chloroform or tetrahydrofuran so as to give a concentration of about 2 mg/mL, and about 1 μL of the solution was injected into LC-MS (manufactured by Agilent Technologies, trade name: 1100LCMSD). As the mobile phase of LC-MS, acetonitrile and tetrahydrofuran were used while changing the ratio thereof and allowed to flow at a flow rate of 0.2 mL/min. As the column, L-column 2 ODS (3 μm) (manufactured by Chemicals Evaluation and Research Institute, internal diameter: 2.1 mm, length: 100 mm, particle size: 3 μm) was used.

Measurement of NMR was carried out according to the following method. 5 to 10 mg of a measurement sample was dissolved in about 0.5 mL of deuterated chloroform ($CDCl_3$), deuterated tetrahydrofuran (THF-$d_8$) or deuterated methylene chloride ($CD_2Cl_2$), and measurement was performed using an NMR apparatus (manufactured by Varian, Inc., trade name: MERCURY 300).

As the index of the purity of a compound, a value of the high performance liquid chromatography (HPLC) area percentage was used. This value is a value in high performance liquid chromatography (HPLC, manufactured by Shimadzu Corp., trade name: LC-20A) at 254 nm, unless otherwise state. In this operation, the compound to be measured was dissolved in tetrahydrofuran or chloroform so as to give a concentration of 0.01 to 0.2 wt %, and depending on the concentration, 1 to 10 μL of the solution was injected into HPLC. As the mobile phase of HPLC, acetonitrile and tetrahydrofuran were used and allowed to flow at a flow rate of 1 mL/min as gradient analysis of acetonitrile/tetrahydrofuran=100/0 to 0/100 (volume ratio). As the column, Kaseisorb ILC ODS 2000 (manufactured by Tokyo Chemical Industry Co., Ltd.) or an ODS column having an equivalent performance was used. As the detector, a photo diode array detector (manufactured by Shimadzu Corp., trade name: SPD-M20A) was used.

TLC-MS measurement was performed by the following method.

A measurement sample was dissolved in toluene, tetrahydrofuran or chloroform, the solution was applied on a TLC plate for DART (manufactured by Techno Applications, YSK5-100), and measurement was performed using TLC-MS (manufactured by JEOL Ltd., trade name: JMS-T100TD (The AccuTOF TLC)). The temperature of a helium gas in measurement was controlled in a range of 200 to 400° C.

PLQY and emission spectra were measured by the following method.

A metal complex was dissolved in xylene so as to give a concentration of 0.0008% by weight. The resultant xylene solution was charged into a 1 cm square quartz cell, then, oxygen was deaerated by bubbling with a nitrogen gas, to fabricate a measurement sample. The PLQY and emission spectrum of the resultant measurement sample were measured using an absolute PL quantum yield measuring apparatus (automatically controlled electrically driven monochrome light source type) (C9920-02G, manufactured by Hamamatsu Photonics K.K.), and the full width at half maximum of an emission spectrum (hereinafter, also referred to as "FWHM") was calculated from the resultant emission spectrum. Specifically, FWHM is calculated from a wavelength at which the normalized emission intensity is 0.5 when the emission intensity of the maximum peak in an emission spectrum of a metal complex is normalized to 1.0. When there are three or more wavelengths showing a normalized emission intensity of 0.5, it is calculated from a wavelength which is the shortest wavelength and a wavelength which is the longest wavelength. The excitation wavelength was 380 nm.

Example 1

Synthesis of Metal Complex M1

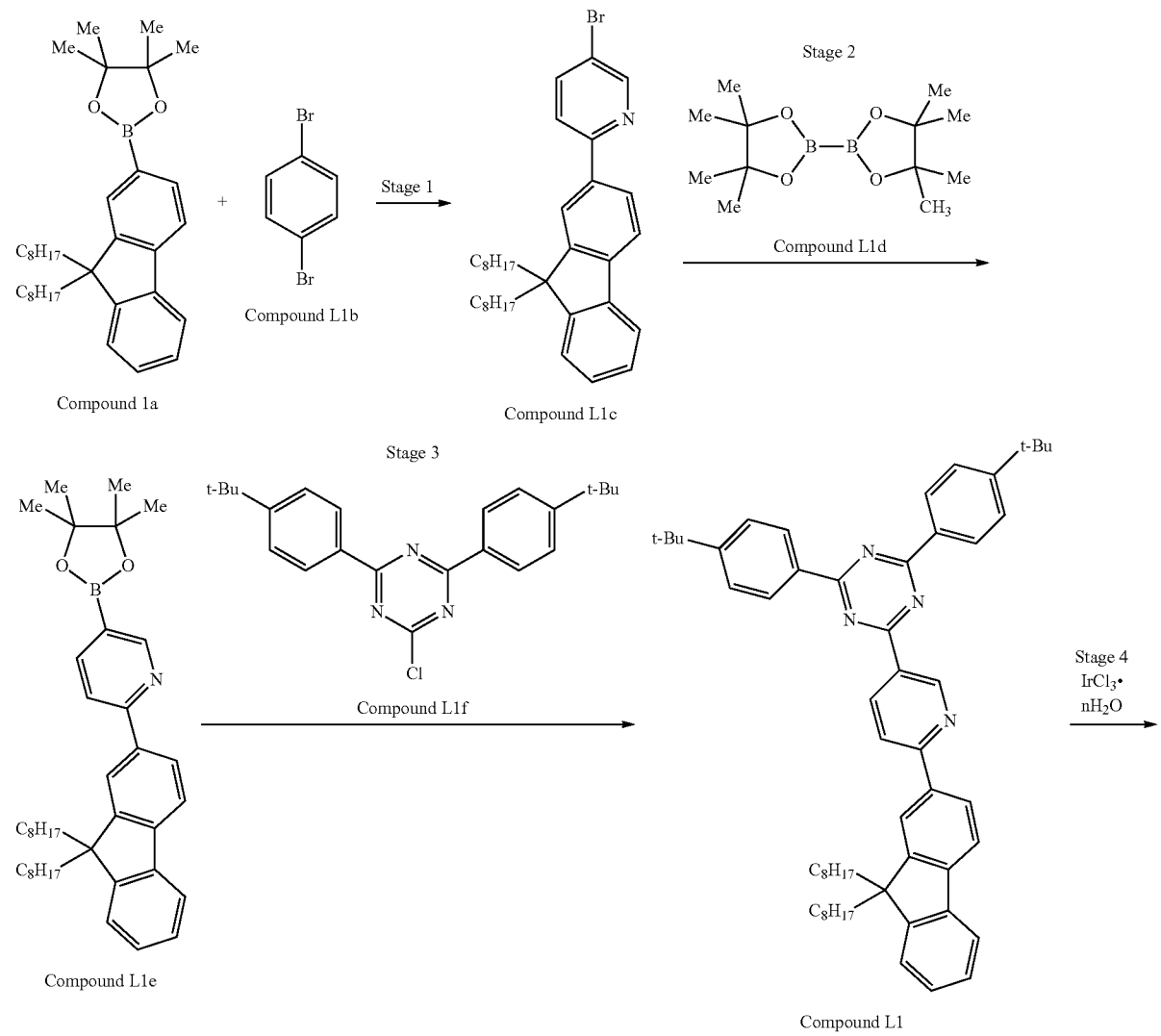

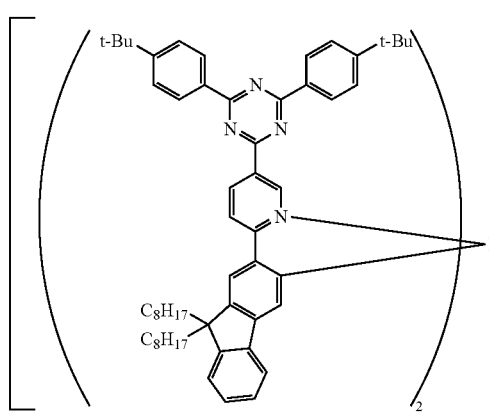
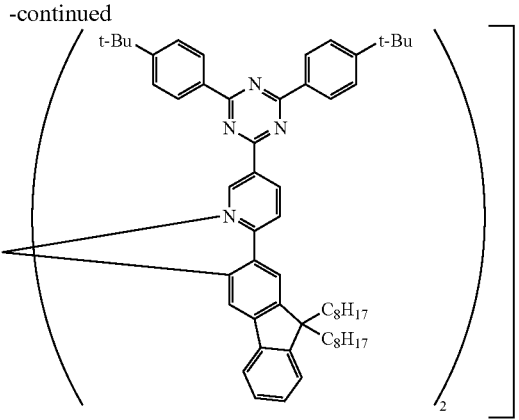

Metal complex M1a

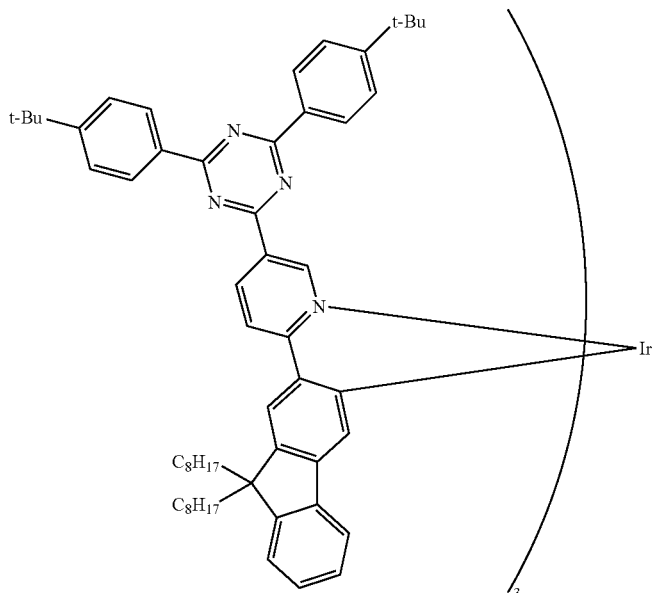

Metal complex M1

(Stage 1: Synthesis of Compound L1c)

An argon gas atmosphere was prepared in a reaction vessel, then, a compound L1a (12 g), a compound L1b (5.7 g), toluene (140 mL), tert-butanol (90 mL), tetrahydrofuran (70 mL), ion exchanged water (45 mL), tetrakis(triphenylphosphine)palladium(0) (530 mg) and a 40% by weight tetrabutylammonium hydroxide aqueous solution (60 g) were added, and the mixture was stirred at 50° C. for 15 hours.

The resultant reaction mixture was cooled down to room temperature, then, toluene was added, and the resultant organic layer was washed with ion exchanged water. Thereafter, the organic layer was dried over anhydrous sodium sulfate, filtrated, and the filtrate was concentrated under reduced pressure, to obtain an oily matter.

This oily matter was purified by silica gel column chromatography (a mixed solvent of toluene and hexane), then, dried under reduced pressure, to obtain a compound L1c (10 g, yield: 80%) as a colorless oily matter. The compound L1c showed an HPLC area percentage value of 99.5% or more.

TLC-MS (DART positive): m/z=546 [M+H]$^+$ (Stage 2: Synthesis of Compound L1e)

An argon gas atmosphere was prepared in a reaction vessel, then, the compound L1c (10 g), a compound L1d (7.2 g), [1,1'-bis(diphenylphosphospino)ferrocene]palladium(II) dichloride dichloromethane adduct (PdCl$_2$ (dppf).CH$_2$Cl$_2$, 780 mg), potassium acetate (5.6 g) and 1,2-dimethoxyethane (60 mL) were added, and the mixture was stirred under reflux with heating for 2 hours.

The resultant reaction mixture was cooled down to room temperature, then, toluene (90 mL) was added, and the mixture was filtrated through a filter paved with Celite, and the filtrate was concentrated under reduced pressure. Thereafter, to this were added hexane and activated carbon, and the mixture was stirred at 60° C. for 1 hour, then, the mixture was filtrated through a filter paved with Celite, and the filtrate was concentrated under reduced pressure, to obtain a compound L1e (12 g) as a colorless oily matter. The compound L1e showed an HPLC area percentage value of 99.0%.

(Stage 3: Synthesis of Compound L1)

An argon gas atmosphere was prepared in a light-shielded reaction vessel, then, the compound L1e (12 g), a compound L1f (8.7 g), tetrakis(triphenylphosphine)palladium(0) (440 mg), toluene (105 mL) and a 20% by weight tetraethylammonium hydroxide aqueous solution (56 g) were added, and the mixture was stirred at 70° C. for 3 hours. The compound L1f was synthesized according to a method described in JP-A No. 2008-179617.

The resultant reaction mixture was cooled down to room temperature, then, toluene was added, and the resultant organic layer was washed with ion exchanged water. Thereafter, the organic layer was dried over anhydrous sodium sulfate, filtrated, and the filtrate was concentrated under reduced pressure, to obtain a solid.

This solid was purified by silica gel column chromatography (a mixed solvent of toluene and hexane), then, dried under reduced pressure, to obtain a compound L1 (9.3 g, yield with respect to the compound L1c: 60%) as a pale yellow solid. The compound L1 showed an HPLC area percentage value of 99.5% or more.

TLC-MS (DART positive): m/z=812 [M+H]$^+$ $^1$H-NMR (CD$_2$Cl$_2$, 300 MHz): δ (ppm)=10.02 (d, 1H), 9.07 (dd, 1H), 8.72 (dt, 4H), 8.23 (s, 1H), 8.19 (dd, 1H), 8.06 (d, 1H), 7.87 (d, 1H), 7.81-7.78 (m, 1H), 7.65 (dt, 4H), 7.43-7.35 (m, 3H), 2.18-2.01 (m, 4H), 1.43 (s, 18H), 1.21-1.07 (m, 20H), 0.80 (t, 6H), 0.75-0.56 (m, 4H).

(Stage 4: Synthesis of Metal Complex M1a)

An argon gas atmosphere was prepared in a light-shielded reaction vessel, then, the compound L1 (480 mg) and 2-ethoxyethanol (40 mL) were added, and the mixture was heated up to 60° C. Thereafter, iridium(III) chloride hydrate (88 mg) dissolved in ion exchanged water (13 mL) was added to this, and the mixture was stirred at 105° C. for 15 hours.

The resultant reaction mixture was cooled down to room temperature, then, added into methanol (80 mL), and the mixture was stirred at room temperature for 1 hour. Thereafter, filtration was performed and the residue was dried under reduced pressure, to obtain a red solid (470) mg) containing a metal complex M1a.

(Stage 5: Synthesis of Metal Complex M1)

An argon gas atmosphere was prepared in a light-shielded reaction vessel, then, the red solid (470 mg) containing the metal complex M1a, the compound L1 (210 mg), silver(I) trifluoromethanesulfonate (87 mg), 2, 6-lutidine (40 μL) and diethylene glycol dimethyl ether (6.3 mL) were added, and the mixture was stirred at 150° C. for 17 hours.

The resultant reaction mixture was cooled down to room temperature, then, added into methanol (20 mL), and the mixture was stirred at room temperature for 1 hour. Thereafter, filtration was performed, toluene (20 mL) was added to the residue, and the resultant organic layer was washed with ion exchanged water. Thereafter, the organic layer was dried over anhydrous sodium sulfate, filtrated, and the filtrate was concentrated under reduced pressure, to obtain a solid.

This solid was purified by silica gel column chromatography (a mixed solvent of toluene and hexane) and recrystallization using a mixed solvent of ethyl acetate and acetonitrile in series, then, dried under reduced pressure, to obtain a metal complex M1 (200 mg, the yield with respect to the charge amount of IrCl$_3$.3H$_2$O is 30% if iridium(III) chloride hydrate is assumed to be trihydrate) as a red solid. The metal complex M1 showed an HPLC area percentage value of 99.5% or more.

LC-MS (APCI positive): m/z=2623 [M+H]$^+$

Example 2

Synthesis of Metal Complex M2

Stage 2

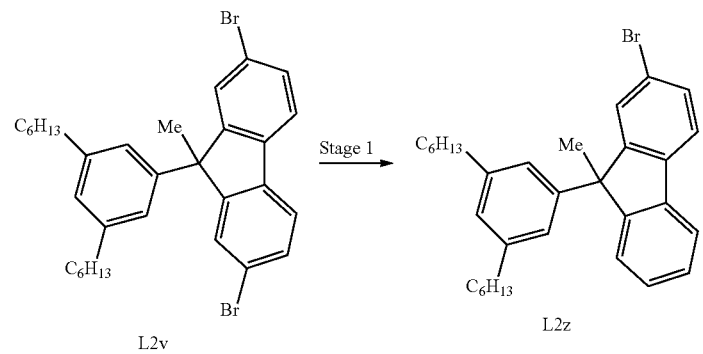

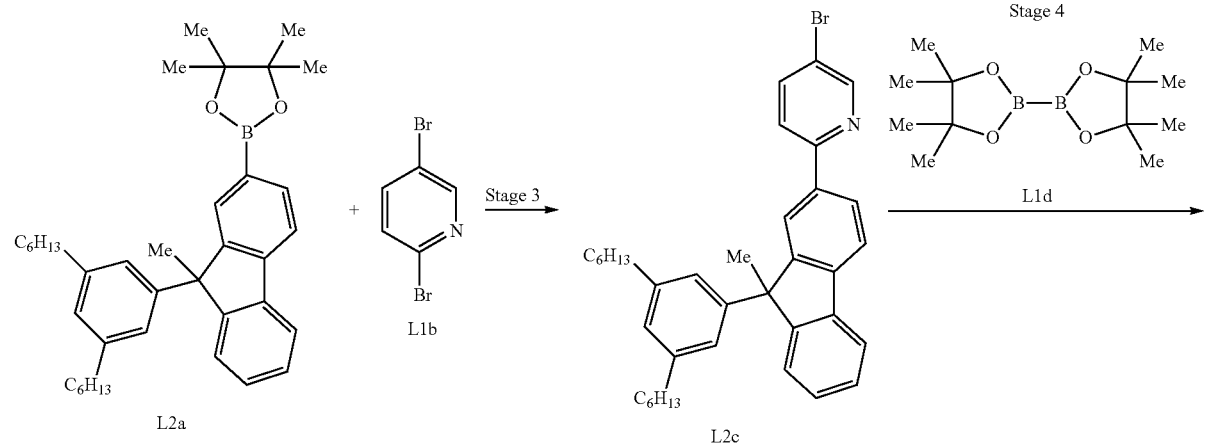

-continued
Stage 5
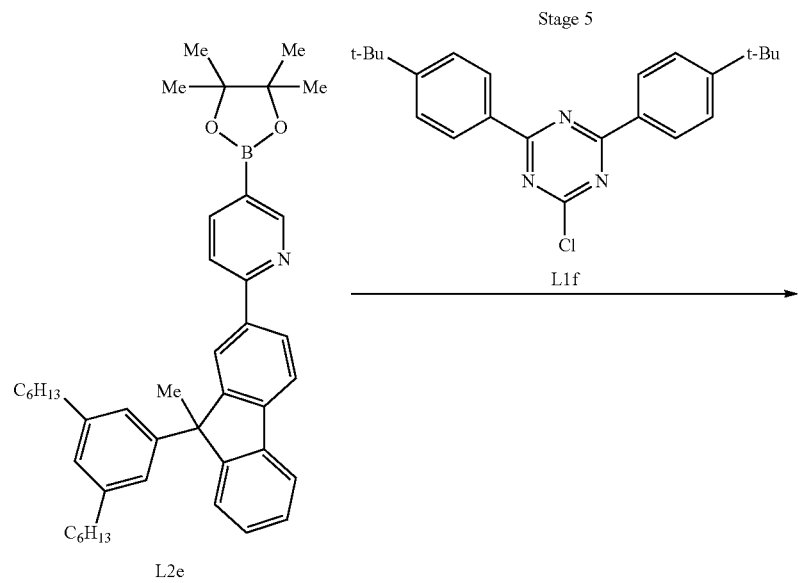
L1f
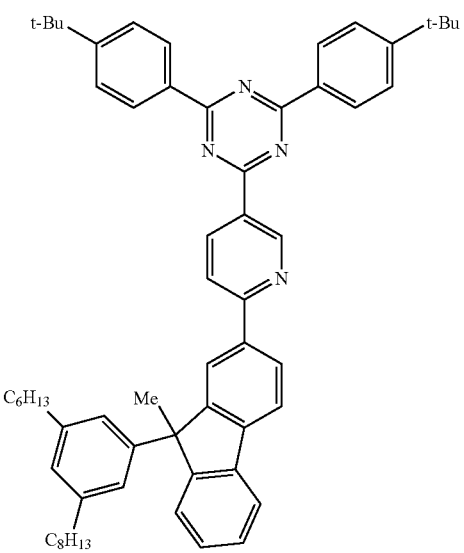
L2
Stage 6

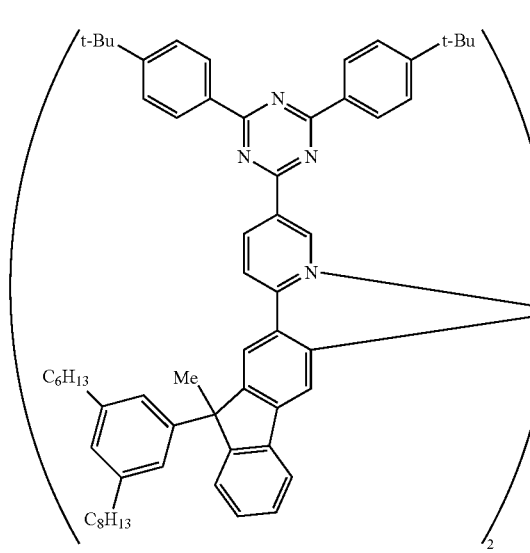

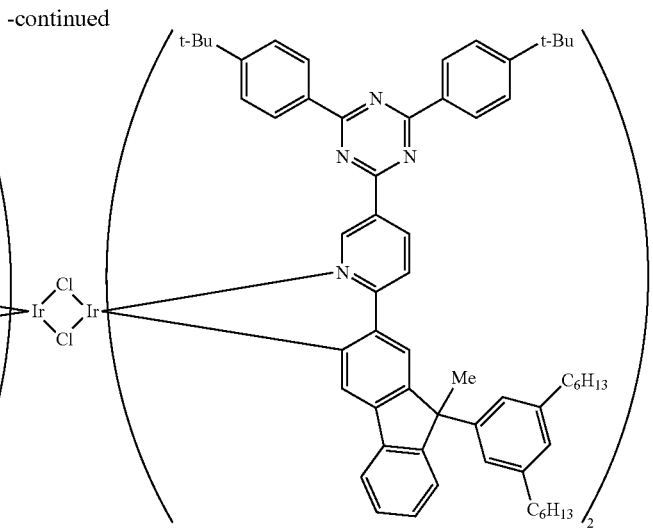

M2a

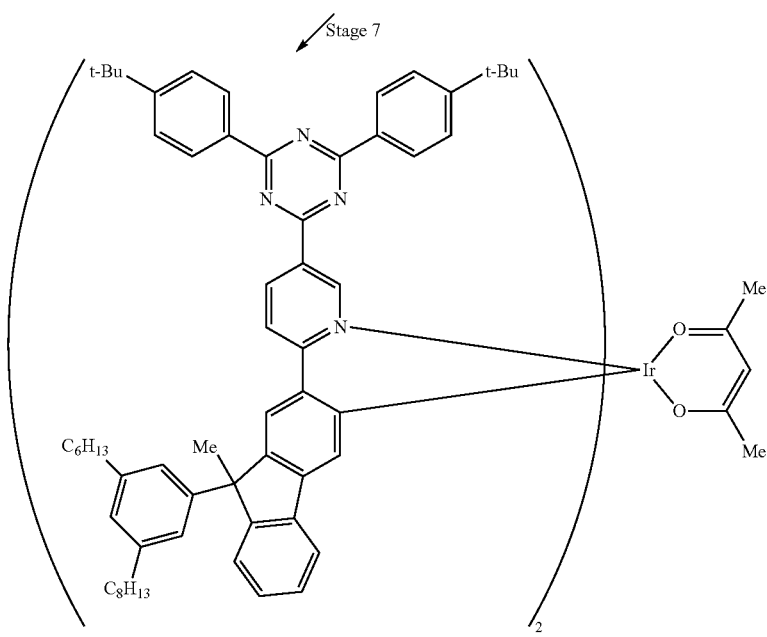

M2

(Stage 1: Synthesis of Compound L2z)

A nitrogen gas atmosphere was prepared in a reaction vessel, then, a compound L2y (87.4 g. synthesized according to a method described in JP-A No. 20212-144721 and tetrahydrofuran (dehydrated product, 870 mL) were added, and the mixture was cooled down to −74° C. while stirring. Thereafter, a hexane solution of n-butyllithium (1.6 mol/L, 100 mL) was added to this, and the mixture was stirred at −74° C. for 1 hour, Thereafter, ion exchanged water (440 mL) was added to this, and the solution was warmed up to room temperature, then, the solvent was distilled off under reduced pressure. The resultant residue was dissolved in toluene, then, the solution was washed with ion exchanged water. Thereafter, the organic layer was dried over anhydrous sodium sulfate, filtrated, and the filtrate was concentrated under reduced pressure, to obtain an oily matter.

This oily matter was purified by silica gel column chromatography (hexane), then, dried under reduced pressure, to obtain a compound L2z (63.5 g, yield: 84%) as a yellow oily matter. The compound L2z showed an HPLC area percentage value of 93.0%.

TLC-MS (DART positive): m/z=502 [M]$^+$ (Stage 2: Synthesis of Compound L2a)

A nitrogen gas atmosphere was prepared in a reaction vessel, then, the compound L2z (63.5 g), a compound L1d (35.2 g), [1,1'-bis(diphenylphosphino)ferrocene]palladium (II) dichloride dichloromethane adduct (3.1 g), 1,1'-bis(diphenylphosphino)ferrocene (2.1 g), potassium acetate (37.1 g) and 1,4-dioxane (370 mL) were added, and the mixture was stirred for 3.5 hours under reflux with heating. The resultant reaction mixture was cooled down to room temperature, then, toluene (550 mL) was added, and the mixture was filtrated through a filter paved with silica gel and Celite. The filtrate was concentrated under reduced pressure, then, toluene, activated white earth and activated carbon were added, and the mixture was stirred at 60° C. for 30 minutes, then, the mixture was filtrated through a filter paved with Celite. The filtrate was concentrated under reduced pressure, to obtain a compound L2a (78.5 g) as a yellow oily matter. The compound L2a showed an HPLC area percentage value of 89.9%.

TLC-MS (DART positive): m/z=550 [M]$^+$ (Stage 3: Synthesis of Compound L2c)

A nitrogen gas atmosphere was prepared in a reaction vessel, then, the compound L2a (69.4 g), a compound L1b (35.8 g), toluene (760 mL), tert-butanol (380 mL), tetrahydrofuran (500 mL), ion exchanged water (250 mL), tetrakis(triphenylphosphine)palladium(0) (4.4 g) and a 40% by weight tetrabutylammonium hydroxide aqueous solution (330 mL) were added, and the mixture was stirred at 50° C. for 15 hours. The resultant reaction mixture was cooled down to room temperature, then, toluene was added, and the resultant organic layer was washed with ion exchanged water. Thereafter, the organic layer was dried over anhydrous sodium sulfate, filtrated, and the filtrate was concentrated under reduced pressure, to obtain an oily matter.

This oily matter was purified by silica gel column-chromatography (a mixed solvent of chloroform and hexane) and purified by reverse phase silica gel column chromatography (a mixed solvent of ethyl acetate and acetonitrile), then, dried under reduced pressure, to obtain a compound L2c (57.2 g, yield: 78%) as a colorless oily matter. The compound L2c showed an HPLC area percentage value of 99.4%.

TLC-MS (DART positive): m/z=579 [M]$^+$ (Stage 4: Synthesis of Compound L2e)

A nitrogen gas atmosphere was prepared in a reaction vessel, then, the compound L2c (56.9 g), a compound L1d (37.3 g), [1,1'-bis(diphenylphosphino)ferrocene]palladium(II) dichloride dichloromethane adduct (4.8 g), potassium acetate (28.9 g) and 1,2-dimethoxyethane (390 mL) were added, and the mixture was stirred for 1.5 hours under reflux with heating. The resultant reaction mixture was cooled down to room temperature, then, toluene (590 mL) was added, and the mixture was filtrated through a filter paved with Celite. The filtrate was concentrated under reduced pressure, then, hexane and activated carbon were added, and the mixture was stirred at 65° C. for 1 hour, then, the mixture was filtrated through a filter paved with Celite. The filtrate was concentrated under reduced pressure, to obtain a compound L2e (82.1 g) as a brown oily matter. The compound L2e showed an HPLC area percentage value of 98.6%.

LC-MS (APCI positive): m/z=628 [M+H]$^+$ (Stage 5: Synthesis of Compound L2)

An argon gas atmosphere was prepared in a light-shielded reaction vessel, then, the compound L2e (41.4 g), a compound L1f (30.1 g), tetrakis(triphenylphosphine)palladium(0) (4.6 g), toluene (360 mL) and a 20% by weight tetraethylammonium hydroxide aqueous solution (390 mL) were added, and the mixture was stirred at 70° C. for 12 hours. The compound L1f was synthesized according to a method described in JP-A No. 2008-179617.

The resultant reaction mixture was cooled down to room temperature, then, toluene was added, and the resultant organic layer was washed with ion exchanged water. Thereafter, the organic layer was dried over anhydrous sodium sulfate, filtrated, and the filtrate was concentrated under reduced pressure, to obtain a solid.

This solid was purified by silica gel column chromatography (a mixed solvent of chloroform and hexane) and purified by reverse phase silica gel column chromatography (a mixed solvent of ethyl acetate and acetonitrile), then, purified by conducting recrystallization using a mixed solvent of ethyl acetate and methanol. Thereafter, the recrystallized product was dried under reduced pressure at 40° C. overnight, to obtain a compound L2 (45.5 g, yield: 82%) as a pale yellow solid. The compound L2 showed an HPLC area percentage value of 99.2%.

LC-MS (APCI positive): m/z=845.5 [M+H]$^+$ $^1$H-NMR (CD$_2$Cl$_2$, 300 MHz): δ (ppm)=9.95 (d, 1H), 9.02 (dd, 1H), 8.70 (dt, 4H), 8.21 (dd, 1H), 8.09 (d, 1H), 7.96 (t, 2H), 7.87 (d, 1H), 7.63 (dt, 4H), 7.43-7.27 (m, 3H), 6.87 (s, 3H), 2.49 (t, 4H), 1.96 (s, 3H), 1.58-1.21 (m, 34H), 0.85 (t, 6H).

(Stage 6: Synthesis of Metal Complex M2a)

An argon gas atmosphere was prepared in a light-shielded reaction vessel, then, the compound L2 (376 mg) and 2-ethoxyethanol (30 mL) were added, and the mixture was heated up to 80° C. Thereafter, iridium(III) chloride hydrate (71 mg) dissolved in ion exchanged water (10 mL) was added to this, and the mixture was stirred at 120° C. for 15 hours.

The resultant reaction mixture was cooled down to room temperature, then, added into methanol (40 mL), and the mixture was stirred at room temperature for 1 hour. Thereafter, filtration was performed, and the residue was dried under reduced pressure, to obtain a solid containing a metal complex M2a (This is called "solid A". 384 mg). This operation was repeated, to obtain a necessary amount of the solid A.

The solid A was purified by silica gel column chromatography (a mixed solvent of chloroform and hexane). Thereafter, the solid was dried under reduced pressure at 50° C. overnight, to obtain a red solid containing a metal complex M2a (This is called "solid B".).

(Stage 7: Synthesis of Metal Complex M2)

An argon gas atmosphere was prepared in a light-shielded reaction vessel, then, the solid B (500 mg), acetylacetone (260 mg), sodium carbonate (277 mg) and 2-ethoxyethanol (27 mL) were added, and the mixture was stirred at 120° C. for 3 hours.

The resultant reaction mixture was cooled down to room temperature, then, toluene (100 mL) was added, and the mixture was washed with ion exchanged water. Thereafter, the organic layer was dried over anhydrous sodium sulfate, and filtrated through a filter paved with silica gel, and the filtrate was concentrated under reduced pressure, to obtain a solid.

This solid was purified by washing with ethanol and washing with hexane, then, dried under reduced pressure, to obtain a metal complex M2 (320 mg) as a red solid. The metal complex M2 showed an HPLC area percentage value of 98.9% or more.

LC-MS (ESI positive): m/z=2018 [M+K]$^+$ $^1$H-NMR (CD$_2$Cl$_2$, 300 MHz): δ (ppm)=9.97 (d, 2H), 9.06 (d, 2H), 9.35 (d, 8H), 8.05 (d, 2H), 7.69 (m, 2H), 7.61 (d, 8H), 7.40-7.31 (m, 2H), 7.13 (t, 6H), 6.88-6.81 (m, 8H), 5.48 (s, 1H), 2.52-2.39 (m, 8H),) 2.06 (s, 6H), 1.87-1.83 (m, 6H), 1.61-1.40 (m, 44H), 1.26 (m, 24H), 0.89 (m, 12H).

Comparative Example 1

Synthesis of Metal Complex CM1

A metal complex CM1 was synthesized according to a method described in JP-A No. 2011-105701.

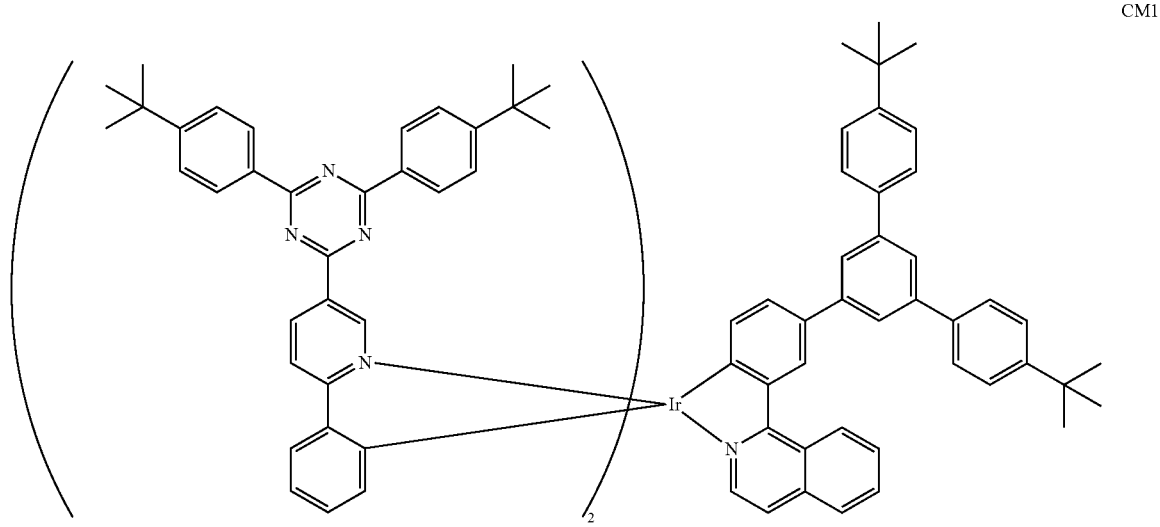

CM1

Measurement Example 1

Measurement of PLQY and Emission Spectrum of Metal Complex M1

PLQY and emission spectrum were measured, using a xylene solution of the metal complex M1 (0.0008% by weight). Light emission showing the maximum peak of an emission spectrum at 621 nm was observed, and FWHM of this emission spectrum was 36 nm, and PLQY was 72%.

Measurement Example 2

Measurement of PLQY and Emission Spectrum of Metal Complex M2

PLQY and emission spectrum were measured, using a xylene solution of the metal complex M2 (0.0008% by weight). Light emission showing the maximum peak of an emission spectrum at 624 nm was observed, and FWHM of this emission spectrum was 65 nm, and PLQY was 66%.

Measurement Example C1

Measurement of PLQY and Emission Spectrum of Metal Complex CM1

PLQY and emission spectrum were measured, using a xylene solution of the metal complex CM1 (0.0008% by weight). Light emission showing the maximum peak of an emission spectrum at 615 nm was observed, and FWHM of this emission spectrum was 88 nm, and PLQY was 53%.

Synthesis Example 1

Synthesis of Polymer Compound IP1

A polymer compound IP1 was synthesized by a method described in JP-A No. 2012-144722, using a monomer PM1 synthesized according to a method described in JP-A No. 2011-174062, a monomer PM2 synthesized according to a method described in International Publication WO2005/049546, a monomer PM3 synthesized according to a method described in International Publication WO2002/045184 and a monomer PM4 synthesized according to a method described in JP-A No. 2008-106241.

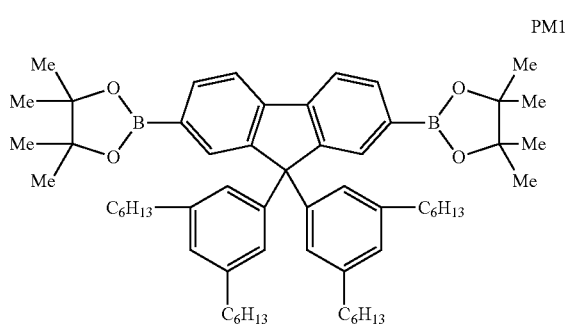

PM1

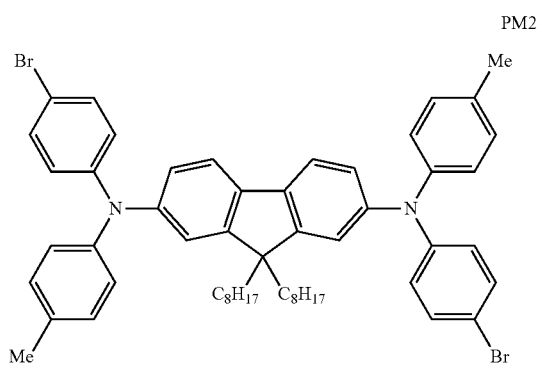

PM2

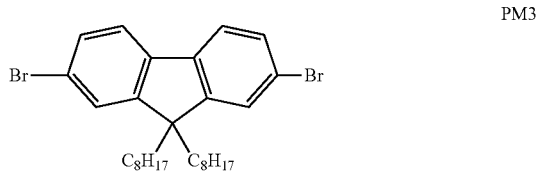

PM3

-continued

PM4

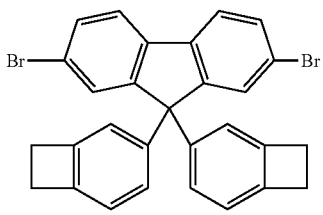

The polymer compound IP1 is a copolymer constituted of a constitutional unit derived from the monomer PM1, a constitutional unit derived from the monomer PM2, a constitutional unit derived from the monomer PM3 and a constitutional unit derived from the monomer PM4 at a molar ratio of 50:30:12.5:7.5, according to the theoretical values calculated from the amounts of the charged raw materials.

Synthesis Example 2

Synthesis of Compound PM5

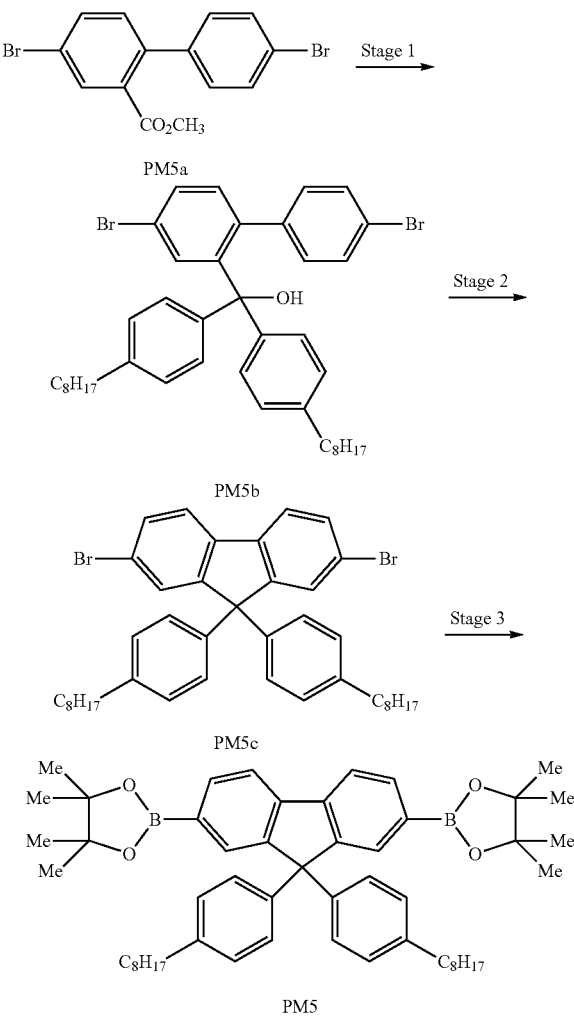

A compound PM5a was synthesized according to a method described in International Publication WO2012/086671.

(Stage 1: Synthesis of Compound PM5b)

A nitrogen gas atmosphere was prepared in a reaction vessel, then, 4-bromo-n-octylbenzene (250 g) and tetrahydrofuran (dehydrated product, 2.5 L) were added, and the mixture was cooled down to −70° C. or lower. Thereafter, a 2.5 mol/L n-butyllithium hexane solution (355 mL) was dropped into this, and the mixture was stirred for 3 hours at −70° C. or lower. Thereafter, a solution prepared by dissolving the compound PM5a (148 g) in tetrahydrofuran (dehydrated product, 400 mL) was dropped into this, then, the mixture was warmed up to room temperature, and stirred at room temperature overnight. The resultant reaction mixture was cooled down to 0° C., then, water (150 mL) was added and the mixture was stirred. The resultant reaction mixture was concentrated under reduced pressure, to remove the organic solvent. To the resultant reaction mixture were added hexane (1 L) and water (200 mL), and the aqueous layer was removed by a liquid-separation operation. The resultant organic layer was washed with saturated saline, then, magnesium sulfate was added and the layer was dried. The resultant mixture was filtrated, and the filtrate was concentrated under reduced pressure, to obtain a compound PM5b (330 g) as a yellow oily matter.

(Stage 2: Synthesis of Compound PM5c)

A nitrogen gas atmosphere was prepared in a reaction vessel, then, the compound PM5b (330 g) and dichloromethane (900 mL) were added, and the mixture was cooled down to 5° C. or lower. Thereafter, a 2.0 mol/L boron trifluoride diethyl ether complex (245 mL) was dropped into this. Thereafter, the mixture was warmed up to room temperature, and stirred at room temperature overnight. The resultant reaction mixture was added into a vessel containing ice water (2 L), stirred for 30 minutes, then, the aqueous layer was removed. The resultant organic layer was washed with a 10% by weight potassium phosphate aqueous solution (1 L) once, with water (1 L) twice, then, dried over magnesium sulfate. The resultant mixture was filtrated, and the filtrate was concentrated under reduced pressure, to obtain an oily matter. This oily matter was dissolved in toluene (200 mL), then, the solution was passed through a filter paved with silica gel, to obtain a toluene solution 1. After the toluene solution 1 was obtained, toluene (about 3 L) was further passed through a filter paved with silica gel, to obtain a toluene solution 2. The toluene solution 1 and the toluene solution 2 were mixed, then, concentrated under reduced pressure, to obtain an oily matter. To this oily matter was added methanol (500 mL), and the mixture was stirred. The resultant reaction mixture was filtrated, to obtain a solid. To this solid was added a mixed solvent of butyl acetate and methanol, and recrystallization thereof was repeated, to obtain a compound PM5c (151 g) as a white solid. The compound PM5c showed an HPLC area percentage value of 99.0% or more.

$^1$H-NMR (400 MHz/CDCl$_3$): δ (ppm)=7.56 (d, 2H), 7.49 (d, 2H), 7.46 (dd, 2H), 7.06 to 7.01 (m, 8H), 2.55 (t, 4H), 1.61 to 1.54 (m, 4H), 1.30 to 1.26 (m, 20H), 0.87 (t, 6H).

(Stage 3: Synthesis of Compound PM5)

A nitrogen gas atmosphere was prepared in a reaction vessel, then, the compound PM5c (100 g) and tetrahydrofuran (dehydrated product, 1000 mL) were added, and the mixture was cooled down to −70° C. or lower. Thereafter, a 2.5 mol/L n-butyllithium hexane solution (126 mL) was dropped into this, and the mixture was stirred for 5 hours at −70° C. or lower. Thereafter, 2-isopropoxy-4,4,5,5-tetramethyl-1,3,2-dioxaborolane (81 mL) was dropped into this. Thereafter, the mixture was warmed up to room temperature, and stirred at room temperature overnight. The resultant reaction mixture was cooled down to −30° C., and a 2.0 mol/L hydrochloric acid diethyl ether solution (143 mL) was dropped. Thereafter, the mixture was warmed up to room temperature and concentrated under reduced pressure, to obtain a solid. To this solid was added toluene (1.2 L), and the mixture was stirred at room temperature for 1 hour, then, passed through a filter paved with silica gel, to obtain a filtrate. This filtrate was concentrated under reduced pressure, to obtain a solid. To this solid was added methanol and the mixture was stirred, then, filtrated, to obtain a solid. This solid was purified by repeating recrystallization thereof using isopropyl alcohol, then, dried under reduced pressure at 50° C. overnight, to obtain a compound PM5 (72 g) as a white solid. The compound PM5 showed an HPLC area percentage value of 99.0% or more.

$^1$H-NMR (400 MHz/CDCl$_3$): δ (ppm)=7.82 (d, 2H), 7.81 (s, 2H), 7.76 (d, 2H), 7.11 (d, 4H), 7.00 (d, 4H), 2.52 (t, 4H), 1.59 to 1.54 (m, 4H), 1.36 to 1.26 (m, 20H), 1.31 (s, 24H), 0.87 (t, 6H).

Synthesis Example 3

Synthesis of Polymer Compound P1

(Stage 1)

An inert gas atmosphere was prepared in a reaction vessel, then, the monomer PM5 (4.77 g) (identical to the compound PM5), a monomer PM6 (0.773 g) synthesized according to a method described in International Publication WO2012/086671, the monomer PM3 (1.97 g), a monomer PM7 (0.331 g) synthesized according to a method described in International Publication WO2009/131255, a monomer PM8 (0.443 g) synthesized according to a method described in JP-A No. 2004-143419 and toluene (67 mL) were added, and the mixture was stirred while heating at 105° C.

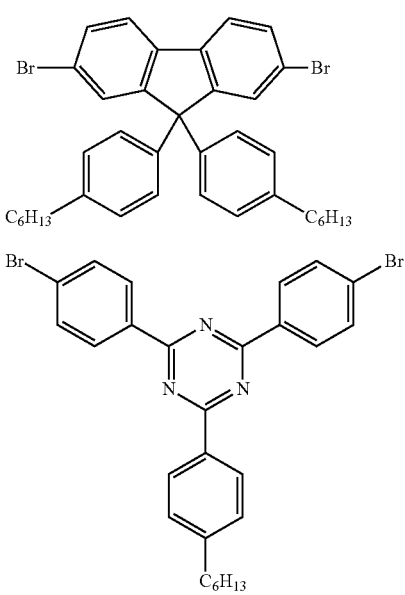

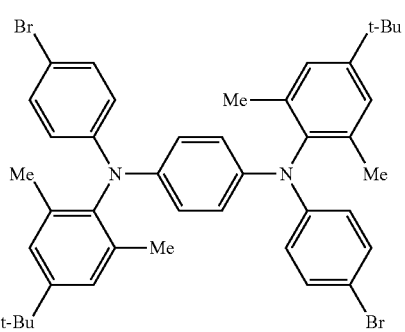

(Stage 2)
Thereafter, to this was added bistriphenylphosphinepalladium dichloride (4.2 mg), then, a 20% by weight tetraethylammonium hydroxide aqueous solution (20 mL) was dropped, then, the mixture was stirred for 3 hours under reflux.

(Stage 3)
Thereafter, to this were added phenylboronic acid (0.077 g), bistriphenylphosphinepalladium dichloride (4.2 mg), toluene (60 mL) and a 20% by weight tetraethylammonium hydroxide aqueous solution (20 mL), and the mixture was stirred for 24 hours under reflux.

(Stage 4)
The organic layer was separated from the aqueous layer, then, to the resultant organic layer were added sodium N,N-diethyldithiocarbamate trihydrate (3.33 g) and ion exchanged water (67 mL), and the mixture was stirred at 85° C. for 2 hours. The organic layer was separated from the aqueous layer, then, the organic layer was washed with ion exchanged water (78 mL) twice, with a 3% by weight acetic acid aqueous solution (78 mL) twice and with ion exchanged water (78 mL) twice in this order. The organic layer was separated from the aqueous layer, then, the organic layer was dropped into methanol to cause preparation of a solid which was then filtrated and dried, to obtain a solid. This solid was dissolved in toluene, and the solution was passed through a silica gel column and an alumina column through which toluene had been passed previously. The resultant solution was dropped into methanol to cause preparation of a solid which was then filtrated and dried, to obtain a polymer compound P1 (4.95 g). The polymer compound P1 had a polystyrene-equivalent number-average molecular weight (Mn) of $1.4 \times 10^5$ and a polystyrene-equivalent weight-average molecular weight (Mw) of $4.1 \times 10^5$.

The polymer compound P1 is a copolymer constituted of a constitutional unit derived from the monomer PM5, a constitutional unit derived from the monomer PM6, a constitutional unit derived from the monomer PM3, a constitutional unit derived from the monomer PM7 and a constitutional unit derived from the monomer PM8 at a molar ratio of 50:10:30:5:5, according to the theoretical values calculated from the amounts of the charged raw materials.

Example D1

Fabrication and Evaluation of Light Emitting Device D1

(Formation of Anode and Hole Injection Layer)
A glass substrate was fitted with an ITO film with a thickness of 45 nm by a sputtering method, to form an anode. On the anode, a polythiophene sulfonic acid type hole injecting agent AQ-1200 (manufactured by Plextronics) was spin-coated to form a film with a thickness of 65 nm, and the film was heated on a hot plate at 170° C. for 15 minutes under an air atmosphere, to form a hole injection layer.
(Formation of Hole Transporting Layer)

The polymer compound IP1 was dissolved in xylene at a concentration of 0.70% by weight. On the hole injection layer, the resultant xylene solution was spin-coated to form a film with a thickness of 20 nm, and the film was heated on a hot plate at 180° C. for 60 minutes under a nitrogen gas atmosphere, to form a hole transporting layer.
(Formation of Light Emitting Layer)

The polymer compound P1 and the metal complex M1 (polymer compound P1/metal complex M1=92.5% by weight/7.5% by weight) were dissolved in xylene at a concentration of 1.7% by weight. On the hole transporting layer, the resultant xylene solution was spin-coated to form a film with a thickness of 90 nm, and the film was heated at 150° C. for 10 minutes under a nitrogen gas atmosphere, to form a light emitting layer.
(Formation of Cathode)

The substrate carrying thereon the light emitting layer formed was placed in a vapor deposition machine and the pressure was reduced to $1.0 \times 10^{-4}$ Pa or lower, then, as cathode, sodium fluoride was vapor-deposited with a thickness of about 4 nm on the light emitting layer, then, aluminum was vapor-deposited with a thickness of about 80 nm on the sodium fluoride layer. After vapor deposition, it was sealed using a glass substrate, to fabricate a light emitting device D1.

Example D1

Fabrication and Evaluation of Light Emitting Device D1

Figure 2:
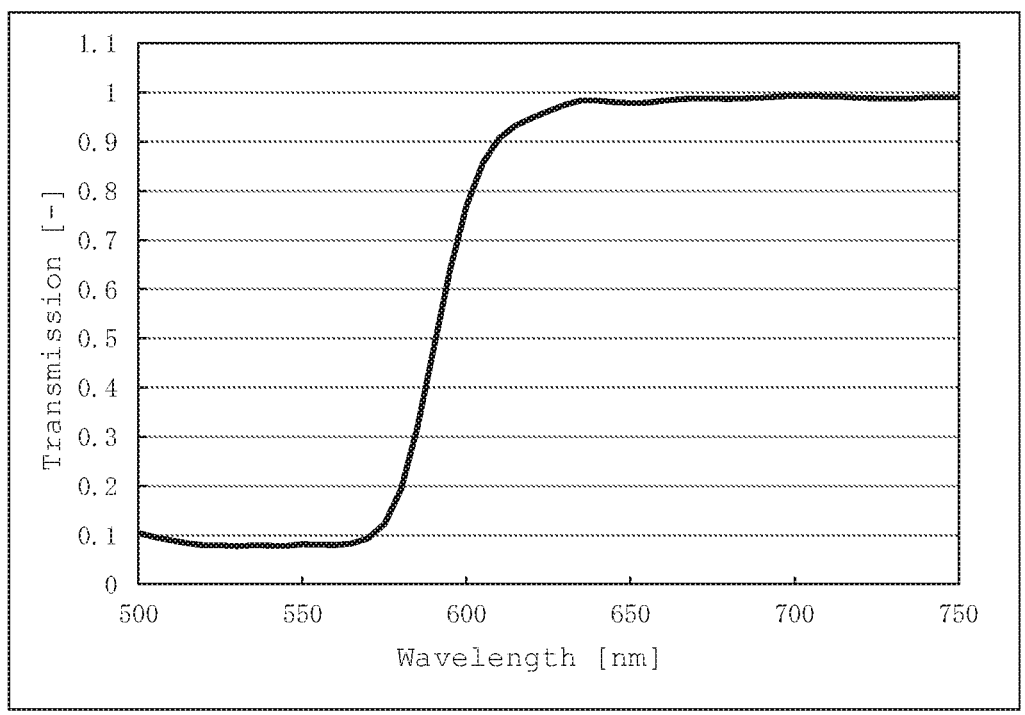
FIG. 2 is a view showing the transmission spectrum of a color filter used in an example.

When voltage was applied to the light emitting device D1, light emission showing the maximum peak of an emission spectrum at 625 nm was observed, and the CIE chromaticity coordinate (x, y)=(0.668, 0.329). FWHM of this emission spectrum was 44 nm. When the light emitting device D1 was used together with a color filter shown in FIG. 2, the external quantum efficiency at 1000 cd/m² was 12.6%.

Example D2

Fabrication and Evaluation of Light Emitting Device D2

A light emitting device D2 was fabricated in the same manner as in Example D1, except that the polymer compound P1 and the metal complex M2 were used instead of the polymer compound P1 and the metal complex M1 in Example D1.

When voltage was applied to the light emitting device D2, light emission showing the maximum peak of an emission spectrum at 625 nm was observed, and the CIE chromaticity coordinate (x, y)=(0.664, 0.333). FWHM of this emission spectrum was 62 nm. When the light emitting device D2 was used together with a color filter shown in FIG. 2, the external quantum efficiency at 1000 cd/m² was 9.53%.

INDUSTRIAL APPLICABILITY

The present invention can provide a metal complex showing excellent quantum yield and excellent in the full width at half maximum of an emission spectrum.

The invention claimed is:
1. A metal complex represented by the following formula (1):

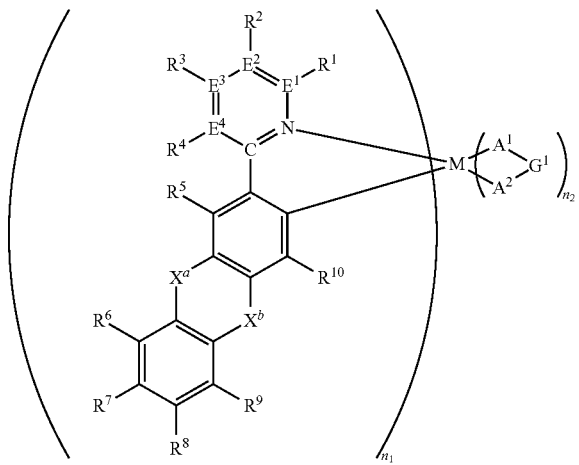

wherein
M represents an iridium atom or a platinum atom,
$n_1$ represents 1, 2 or 3, $n_2$ represents 0, 1 or 2, $n_1+n_2$ is 3 when M is an iridium atom and $n_1+n_2$ is 2 when M is a platinum atom,
$E^1$, $E^2$, $E^3$ and $E^4$ each independently represent a nitrogen atom or a carbon atom, and when a plurality of $E^1$, $E^2$, $E^3$ and $E^4$ are present, they may be the same or different at each occurrence, and $R^1$ is not present when $E^1$ is a nitrogen atom, $R^2$ is not present when $E^2$ is a nitrogen atom, $R^3$ is not present when $E^3$ is a nitrogen atom, and $R^4$ is not present when $E^4$ is a nitrogen atom,
$R^1$, $R^2$, $R^3$, $R^4$, $R^5$, $R^6$, $R^7$, $R^8$, $R^9$ and $R^{10}$ each independently represent a hydrogen atom, an alkyl group, a cycloalkyl group, an alkoxy group, a cycloalkoxy group, an aryl group, an aryloxy group, a monovalent heterocyclic group or a halogen atom, and these groups optionally have a substituent, and when a plurality of $R^1$, $R^2$, $R^3$, $R^4$, $R^5$, $R^6$, $R^7$, $R^8$, $R^9$ and $R^{10}$ are present, they may be the same or different at each occurrence, and $R^1$ and $R^2$, $R^2$ and $R^3$, $R^3$ and $R^4$, $R^4$ and $R^5$, $R^6$ and $R^7$, $R^7$ and $R^8$, and $R^8$ and $R^9$ each may be combined together to form a ring together with the atoms to which they are attached, and at least one selected from the group consisting of $R^1$, $R^2$, $R^3$ and $R^4$ is a group represented by the following formula (D-A) or (D-B),
$X^a$ and $X^b$ each independently represent a direct bond, an oxygen atom, a sulfur atom, —C(=O)—, —CR$^{Xa}_2$— or —NR$^{Xa}$—, R$^{Xa}$ represents a hydrogen atom, an alkyl group, a cycloalkyl group, an aryl group or a monovalent heterocyclic group, and these groups optionally have a substituent, and when a plurality of R$^{Xa}$ are present, they may be the same or different and may be combined together to form a ring together with the carbon atoms to which they are attached, and when a plurality of $X^a$ and $X^b$ are present, they may be the same or different at each occurrence, and at least one of $X^a$ and $X^b$ is an oxygen atom, a sulfur atom, —C(=O)—, —CR$^{Xa}_2$— or —NR$^{Xa}$—, and A$^1$-G$^1$-A$^2$ represents an anionic bidentate ligand, G$^1$ represents an atomic group constituting a bidentate ligand together with A$^1$ and A$^2$, A$^1$ and A$^2$ each independently represent a carbon atom, an oxygen atom or a nitrogen atom, and these atoms each may be an atom constituting a ring, and when a plurality of A$^1$-G$^1$-A$^2$ are present, they may be the same or different,

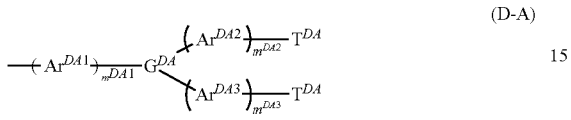

(D-A)

wherein
m$^{DA1}$, m$^{DA2}$ and m$^{DA3}$ each independently represent an integer of 0 or more, G$^{DA}$ represents an aromatic hydrocarbon group or a heterocyclic group, and these groups optionally have a substituent, Ar$^{DA1}$, Ar$^{DA2}$ and Ar$^{DA3}$ each independently represent an arylene group or a divalent heterocyclic group, and these groups optionally have a substituent, and when a plurality of Ar$^{DA1}$, Ar$^{DA2}$ and Ar$^{DA3}$ are present, they may be the same or different at each occurrence, and T$^{DA}$ represents an aryl group or a monovalent heterocyclic group, and these groups optionally have a substituent, and the plurality of T$^{DA}$ may be the same or different,

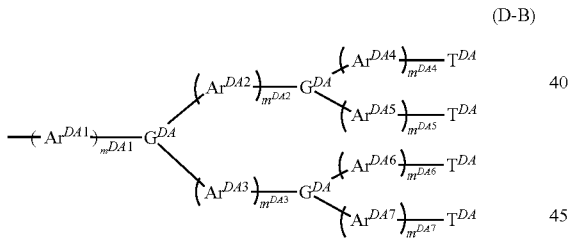

(D-B)

wherein
m$^{DA1}$, m$^{DA2}$, m$^{DA3}$, m$^{DA4}$, m$^{DA5}$, m$^{DA6}$ and m$^{DA7}$ each independently represent an integer of 0 or more, G$^{DA}$ represents an aromatic hydrocarbon group or a heterocyclic group, and these groups optionally have a substituent, and the plurality of G$^{DA}$ may be the same or different, Ar$^{DA1}$, Ar$^{DA2}$, Ar$^{DA3}$, Ar$^{DA4}$, Ar$^{DA5}$, Ar$^{DA6}$ and Ar$^{DA7}$ each independently represent an arylene group or a divalent heterocyclic group, and these groups optionally have a substituent, and when a plurality of Ar$^{DA1}$, Ar$^{DA2}$, Ar$^{DA3}$, Ar$^{DA4}$, Ar$^{DA5}$, Ar$^{DA6}$ and Ar$^{DA7}$ are present, they may be the same or different at each occurrence, and T$^{DA}$ represents an aryl group or a monovalent heterocyclic group, and these groups optionally have a substituent, and the plurality of T$^{DA}$ may be the same or different.

2. The metal complex according to claim 1, wherein the R$^2$ is the group represented by the formula (D-A).

3. The metal complex according to claim 1, wherein the group represented by the formula (D-A) is a group represented by the following formula (D-A1), (D-A2) or (D-A3):

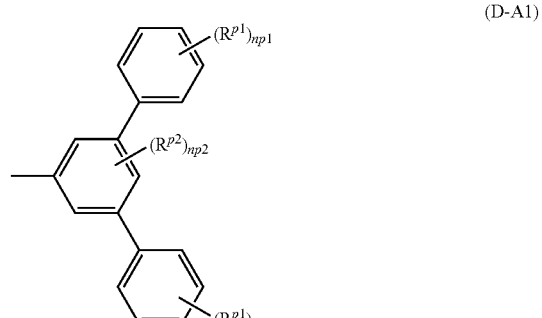

(D-A1)

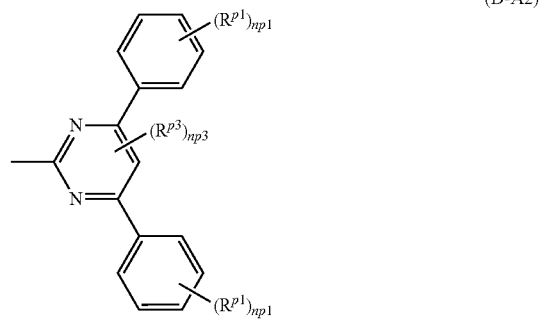

(D-A2)

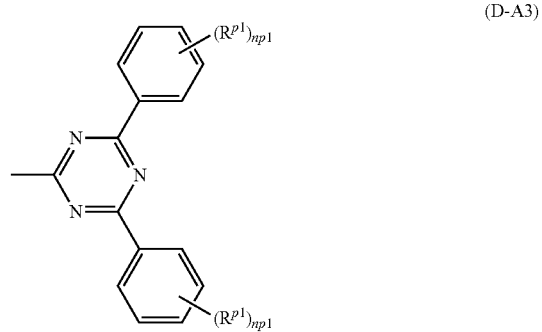

(D-A3)

wherein
R$^{p1}$, R$^{p2}$ and R$^{p3}$ each independently represent an alkyl group, a cycloalkyl group, an alkoxy group, a cycloalkoxy group or a halogen atom, and a plurality of R$^{p1}$ and R$^{p2}$ are present, they may be the same or different at each occurrence, and np1 represents an integer of 0 to 5, np2 represents an integer of 0 to 3, and np3 represents 0 or 1, and the plurality of np1 may be the same or different.

4. The metal complex according to claim 3, wherein the group represented by the formula (D-A) is the group represented by the formula (D-A3).

5. The metal complex according to claim 1, wherein X$^a$ is —CR$^{Xa}_2$—, and X$^b$ is a direct bond.

6. The metal complex according to claim 1, wherein the E$^1$, E$^2$, E$^3$ and E$^4$ are each a carbon atom.

7. The metal complex according to claim 1, wherein M is an iridium atom, n$_1$ is 3, and n$_2$ is 0.

8. A metal complex represented by the following formula (2):

(2)

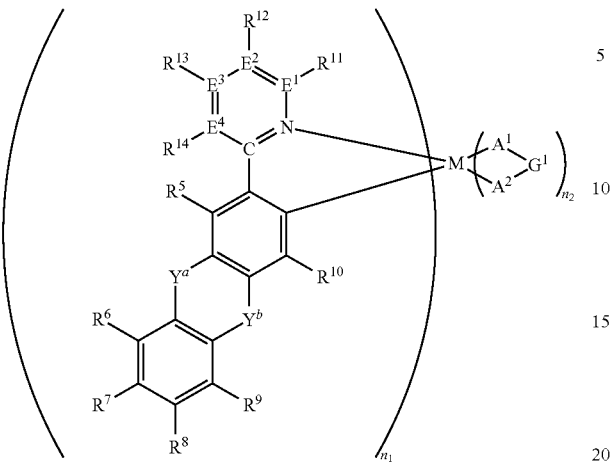

wherein
M represents an iridium atom or a platinum atom,
$n_1$ represents 1, 2 or 3, $n_2$ represents 0, 1 or 2, $n_1+n_2$ is 3 when M is an iridium atom, and $n_1+n_2$ is 2 when M is a platinum atom,
$E^1$, $E^2$, $E^3$ and $E^4$ each independently represent a nitrogen atom or a carbon atom, when a plurality of $E^1$, $E^2$, $E^3$ and $E^4$ are present, they may be the same or different at each occurrence, and $R^{11}$ is not present when $E^1$ is a nitrogen atom, $R^{12}$ is not present when $E^2$ is a nitrogen atom, $R^{13}$ is not present when $E^3$ is a nitrogen atom, and $R^{14}$ is not present when $E^4$ is a nitrogen atom,
$R^{11}$, $R^{12}$, $R^{13}$, $R^{14}$, $R^5$, $R^6$, $R^7$, $R^8$, $R^9$ and $R^{10}$ each independently represent a hydrogen atom, an alkyl group, a cycloalkyl group, an alkoxy group, a cycloalkoxy group, an aryl group, an aryloxy group, a monovalent heterocyclic group or a halogen atom, and these groups optionally have a substituent, and when a plurality of $R^{11}$, $R^{12}$, $R^{13}$, $R^{14}$, $R^5$, $R^6$, $R^7$, $R^8$, $R^9$ and $R^{10}$ are present, they may be the same or different at each occurrence, and $R^{11}$ and $R^{12}$, $R^{12}$ and $R^{13}$, $R^{13}$ and $R^{14}$, $R^{14}$ and $R^5$, $R^6$ and $R^7$, $R^7$ and $R^8$, and $R^8$ and $R^9$ each may be combined together to form a ring together with the atoms to which they are attached,
$Y^a$ and $Y^b$ each independently represent a direct bond, an oxygen atom, a sulfur atom, —C(=O)—, —CR$^{Ya}$R$^{Yb}$— or —NR$^{Yc}$—, R$^{Ya}$ represents an alkyl group or a cycloalkyl group, and these groups optionally have an aryl group or a monovalent heterocyclic group as a substituent, R$^{Yb}$ represents an aryl group having an alkyl group as a substituent or a monovalent heterocyclic group having an alkyl group as a substituent, and these groups optionally further have a substituent, R$^{Yc}$ represents a hydrogen atom, an alkyl group, a cycloalkyl group, an aryl group or a monovalent heterocyclic group, and these groups optionally have a substituent, and at least one of $Y^a$ and $Y^b$ is —CR$^{Ya}$R$^{Yb}$—, and
$A^1$-$G^1$-$A^2$ represents an anionic bidentate ligand, $G^1$ represents an atomic group constituting a bidentate ligand together with $A^1$ and $A^2$, $A^1$ and $A^2$ each independently represent a carbon atom, an oxygen atom or a nitrogen atom, and these atoms each may be an atom constituting a ring, and when a plurality of $A^1$-$G^1$-$A^2$ are present, they may be the same or different.

9. The metal complex according to claim 8, wherein $Y^a$ is —CR$^{Ya}$R$^{Yb}$—, and $Y^b$ is a direct bond.

10. The metal complex according to claim 8, wherein R$^{Ya}$ is an alkyl group optionally having a substituent.

11. The metal complex according to claim 8, wherein R$^{Yb}$ is an aryl group having an alkyl group as a substituent.

12. The metal complex according to claim 11, wherein R$^{Yb}$ is a phenyl group having an alkyl group as a substituent.

13. The metal complex according to claim 8, wherein at least one selected from the group consisting of $R^{11}$, $R^{12}$, $R^{13}$ and $R^{14}$ is a group represented by the following formula (D-A) or (D-B):

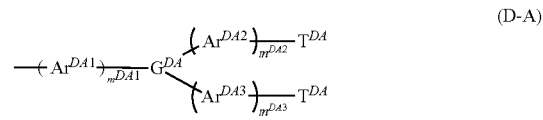
(D-A)

wherein
$m^{DA1}$, $m^{DA2}$ and $m^{DA3}$ each independently represent an integer of 0 or more,
$G^{DA}$ represents an aromatic hydrocarbon group or a heterocyclic group, and these groups optionally have a substituent,
Ar$^{DA1}$, Ar$^{DA2}$ and Ar$^{DA3}$ each independently represent an arylene group or a divalent heterocyclic group, and these groups optionally have a substituent, and when a plurality of Ar$^{DA1}$, Ar$^{DA2}$ and Ar$^{DA3}$ are present, they may be the same or different at each occurrence, and
$T^{DA}$ represents an aryl group or a monovalent heterocyclic group, and these groups optionally have a substituent, and the plurality of $T^{DA}$ may be the same or different,

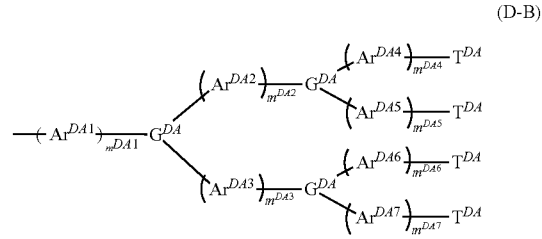
(D-B)

wherein
$m^{DA1}$, $m^{DA2}$, $m^{DA3}$, $m^{DA4}$, $m^{DA5}$, $m^{DA6}$ and $m^{DA7}$ each independently represent an integer of 0 or more,
$G^{DA}$ represents an aromatic hydrocarbon group or a heterocyclic group, and these groups optionally have a substituent, and the plurality of $G^{DA}$ may be the same or different,
Ar$^{DA1}$, Ar$^{DA2}$, Ar$^{DA3}$, Ar$^{DA4}$, Ar$^{DA5}$, Ar$^{DA6}$ and Ar$^{DA7}$ each independently represent an arylene group or a divalent heterocyclic group, and these groups optionally have a substituent, and when a plurality of Ar$^{DA1}$, Ar$^{DA2}$, Ar$^{DA3}$, Ar$^{DA4}$, Ar$^{DA5}$, Ar$^{DA6}$ and Ar$^{DA7}$ are present, they may be the same or different at each occurrence, and $T^{DA}$ represents an aryl group or a monovalent heterocyclic group, and these groups optionally have a substituent, and the plurality of $T^{DA}$ may be the same or different.

14. A composition comprising
the metal complex according to claim 1 and
at least one material selected from the group consisting of a hole transporting material, a hole injection material, an electron transporting material, an electron injection material, a light emitting material, an antioxidant and a solvent.

15. A light emitting device produced using the metal complex according to claim 1.

* * * * *